United States Patent [19]
Jeffreys et al.

[11] Patent Number: 5,853,989
[45] Date of Patent: Dec. 29, 1998

[54] METHOD OF CHARACTERISATION OF GENOMIC DNA

[75] Inventors: Alec John Jeffreys, Leicester; Stephen Little, Chester; Richard Mark Ferrie; Jannine Brownie, both of Cheshire, all of Great Britain

[73] Assignee: Zeneca Limited, London, United Kingdom

[21] Appl. No.: 643,181

[22] Filed: May 6, 1996

Related U.S. Application Data

[63] Continuation-in-part of Ser. No. 418,859, Apr. 5, 1995, which is a continuation of Ser. No. 935,107, Aug. 26, 1992, abandoned.

[30] Foreign Application Priority Data

| | | | |
|---|---|---|---|
| Aug. 27, 1991 | [GB] | United Kingdom | 9118371 |
| Sep. 6, 1991 | [GB] | United Kingdom | 9119089 |
| Nov. 20, 1991 | [GB] | United Kingdom | 9124636 |
| Apr. 3, 1992 | [GB] | United Kingdom | 9207379 |
| Jun. 15, 1992 | [GB] | United Kingdom | 9212627 |
| Jun. 17, 1992 | [GB] | United Kingdom | 9212881 |

[51] Int. Cl.⁶ .................. C12Q 1/68; C12P 19/34
[52] U.S. Cl. ........................... 435/6; 435/91.2
[58] Field of Search ....................... 435/6, 91.2

[56] References Cited

U.S. PATENT DOCUMENTS

| | | | |
|---|---|---|---|
| 5,066,584 | 11/1991 | Gyllensten et al. | 435/91.2 |
| 5,104,792 | 4/1992 | Silver et al. | 435/6 |
| 5,175,082 | 12/1992 | Jeffreys | 435/6 |

FOREIGN PATENT DOCUMENTS

| | | |
|---|---|---|
| 0 332 435 | 9/1989 | European Pat. Off. . |
| A-0 332 435 | 9/1989 | European Pat. Off. . |
| A-0 342 717 | 11/1989 | European Pat. Off. . |
| A-0 370 719 | 5/1990 | European Pat. Off. . |
| 0 416 817 | 3/1991 | European Pat. Off. . |
| A-0 416 817 | 3/1991 | European Pat. Off. . |
| 0 497 527 | 8/1992 | European Pat. Off. . |
| A-0 519 338 | 12/1992 | European Pat. Off. . |
| A-2 188 323 | 9/1987 | United Kingdom . |
| A-2 252 407 | 8/1992 | United Kingdom . |
| WO-89/10414 | 11/1989 | WIPO . |
| WO 90/11372 | 10/1990 | WIPO . |
| WO-90/11369 | 10/1990 | WIPO . |
| WO-90/11372 | 10/1990 | WIPO . |
| WO 90/15881 | 12/1990 | WIPO . |
| WO-92/18646 | 10/1992 | WIPO . |

OTHER PUBLICATIONS

Skolnick et al Genomics 2:273–279 (1988).
Mullis et al Cold Spring Harbor Symp. on Quat. Biol pp. 263–273 (1986).
Database WPI, Section Ch, Week 9119, Derwent Pub. Ltd, London, GB; Clars B04f, AN91–140560, XP002010671 A–7,454,171 (Silver J.) 15 May 1990—Abstract.
Mullis et al, "Specific Enzymatic Amplification of DNA In Vitro: The Polymerase Chain Reaction", Cold Harbor Symposia on Quantitative Biology, vol. L1, pp. 263–273 (1986).
Erlich et al, "Recent Advances in the Polymerase Chain Reaction", Science 252(5013):1643–1651 (1991).
Jeffreys et al, "Minisatellite repeat coding as a digital approach to DNA typing", Nature 354:204–29 (1991).
Jeffreys et al, "Repeat Unit Sequence Variation in Minisatellites: A Novel Source of DNA Polymorphism for Studying Variation and Mutation by Single Molecule Analysis", Cell 60:473–485 (1990).
Monckton et al, "Minisatellite Isoallele Discrimination in Pseudohomozygotes by Single Molecule PCR and Variant Repeat Mapping", Genomics 11:465–467 (1991).
Gibbs, "DNA Amplification by the Polymerase Chain Reaction", Anal. Chem. 62:1202–1214 (1990).
U.S. Patent Application Serial No. 07/504,591—Suldiner et al, "RNA Template–Specific Polymerase Chain Reaction".
Honghua Li et al, "Amplifcation and analysis of DNA sequences in single human sperm and diploid cells", Nature 335:414–417 (1988).
Mullis et al, "Specific enzymatic amplification of DNA . . . ", Cold Spring Harber Symposium Qunt. Biol. L1:263–273 (1986).
Weber and May, "Abundant Class of Human DNA Polymorphisms Which Can Be Typed Using the Polymerase Chain Reaction", Am. J. Hum. Genet. 44:388–396 (1989).
Farr et al, "New Variations on the them", Nature 354:184 (1991).

Primary Examiner—Eggerton A. Campbell
Attorney, Agent, or Firm—Nixon & Vanderhye P.C.

[57] ABSTRACT

The present invention relates generally to a method of characterizing a sample of genomic DNA and to nucleotide sequences employed in the method as well as kits comprising these. In particular the invention involves the use of primers which selectively prime specific type(s) of internal repeat unit in a tandemly repeated region. The method of the invention is particularly useful in forensic or paternity studies and provides individual sample codes suitable for computerized storage on, and retrieval from, a database.

17 Claims, 46 Drawing Sheets

Fig.3A.

```
         PCR     ?attaatataaaaaaaaaaaaaaaaaaataatattaaaaaaaaaaaaaaaaaataaatataaaaaat....
1
         HaeIII  tattaatataaaaaaaaaaaaaaaaaaataatattaaaaaaaaaaaaaaaaaataaatataaaaaat....

PCR     ?taaaaaaaaaaaaOaaaaaaOaaaaaaaOaaatatttattaaaaaaaaaaaaaaaaaaaaaa....
2                              x       x       x
         HaeIII  ataaaaaaaaaaaataaaaaataaaaaaataaatatttattaaaaaaaaaaaaaaaaaaaaaa...

PCR     ?aattatttOaaOaaaaOaatattttttatattttttt
3                        x  x    x
         HaeIII  aaattatttaaaaaaaaaaatattttttatattttttt PCR     ?aataaaaaaaaaatattttaataaaataaaaaaaaaaaaataaaaataaaaaaaatattttaaaaat....
4                                                                                   x
         HaeIII  aaataaaaaaaaaatattttaataaaataaaaaaaaaaaaataaaaataaaaaaaattttttaaaaat...
```

Fig.3B.

| NO. REPEAT UNITS | | | |
|---|---|---|---|
| PCR | HaeIII⁺ | HaeIII⁻ | % |
| a | 1552 | 1 | 72.9 |
| t | 0 | 543 | 25.5 |
| o | 19 | 14 | 1.6 |

Fig.3C.

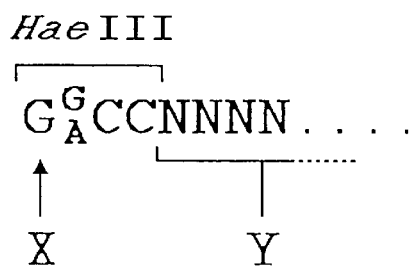

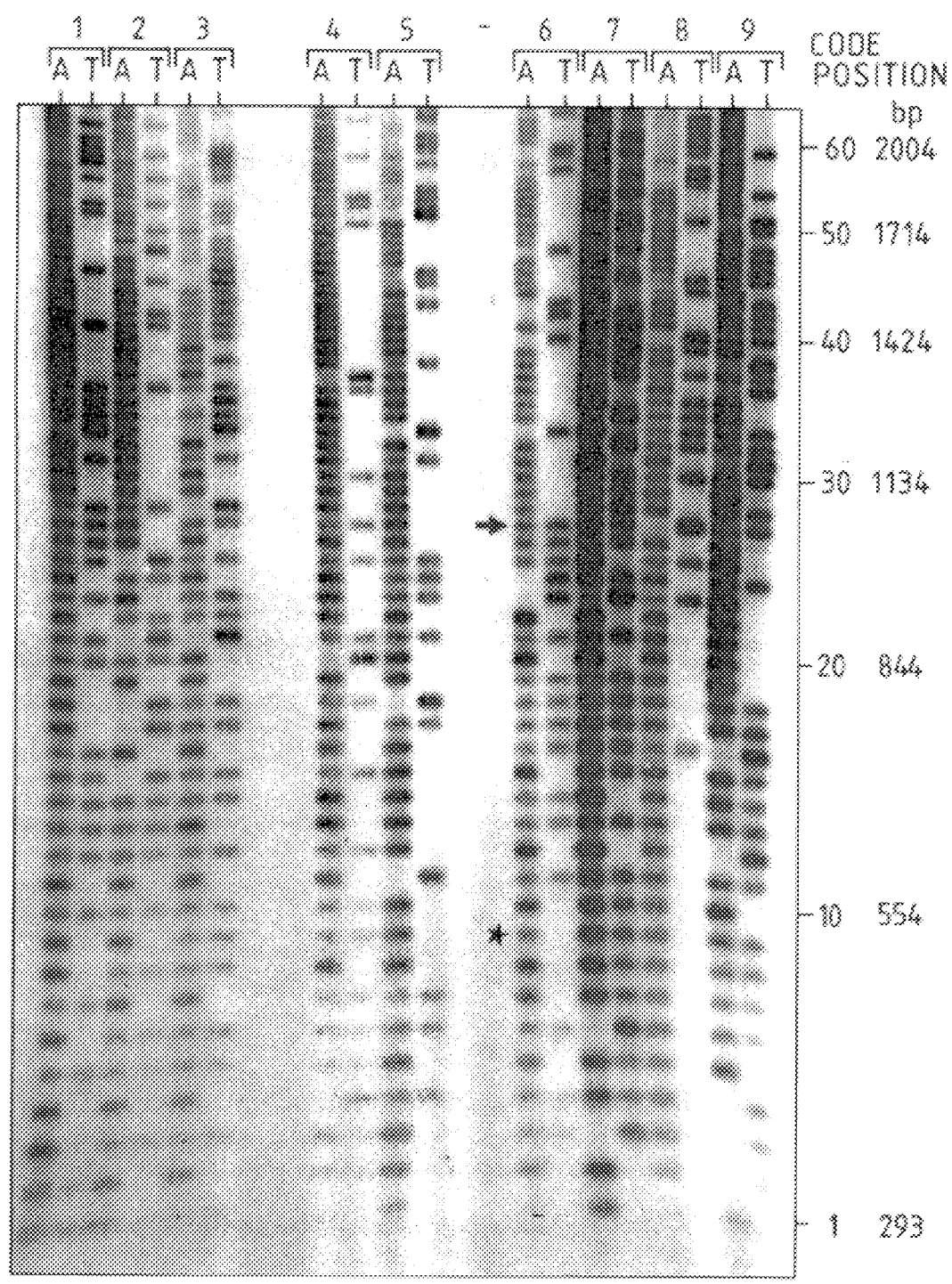

Fig.5C.

Most similar :

```
              10        20        30        40        50        60
              .         .         .         .         .         .
English   41323332231133111111131111111111111111111111111131111133
          : x  xx         x                                    x  xx
Mormon    113222332231323111111131111111111111111111111111111111111

English   111313111113131113131333313131113111111131113111
          x xx  x x                  x  x  x  x
Japanese  11111311111111133131333313111111133131311111131111111
```

Most different :

```
English   331111323334131413335333413153332131133331432313113
          xxxxxxxxxx:xxx:xxxxxxxx:x:xxxxxxx:x:xxxxxx::x
Japanese  22333313121122313244645464454644444554444454544444

English   331111313133111311131323333231131133311112131313332231213113111
          xxxxxxxxxxxxxxxxxxxxx:xx:x:xxxxxxxxxx:::xxx::xxx:xx:x::xxxxxx::xx:x:::
Japanese  22333313121122313244645464454644444554444454544444
```

Fig. 7.

MVR code

| Individual | alleles | 5 | 10 | 15 | 20 | 25 | 30 | 35 | 40 | 45 | 50 | 55 | 60 | 65 | 70 |
|---|---|---|---|---|---|---|---|---|---|---|---|---|---|---|---|
| 1. Single child | | | | | | | | | | | | | | | |
| father | A B | 11111 | 13131 | 11133 | 12131 | 31333 | 33311 | 13111 | 11131 | 11113 | 11113 | 11113 | 11513 | 33311 | 1111.. |
| mother | C D | 11113 | 11111 | 31123 | 14331 | 41311 | 41334 | 13143 | 31133 | 11311 | 11111 | 11313 | 11111 | 11113 | 3133.. |
| child | A C | 11113 | 11111 | 31123 | 13331 | 31233 | 33131 | 13113 | 31123 | 11313 | 11113 | 11312 | 11313 | 33313 | 3113.. |
| allele A | | ?aaaaa | aaaaa | aaat? | ata?a | tattt | ttaaa | a?aaa | aaata | aaaat | aaaat | aaaat | aatat | tttaa | aaaa... |
| allele B | | ?aaaaa | atata | aaaa? | ata?a | aaaaa | aataa | a?aaa | aaaaa | aaaaa | aaaaa | aaaaa | aa0aa | aaaaa | aaaa... |
| allele C | | ?aaaat | aaaaa | taat? | aat?a | aataa | aaata | a?aat | taatt | aataa | aaaaa | aatat | aaaaa | aaaat | taat... |
| allele D | | ?aaaaa | aaaaa | aaat? | a0a?a | 0aaaa | 0ata0 | a?a0a | aaaaa | aaaaa | aaaaa | aaaaa | aaaaa | aaaaa | aata... |
| 2. Multiple children | | | | | | | | | | | | | | | |
| father 10401 | A B | 33331 | 33131 | 33123 | 33111 | 11332 | 11333 | 31113 | 23131 | 22331 | 33133 | 11311 | 21111 | 32333 | 1231.. |
| mother 10402 | C D | 11233 | 23251 | 14331 | 15112 | 35555 | 55454 | 55555 | 55666 | 66666 | 66666 | 66666 | 66666 | 66666 | 6666.. |
| children: | | | | | | | | | | | | | | | |
| 10406,7,11,12 | A C | 11313 | 31331 | 31321 | 13113 | 34445 | 44544 | 44444 | 54454 | 55554 | 44454 | 44444 | 54444 | 45444 | 4544.. |
| 10408 | A D | 11331 | 33341 | 04131 | 14113 | 13332 | 33331 | 33333 | 23454 | 55554 | 44454 | 44444 | 54444 | 45444 | 4544.. |
| 10404,5 | B C | 33233 | 23321 | 13323 | 32113 | 34555 | 44455 | 54445 | 55444 | 55444 | 55445 | 44544 | 54444 | 55555 | 4554.. |
| 10409,10 | B D | 33221 | 22351 | 15133 | 35113 | 13222 | 33123 | 23332 | 22444 | 55444 | 55445 | 44544 | 54444.. | | |
| allele A | | ?aaaaa | aaaaa | taata | aaaaa | aaaat | aataa | aaaaa | taata | ttttta | aaata | aaaaa | taaaa | ataaa | ataa.. |
| allele B | | ?tttta | ttata | atatt | ttaaa | aattt | aaatt | taaat | ttaaa | ttaaa | ttaat | aataa | taaaa | ttttt | atta.. |
| allele C HaeIII map | | ?aatat | tatta | aatta | ataat | t0000 | 00000 | 00000 | 00000 | 00000 | 00000 | 00000 | 00000 | 00000 | 0000.. |
| allele D HaeIII map | | aaatat | tatta | aatta | ataat | t | | | | | | | | | |
| | | ?aatta | ttt0a | a0aaa | a0aat | atttt | ttata | ttttt | tt000 | 00000 | 00000 | 00000 | 00000 | 00000 | 0000.. |
| | | aaatta | tttaa | aaaaa | aaaat | atttt | ttata | ttttt | tt | | | | | | |

Fig. 8.

A. Allele frequencies:

| no. different alleles | no. times observed in sample of 254 alleles |
|---|---|
| 243 | 1 |
| 4 * | 2 |
| 1 | 3 |

B. Examples of indistinguishable alleles:

French   ?aaataaaaatattattatttattaataaaaataataaaaaataaaaaaaa..

Mormon   ?aaataaaaatattattatttattaataaaaataataaaaaataaaaaaaa..

English  ?aaataa?aaatatattatt?attaataaaaaaa?aaaaaaaa?aataaa...

C. Examples of similar alleles:

Mormon   ?aaataaaaatattattatttattaataaaaataataaaaaataaaaaaaa..
         x  x

English  ?taaaaaaatattattatttattaataaaaataataaaaaataaaaaaaaaa..

Mormon   ?aaaatatatttataaaatattattatatataaaatataataattaa0aaaaaa..
         x  x  xxx                                  x   x Mormon   ?taaaaataaaaataattattatataaaatatataaaaataataaaaaaatt..

Fig. 9.

1. Mutation mapping in pedigrees

| Individual | alleles | MVR code |
| --- | --- | --- |
| | | 5   10   15   20   25   30   35   40   45   50   55   60 |
| father 141601 | A B | 3133313111223313321121311311313113333111222311111.. |
| mother 141602 | C D | 2143332133333333311133313331311111113111131111311.. |
| allele A | | ?taaaaataaattaaatataatatatataat0atatttaaattaaaaaa... |
| allele B | | ?aatttaaaaatttaattaataaaaaaaaattaaaaaaattaaaaa... |
| allele C | | ?taataataaattaaaaaaaaaaaataaaaaaataataaaataaaataa... |
| allele D | | ?ta0atttattaattaaattattaaaaaaaaaaaaaaaaaaaaaa... |

| child 141606 | mutant, C | 2113112111331133331111133331132131111111113111321111331.. |
| --- | --- | --- |
| exclusions: | | p      p     e     e    p     e  p | deduced mutant allele
| allele C | | ?taataataaattaaaaaaaaaaaaaataataaaataaaataa.. |

| allele A | | ?taaaataaaattaaatttaattaataaaaaaaattaaaaata.. |

| allele A | | ?taaaaataaattaaatataatatatataat0atatttaaattaaaaaa.. |
| | | xxxx |
| allele B | | ?aatttaaaatttaattaataataataat0atatttaataaaaaaaaaatttaaaaa.. |

Fig.9(cont.)

2. Frequency of mutations

| mutation | CEPH individual | change in repeat unit copy no. | detected on Southern blot | mechanism |
|---|---|---|---|---|
| maternal | | | | |
| a | 134505 | +1 | − | intra-allelic? |
| b | 134606 | +1 | − | intra-allelic? |
| c | 140808 | +? | + | ? |
| d | 142106 | +1 | − | intra-allelic |
| paternal | | | | |
| e | 141606 | +13 | + | inter-allelic |
| f | 142409 | +3 | + | inter-allelic |
| g | 1329405 | +2 | + | ? | mutation rate = 7/572 per gamete = 0.0122   (95% confidence limits 0.006−0.023)

3. Location of presumptive exchange points

```
                       repeat position
             5    10   15   20   25   30   35   40   45   50   55   60
mutation     .    .    .    .    .    .    .    .    .    .    .    .
Donor
    a   xxxxxxxxx
    b   x
    d              xxxxxxxxxx
    e                   xxxx
    f   x
    g     xxxxx
        ?NNNNNNNNNNNNNNNNNNNNNNNNNNNNNNNNNNNNNNNNNNNNNNNNNNNNNNNNN..
Recipient
    a   xxxxxxxxxx
    b   x
    d                  xxxxxxxxxxx
    e     xxx
    f   x
    g     xxxx
``` no. exclusions in first 50 repeats

Fig. 14B.

Group 1

Mormon    ?aaaaaaaataaaaaatAAAAAAAAATAAAAATTAATTAATAAAATTTAAAATATATAAT......
French    ?aaaaaaaaaaaaaataaaaAAAAAAAAATAAAAATTAATTAATAAAATTTAAAATATATTATTAA......
British              ?aaaaaatAAAAAAAAAAATAAAAATTA?TTAAATAA-ATTTAAAAT?TTATAA?TTTT......
British              ?aaaaaatAAAAAAAAAAATA?AAAATTAAT?AAATAAAATT?AAAATATATATAAT??T......
Mormon                   ?atttttaAAAAAAAAAA?AAAATTAAT?AAATAAATTAATTAAAATTATTAAATTTT......
British                            ?aatAAAAAAAAATAAAAATTAATT?AATAAAAT??TAAAATATTATTAAATTTT......

Group 2

Mormon    ?aaataaaaAAAATATTATTATTATTAATAAAAAAAAAAAATAAAA......
British      ?aaaataaaAAAATATTATTATTAT?AATAAAAAA?ATAAAAAAAAaataaaa?aa?aaataaaa......
French         ?aaataaaAAAATATTATTATTAT?AATAATAAAAAAAAAATATAAAAAAAAAAA......
Mormon         ?aaataaaAAAATATTATTATTAATAATAAAaAAAAAATATAAAAAAAAAAAA......
British        ?aaataaaAAAATAA-TATTATTTATTAATAAAAAAAAAATATAAAAAAAAAAA......
Mormon              ?AAATATTATTATTATTAATAAAAAAAAAATAAAAAAAAAAAAAAAA......

Group 3

British   ??aa?0a?aaaa?ae0ataAAAATTT?A?AA0ATAAAATAATAAAAAAA?TTAATA0ATA0A......
French      ?aaataa0ataAAAATTTAATAAATTT?A0ATAAAATAATA0ATA0ATA0RTA0RA......
British      ?ataaaat??AAAA?TTA??AA0ATA?AA0ATAAAATAATAAAAAAA?TTAATA0ATA0ATA0AA0A0A......
French               ?aaAAAAATTTAATA?AA0ATAAAATAATAAAATTTAATA0ATAAAATA0ATA0AA0A0ATA......
French                ?aAAAATTTAATA0ATAAAATAATAAAATTTAATA0ATAAAATA0ATA0AAAA0A......
British                 ?AAAAT??AATAA0ATAAAATAAAAATTAATAAATT?AA?AA0A?A0ATA?A......

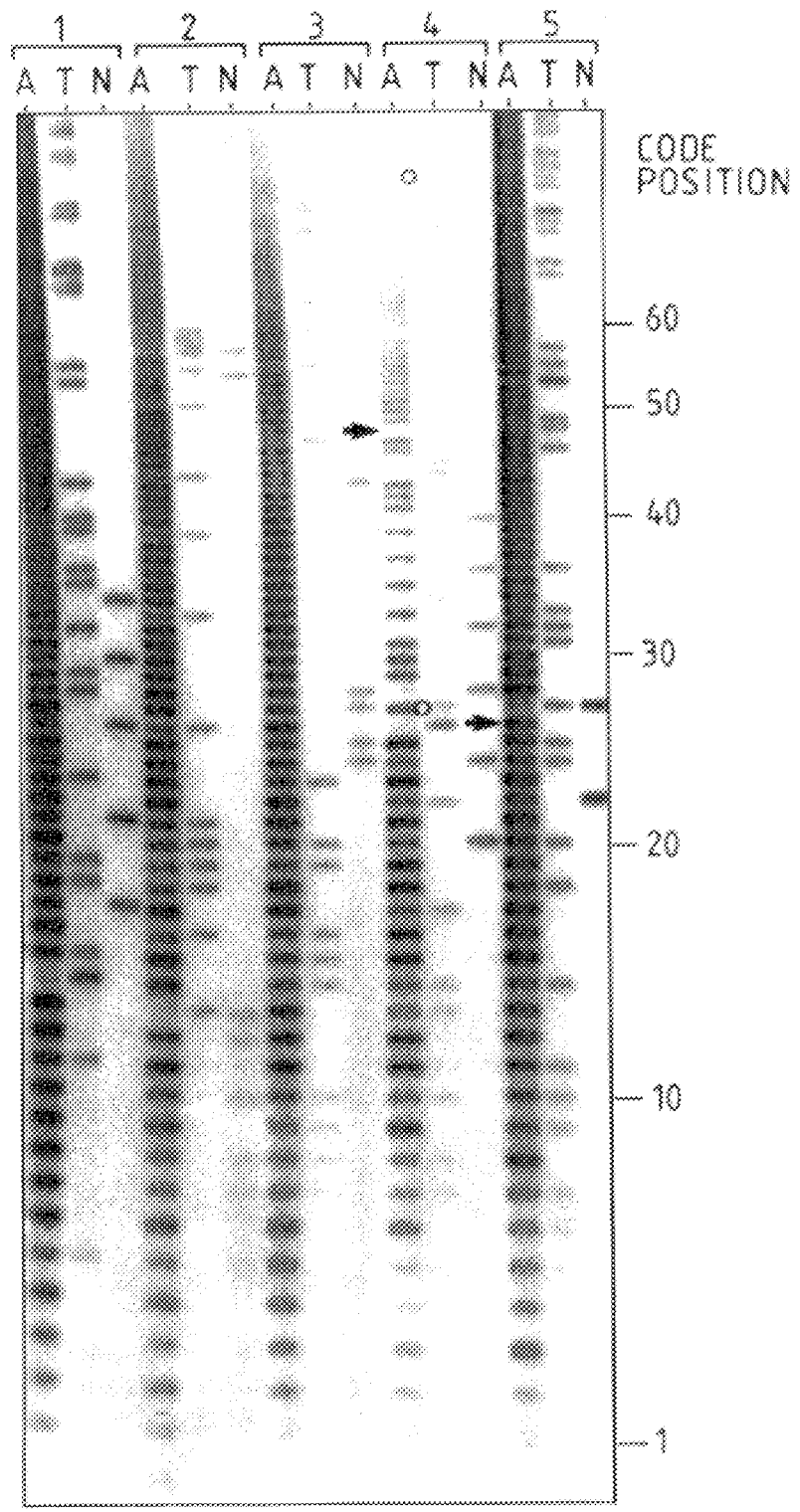

```
English  aaaaaaNaaaaNaaNaaaNaaNataNataNataNataNaaattaa......
English  aaaaaaaaaaaaaaaaa?aaaaaaaaaaaaUUUUUUNaNNaaaaaaaaaaaaaa..
```

Fig. 19.

Group A

```
 1 English   ?aa?Na?aAAA?AAAA?AANATAAAAATTT?A?AANATAAAAAAATAAAAAAAA?TTAATAANATANA................>
 2 French              AATAANATAAAAATTTAATAANATAAAAAAATAAAAAAATAAAAAAATTAATAANATANATANAAA..............
 3 English                    ataaaat??AAAA?TTA??AANATAAAAAAATAAAAAAATAAAAAAA?TTAATAANATANTANATANANAAANANAAA.........
 4 French                          aaAAAAATTTAATAANATAAAAAAATAAAAAAATAAAAAAATTAATAANATAaaaataaaaatttaa...
 5 French                              AAAAATTTAATAANATAAAAAAATAAAAAAATTTAATAANATAAANATANANAAAAAAAAA..
 6 French                                        aaataaaaataaaataaaATAAAAAAATAAAAAAATTAATAANATAaaaaaaaaat..........
                                                   +     +     +     +     +     +     +     +    +    +
```

Group B

```
 7 Mormon    ataaaaaaataaaatataattatttaatTTAATAATAANATAANATANAAANATANATANAAA..................
 8 Mormon            attaaaatatttaAATTAATAANATAANATAANATAANATANAAANATANAAATTAAAAAAATAAAAAAAAAA.........
 9 Japanese               aaattattaTAATTAATAANATAANATAANATAANATANAAANATAAATTAAUAAAAAAAAAATAAAAAAAAATT...........
10 Japanese                       tTAATTAATAANATAANATAANATAANATANAAANATANATAAANATAAAAAATTAAAAAAAAAAATTATTT.
                                   +      +     +     +     +     +     +     +    *
```

Group C

```
11 French    aaaaataattTTAATAATAANATAANATAANATAATTTATAATAATATTTAAATTTAAATTTAAAT.................
12 English   aaaaaaaaaAATAATAATAATAANATAATAATAATTTTATAATAATAATATTTAAATTTAAATTTAA................
13 French    aaaaaaaTAATAATAATAATAATAATAATAATAATTTATAATAATAATATTTAAATTTAAATTAAATTTAAATTTAA..........
14 Mormon    aataaaaATAATAATAATAATAATAATAATAATAATTTATAATAATAATATTTAAATTTAAATTTAAATTTAAATT..........
15 Bangladeshi   ttaaatattaaatATAATAATAATAATAATAATAATAATAATTTATAATAATAATTTAAATTTAAATTTAAATTTAAAAATA.......
16 Mormon        attaaattaataaAATAATAATTTATAATAATAATTTATAATTTAAATTTAAATTTAAATTTAAAATAAA......+.........
17 English                    T??AAATTTAAAT?TA?ATTTAAATTTAAAATAAATTTA?TTAATTAAA..........
18 English                      ataUatATT?AAATT?AAAAA?AAATTTAA??AATTTAA?2AATTAAATAA.
                                   *
```

No. exclusions in first 50 repeat units

Fig. 23.

```
                   1        10        20        30        40        50        60        70
                   |         .         .         .         .         .         .         .
Human Clone        TAAGCTCTCCATTCCAGTTTCTGGAAAAATTTGTGTAGAATTTGTGTAAATAAATTTTGGTGCTGCAAAAGAAATAC
Ancestral Sequence NNNNNNNNNNNNNNNNNNNNNNNNNNNNNNNNNNNNNNNNNNNNNNNNNNNNNNNNNNNNNNNNNNNNNNNNNNNN
Human Variant                                                                             G
                                                                                        1 G 81       90        100       110       120       130       140       150
                   |         .         .         .         .         .         .         .
Human Clone        CACTCAAACATAAGTTTAATTTTCTCAGCAAGGCAATTTTACTTCTCTAGAAGGGTGCGACTCGCAGATGGAGCAATGGC
Ancestral Sequence              A                                   A                  T
Human Variant                  2                                  3                  4 T 161      170       180       190       200       210       220       230
                   |         .         .         .         .         .         .         .
Human Clone        CAGAGCACACCTGAACAAGGAGGGGAAGGGGGTTCTGATTCCTGACACAGGTAGCCCCTACTGATGCGTCGTTCCCGTAT
Ancestral Sequence                                           T            G
Human Variant                                              5            6

241      250       260       270       280       290       300       310
                   |         .         .         .         .         .         .         .
Human Clone        CGGCTAGGGTTGGACTGCACAGTCTAAGCTAATTCCGATTGGCTACTTTAAAGAGAGCAGGGTATGAGCCAGAGTGGCG
Ancestral Sequence T                                                                      A
Human Variant    7 T                                                                   8 A
                                                                                        9

321      330       340
                   |         .
Human Clone        GGGTGAGTAGTTTGGTGGGAAGGGTGGT
Ancestral Sequence
Human Variant
```

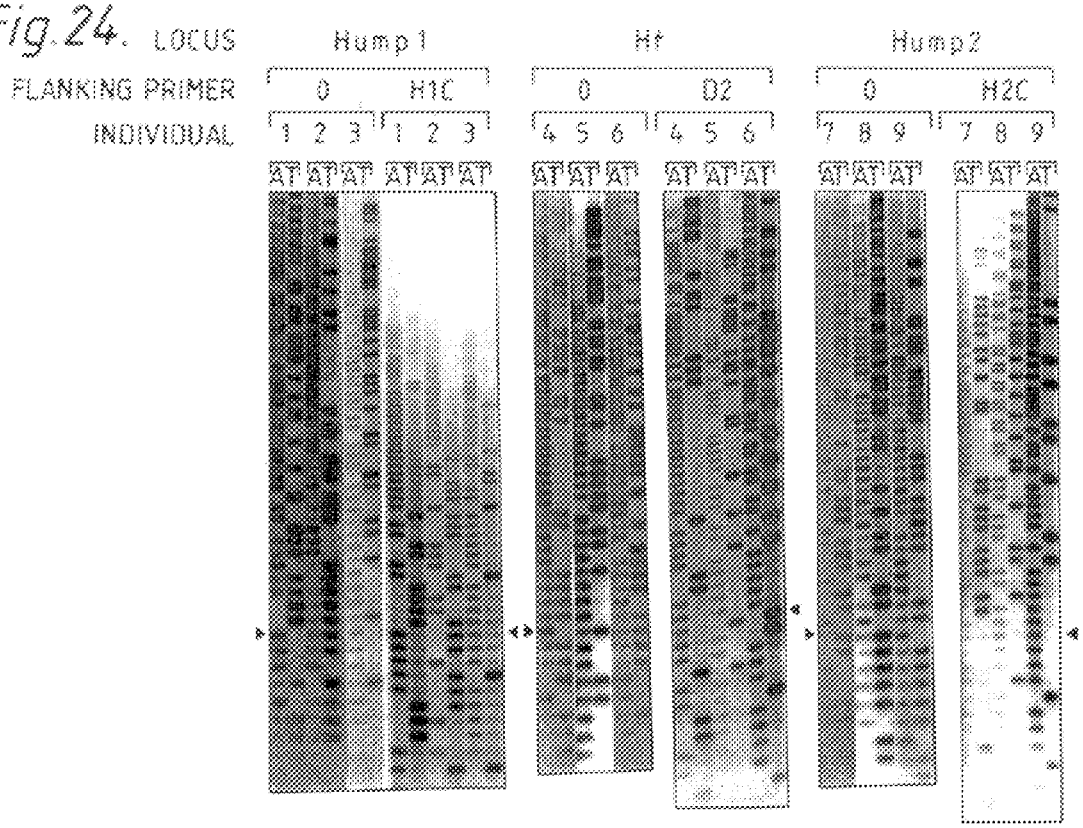

MVR-PCR MAPS OF SINGLE MS31 ALLELES

Fig. 30.

MS31 Allele alignments

| INDIVIDUAL | ALLELE | |
|---|---|---|
| CEPH 133413 | lower | ttaATATATTATTAATAAATGTATTAATTTTTTATATTTTATA-OOOAAAOOOAAOOATTTTAATTTTATTT...... |
| CEPH 1329212 | lower | taaatATATATTATTAAATGTATTAATT--TTATATTTTATA-OOOAAAOOOAAOOATTTTAATTTTATTT...... |
| CEPH 6602 | lower | ?ttatattataattATATATTATTAAATGTATTAATTTTTTATATTT-ATATOOOAAAOOOAAOOATTTTAATTTTATTT...... |

FIGURE 38
Homotagged Primer Dimer
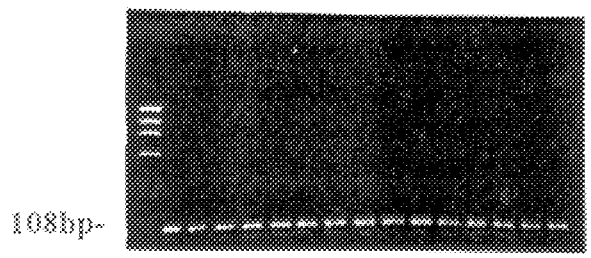
108bp-
Heterotagged PD 2
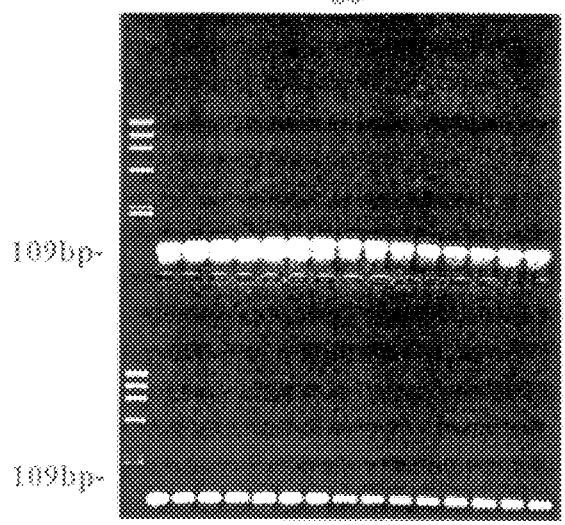
109bp-
109bp-
Heterotagged PD 3

SEQUENCE LISTING ( 1 ) GENERAL INFORMATION:

( i i i ) NUMBER OF SEQUENCES: 57

( 2 ) INFORMATION FOR SEQ ID NO:1:

( i ) SEQUENCE CHARACTERISTICS:
        ( A ) LENGTH: 15 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:1:

GCAGATGGAG CAATG    15

( 2 ) INFORMATION FOR SEQ ID NO:2:

( i ) SEQUENCE CHARACTERISTICS:
        ( A ) LENGTH: 15 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:2:

TGAGTCACCC CTGGC    15

( 2 ) INFORMATION FOR SEQ ID NO:3:

( i ) SEQUENCE CHARACTERISTICS:
        ( A ) LENGTH: 15 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:3:

TGAGTCACCC CTGGT    15

( 2 ) INFORMATION FOR SEQ ID NO:4:

( i ) SEQUENCE CHARACTERISTICS:
        ( A ) LENGTH: 18 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:4:

GCAGATGGAG CAATGGCC    18

( 2 ) INFORMATION FOR SEQ ID NO:5:

( i ) SEQUENCE CHARACTERISTICS:
        ( A ) LENGTH: 19 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:5:

TTTGGTGCTG AAAAGAAAG    19

( 2 ) INFORMATION FOR SEQ ID NO:6:

( i ) SEQUENCE CHARACTERISTICS:
        ( A ) LENGTH: 19 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:6:

AGGTGGAGGG TGTCTGTGA 19

( 2 ) INFORMATION FOR SEQ ID NO:7:

( i ) SEQUENCE CHARACTERISTICS:
        ( A ) LENGTH: 19 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:7:

GGGTGGAGGG TGTCTGTGA 19

( 2 ) INFORMATION FOR SEQ ID NO:8:

( i ) SEQUENCE CHARACTERISTICS:
        ( A ) LENGTH: 20 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:8:

AGGCCTGGTA CCTGCGTACT 20

( 2 ) INFORMATION FOR SEQ ID NO:9:

( i ) SEQUENCE CHARACTERISTICS:
        ( A ) LENGTH: 20 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:9:

ACCCACCTCC CACAGACACT 20

( 2 ) INFORMATION FOR SEQ ID NO:10:

( i ) SEQUENCE CHARACTERISTICS:
        ( A ) LENGTH: 20 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:10:

GTCCACCTCC CACAGACACT 20

( 2 ) INFORMATION FOR SEQ ID NO:11:

( i ) SEQUENCE CHARACTERISTICS:
        ( A ) LENGTH: 20 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:11:

GCGACCGGTC GCCGGACGCC 20

( 2 ) INFORMATION FOR SEQ ID NO:12:

( i ) SEQUENCE CHARACTERISTICS:
        ( A ) LENGTH: 20 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:12:

```
          CATTCTGAGT CACCCCTGGT                                              20
```

( 2 ) INFORMATION FOR SEQ ID NO:13:

( i ) SEQUENCE CHARACTERISTICS:
        ( A ) LENGTH: 20 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:13:

```
          CATTCTGAGT CACCCCTGGC                                              20
```

( 2 ) INFORMATION FOR SEQ ID NO:14:

( i ) SEQUENCE CHARACTERISTICS:
        ( A ) LENGTH: 20 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:14:

```
          TGGTGCTGCA AAAGAAATAC                                              20
```

( 2 ) INFORMATION FOR SEQ ID NO:15:

( i ) SEQUENCE CHARACTERISTICS:
        ( A ) LENGTH: 20 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:15:

```
          AGTAGCCAAT CGGAATTAGC                                              20
```

( 2 ) INFORMATION FOR SEQ ID NO:16:

( i ) SEQUENCE CHARACTERISTICS:
        ( A ) LENGTH: 20 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:16:

```
          TGATGCGTCG TTCCCGTATC                                              20
```

( 2 ) INFORMATION FOR SEQ ID NO:17:

( i ) SEQUENCE CHARACTERISTICS:
        ( A ) LENGTH: 20 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:17:

```
          CCCCACACCG GCACACCGTC                                              20
```

( 2 ) INFORMATION FOR SEQ ID NO:18:

( i ) SEQUENCE CHARACTERISTICS:
        ( A ) LENGTH: 20 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:18:

```
          GGACAGCCAA GGCCAGGTCC                                              20
```

( 2 ) INFORMATION FOR SEQ ID NO:19:

( i ) SEQUENCE CHARACTERISTICS:
        ( A ) LENGTH: 20 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:19:

CCACTCGGAA CCACCTGCAG     20

( 2 ) INFORMATION FOR SEQ ID NO:20:

( i ) SEQUENCE CHARACTERISTICS:
        ( A ) LENGTH: 20 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:20:

GGAGGGGCCA TGAAGGGGAC     20

( 2 ) INFORMATION FOR SEQ ID NO:21:

( i ) SEQUENCE CHARACTERISTICS:
        ( A ) LENGTH: 20 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:21:

CATGAAGGGG ACTGGCCTTA     20

( 2 ) INFORMATION FOR SEQ ID NO:22:

( i ) SEQUENCE CHARACTERISTICS:
        ( A ) LENGTH: 20 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:22:

CATGAAGGGG ACTGGCCTTG     20

( 2 ) INFORMATION FOR SEQ ID NO:23:

( i ) SEQUENCE CHARACTERISTICS:
        ( A ) LENGTH: 21 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:23:

GTGCAGTCCC AACCCTAGCC A     21

( 2 ) INFORMATION FOR SEQ ID NO:24:

( i ) SEQUENCE CHARACTERISTICS:
        ( A ) LENGTH: 21 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:24:

CGACTCGCAG ATGGAGCAAT G     21

( 2 ) INFORMATION FOR SEQ ID NO:25:

( i ) SEQUENCE CHARACTERISTICS:
        ( A ) LENGTH: 24 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:25:

CGACTCGCAG ATGGAGCAAT GGCC                           24

( 2 ) INFORMATION FOR SEQ ID NO:26:

( i ) SEQUENCE CHARACTERISTICS:
        ( A ) LENGTH: 24 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:26:

GAGTAGTTTG GTGGGAAGGG TGGT                           24

( 2 ) INFORMATION FOR SEQ ID NO:27:

( i ) SEQUENCE CHARACTERISTICS:
        ( A ) LENGTH: 24 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:27:

CCCTTTGCAC GCTGGACGGT GGCG                           24

( 2 ) INFORMATION FOR SEQ ID NO:28:

( i ) SEQUENCE CHARACTERISTICS:
        ( A ) LENGTH: 24 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:28:

CCCACACGCC CATCCGGCCG GCAG                           24

( 2 ) INFORMATION FOR SEQ ID NO:29:

( i ) SEQUENCE CHARACTERISTICS:
        ( A ) LENGTH: 24 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:29:

GGCACAACCT AGGCAGGGGA AGCC                           24

( 2 ) INFORMATION FOR SEQ ID NO:30:

( i ) SEQUENCE CHARACTERISTICS:
        ( A ) LENGTH: 25 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:30:

TAAGCTCTCC ATTTCCAGTT TCTGG                         25

( 2 ) INFORMATION FOR SEQ ID NO:31:

( i ) SEQUENCE CHARACTERISTICS:
: ( A ) LENGTH: 29 Base Pairs
: ( B ) TYPE: Nucleic Acid
: ( C ) STRANDEDNESS: Single
: ( D ) TOPOLOGY: Linear ( x i ) SEQUENCE DESCRIPTION: SEQ ID NO:31:

GGCCAGGGGT GACTCAGAAT GGAGCAGGY 29

( 2 ) INFORMATION FOR SEQ ID NO:32:

( i ) SEQUENCE CHARACTERISTICS:
: ( A ) LENGTH: 29 Base Pairs
: ( B ) TYPE: Nucleic Acid
: ( C ) STRANDEDNESS: Single
: ( D ) TOPOLOGY: Linear ( x i ) SEQUENCE DESCRIPTION: SEQ ID NO:32:

GACCAGGGGT GACTCAGAAT GGAGCAGGY 29

( 2 ) INFORMATION FOR SEQ ID NO:33:

( i ) SEQUENCE CHARACTERISTICS:
: ( A ) LENGTH: 29 Base Pairs
: ( B ) TYPE: Nucleic Acid
: ( C ) STRANDEDNESS: Single
: ( D ) TOPOLOGY: Linear ( x i ) SEQUENCE DESCRIPTION: SEQ ID NO:33:

GRCCNGGGGT GACTCAGAAT GGACGAGGY 29

( 2 ) INFORMATION FOR SEQ ID NO:34:

( i ) SEQUENCE CHARACTERISTICS:
: ( A ) LENGTH: 29 Base Pairs
: ( B ) TYPE: Nucleic Acid
: ( C ) STRANDEDNESS: Single
: ( D ) TOPOLOGY: Linear ( x i ) SEQUENCE DESCRIPTION: SEQ ID NO:34:

GGTCAGGGGT GACTCAGAAT GGAGCAGGY 29

( 2 ) INFORMATION FOR SEQ ID NO:35:

( i ) SEQUENCE CHARACTERISTICS:
: ( A ) LENGTH: 38 Base Pairs
: ( B ) TYPE: Nucleic Acid
: ( C ) STRANDEDNESS: Single
: ( D ) TOPOLOGY: Linear ( x i ) SEQUENCE DESCRIPTION: SEQ ID NO:35:

AGGTGGAGGG TGTCTGTGAG GCCTGGTACC TGCGTACT 38

( 2 ) INFORMATION FOR SEQ ID NO:36:

( i ) SEQUENCE CHARACTERISTICS:
: ( A ) LENGTH: 38 Base Pairs
: ( B ) TYPE: Nucleic Acid
: ( C ) STRANDEDNESS: Single
: ( D ) TOPOLOGY: Linear ( x i ) SEQUENCE DESCRIPTION: SEQ ID NO:36:

GGGTGGAGGG TGTCTGTGAG GCCTGGTACC TGCGTACT 38

( 2 ) INFORMATION FOR SEQ ID NO:37:

( i ) SEQUENCE CHARACTERISTICS:
: ( A ) LENGTH: 38 Base Pairs ( B ) TYPE: Nucleic Acid
( C ) STRANDEDNESS: Single
( D ) TOPOLOGY: Linear ( x i ) SEQUENCE DESCRIPTION: SEQ ID NO:37:

TCACCGGTGA ATTCACCACC CTTCCCACCA AACTACTC  38

( 2 ) INFORMATION FOR SEQ ID NO:38:

( i ) SEQUENCE CHARACTERISTICS:
( A ) LENGTH: 39 Base Pairs
( B ) TYPE: Nucleic Acid
( C ) STRANDEDNESS: Single
( D ) TOPOLOGY: Linear ( x i ) SEQUENCE DESCRIPTION: SEQ ID NO:38:

GCGACCGGTC GCCGGACGCC TTTTCATAAT CACAAAAAT  39

( 2 ) INFORMATION FOR SEQ ID NO:39:

( i ) SEQUENCE CHARACTERISTICS:
( A ) LENGTH: 40 Base Pairs
( B ) TYPE: Nucleic Acid
( C ) STRANDEDNESS: Single
( D ) TOPOLOGY: Linear ( x i ) SEQUENCE DESCRIPTION: SEQ ID NO:39:

TCATGCGTCC ATGGTCCGGA CATTCTGAGT CACCCCTGGC  40

( 2 ) INFORMATION FOR SEQ ID NO:40:

( i ) SEQUENCE CHARACTERISTICS:
( A ) LENGTH: 40 Base Pairs
( B ) TYPE: Nucleic Acid
( C ) STRANDEDNESS: Single
( D ) TOPOLOGY: Linear ( x i ) SEQUENCE DESCRIPTION: SEQ ID NO:40:

TCATGCGTCC ATGGTCCGGA CATTCTGAGT CACCCCTGGT  40

( 2 ) INFORMATION FOR SEQ ID NO:41:

( i ) SEQUENCE CHARACTERISTICS:
( A ) LENGTH: 40 Base Pairs
( B ) TYPE: Nucleic Acid
( C ) STRANDEDNESS: Single
( D ) TOPOLOGY: Linear ( x i ) SEQUENCE DESCRIPTION: SEQ ID NO:41:

TCATGCGTCC ATGGTCCGGA TCCATTCTGA GTCACCCCGG  40

( 2 ) INFORMATION FOR SEQ ID NO:42:

( i ) SEQUENCE CHARACTERISTICS:
( A ) LENGTH: 40 Base Pairs
( B ) TYPE: Nucleic Acid
( C ) STRANDEDNESS: Single
( D ) TOPOLOGY: Linear ( x i ) SEQUENCE DESCRIPTION: SEQ ID NO:42:

TCATGCGTCC ATGGTCCGGA CCATTCTGAG TCACCCCTGA  40

( 2 ) INFORMATION FOR SEQ ID NO:43:

( i ) SEQUENCE CHARACTERISTICS:
( A ) LENGTH: 42 Base Pairs
( B ) TYPE: Nucleic Acid
( C ) STRANDEDNESS: Single (D) TOPOLOGY: Linear (x i) SEQUENCE DESCRIPTION: SEQ ID NO:43:

GCGACCGGTC GCCGGACGCC AAATAGGACA ACTAAAATAT TT    42

(2) INFORMATION FOR SEQ ID NO:44:

(i) SEQUENCE CHARACTERISTICS:
        (A) LENGTH: 50 Base Pairs
        (B) TYPE: Nucleic Acid
        (C) STRANDEDNESS: Single
        (D) TOPOLOGY: Linear (x i) SEQUENCE DESCRIPTION: SEQ ID NO:44:

GCGACCGGTC GCCGGACGCC GGCTGATTCT GAAGATAAAC TAGAACCCGA    50

(2) INFORMATION FOR SEQ ID NO:45:

(i) SEQUENCE CHARACTERISTICS:
        (A) LENGTH: 52 Base Pairs
        (B) TYPE: Nucleic Acid
        (C) STRANDEDNESS: Single
        (D) TOPOLOGY: Linear (x i) SEQUENCE DESCRIPTION: SEQ ID NO:45:

GCGACCGGTC GCCGGACGCC GAAATAAAAG AAAAGATTGG AACTAGGTCA GC    52

(2) INFORMATION FOR SEQ ID NO:46:

(i) SEQUENCE CHARACTERISTICS:
        (A) LENGTH: 80 Base Pairs
        (B) TYPE: Nucleic Acid
        (C) STRANDEDNESS: Single
        (D) TOPOLOGY: Linear (x i) SEQUENCE DESCRIPTION: SEQ ID NO:46:

TAAGCTCTCC ATTTCCAGTT TCTGGAAAAA TTTGTGTAGA ATTTGTTGTA AATAAATTTT    60

TGGTGCTGCA AAAGAAATAC    80

(2) INFORMATION FOR SEQ ID NO:47:

(i) SEQUENCE CHARACTERISTICS:
        (A) LENGTH: 80 Base Pairs
        (B) TYPE: Nucleic Acid
        (C) STRANDEDNESS: Single
        (D) TOPOLOGY: Linear (x i) SEQUENCE DESCRIPTION: SEQ ID NO:47:

NNNNNNNNN NNNNNNNNN NNNNNNNNN NNNNNNNNN ATTTGTTGTA AATAAATTTT    60

TGGTGCTGCA AAAGAAATAG    80

(2) INFORMATION FOR SEQ ID NO:48:

(i) SEQUENCE CHARACTERISTICS:
        (A) LENGTH: 80 Base Pairs
        (B) TYPE: Nucleic Acid
        (C) STRANDEDNESS: Single
        (D) TOPOLOGY: Linear (x i) SEQUENCE DESCRIPTION: SEQ ID NO:48:

TAAGCTCTCC ATTTCCAGTT TCTGGAAAAA TTTGTGTAGA ATTTGTTGTA AATAAATTTT    60

TGGTGCTGCA AAAGAAATAG    80

(2) INFORMATION FOR SEQ ID NO:49:

( i ) SEQUENCE CHARACTERISTICS:
　　　　( A ) LENGTH: 80 Base Pairs
　　　　( B ) TYPE: Nucleic Acid
　　　　( C ) STRANDEDNESS: Single
　　　　( D ) TOPOLOGY: Linear ( x i ) SEQUENCE DESCRIPTION: SEQ ID NO:49:

CACTCAAACA TAAGTTTAAT TTTCTCAGCA AGGCAATTTT ACTTCTCTAG AAGGGTGCGA　　60

CTCGCAGATG GAGCAATGGC　　80

( 2 ) INFORMATION FOR SEQ ID NO:50:

( i ) SEQUENCE CHARACTERISTICS:
　　　　( A ) LENGTH: 80 Base Pairs
　　　　( B ) TYPE: Nucleic Acid
　　　　( C ) STRANDEDNESS: Single
　　　　( D ) TOPOLOGY: Linear ( x i ) SEQUENCE DESCRIPTION: SEQ ID NO:50:

CACTCAAACA TAAATTTAAT TTTCTCAGCA AGGCAATTTT ACTTCTATAG AAGGGTGCGA　　60

CTTGCAGATG GAGCAATGGC　　80

( 2 ) INFORMATION FOR SEQ ID NO:51:

( i ) SEQUENCE CHARACTERISTICS:
　　　　( A ) LENGTH: 80 Base Pairs
　　　　( B ) TYPE: Nucleic Acid
　　　　( C ) STRANDEDNESS: Single
　　　　( D ) TOPOLOGY: Linear ( x i ) SEQUENCE DESCRIPTION: SEQ ID NO:51:

CACTCAAACA TAAGTTTAAT TTTCTCAGCA AGGCAATTTT ACTTCTCTAG AAGGGTGCGA　　60

CTCGCAGATG GAGCAATGGC　　80

( 2 ) INFORMATION FOR SEQ ID NO:52:

( i ) SEQUENCE CHARACTERISTICS:
　　　　( A ) LENGTH: 80 Base Pairs
　　　　( B ) TYPE: Nucleic Acid
　　　　( C ) STRANDEDNESS: Single
　　　　( D ) TOPOLOGY: Linear ( x i ) SEQUENCE DESCRIPTION: SEQ ID NO:52:

CAGAGCACAC CTGAACAAGG GAGGGGAAGG GGTTCTGATT CCTGACACAG GTAGCCCCTA　　60

CTGATGCGTC GTTCCCGTAT　　80

( 2 ) INFORMATION FOR SEQ ID NO:53:

( i ) SEQUENCE CHARACTERISTICS:
　　　　( A ) LENGTH: 80 Base Pairs
　　　　( B ) TYPE: Nucleic Acid
　　　　( C ) STRANDEDNESS: Single
　　　　( D ) TOPOLOGY: Linear ( x i ) SEQUENCE DESCRIPTION: SEQ ID NO:53:

CAGAGCACAC CTGAACAAGG GAGGGGAAGG GGTTCTTATT CCTGACGCAG GTAGCCCCTA　　60

CTGATGCGTC GTTCCCGTAT　　80

( 2 ) INFORMATION FOR SEQ ID NO:54:

( i ) SEQUENCE CHARACTERISTICS:
　　　　( A ) LENGTH: 80 Base Pairs
　　　　( B ) TYPE: Nucleic Acid
　　　　( C ) STRANDEDNESS: Single
　　　　( D ) TOPOLOGY: Linear ( x i ) SEQUENCE DESCRIPTION: SEQ ID NO:54:

CGGCTAGGGT TGGACTGCAC AGTCTAAGCT AATTCCGATT GGCTACTTTA AAGAGAGCAG 60

GGGTATGAGC CAGAGTGGCG 80

( 2 ) INFORMATION FOR SEQ ID NO:55:

( i ) SEQUENCE CHARACTERISTICS:
        ( A ) LENGTH: 80 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:55:

TGGCTAGGGT TGGACTGCAC AGTCTAAGCT AATTCCGATT GGCTACTTTA AAGAGAGCAG 60

GGGTATGAAC CAGAGTGGTG 80

( 2 ) INFORMATION FOR SEQ ID NO:56:

( i ) SEQUENCE CHARACTERISTICS:
        ( A ) LENGTH: 80 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:56:

TGGCTAGGGT TGGACTGCAC AGTCTAAGCT AATTCCGATT GGCTACTTTA AAGAGAGCAG 60

GGGTATGAGC CAGAGTGGCG 80

( 2 ) INFORMATION FOR SEQ ID NO:57:

( i ) SEQUENCE CHARACTERISTICS:
        ( A ) LENGTH: 28 Base Pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:57:

GGGTGAGTAG TTTGGTGGGA AGGGTGGT 28

METHOD OF CHARACTERISATION OF GENOMIC DNA

This application is a continuation-in-part of application of Ser. No. 08/418,859 filed Apr. 5, 1995 which is a continuation of 07/935,107, filed Aug. 26, 1992 now abandoned.

The present invention relates generally to a method of characterising a sample of genomic DNA and to nucleotide sequences employed in the method as well as kits comprising these. In particular the invention involves the use of primers which selectively prime specific type(s) of internal repeat unit in a tandemly repeated region. The method of the invention is particularly useful in forensic or paternity studies and provides individual sample codes suitable for computerised storage on, and retrieval from, a database. The invention also relates to databases comprising the individual sample codes and to computers when programmed to use the above sample codes and databases. The invention also provides a novel method for the detection of diagnostic base sequences in one or more nucleic acids contained in a sample.

Hypervariable human DNA markers are capable of identifying individuals with a high degree of specificity and have had a profound impact on forensic and legal medicine, both for providing evidence for associations or exclusions between forensic evidence and criminal suspects, and for establishing kinship in for example paternity disputes. Most of the hypervariable loci used in DNA profiling are tandem-repetitive minisatellite or VNTR (variable number tandem repeat) loci which can show extreme levels of allelic variability in repeat copy number and therefore DNA fragment length (Nakamura et al., 1987b; Wong et al., 1987). Multilocus probes (MLPs) capable of detecting multiple hypervariable minisatellites to produce a DNA fingerprint, and single locus minisatellite probes (SLPs) which reveal allelic length variation at individual hypervariable loci to produce much simpler DNA profiles, have been extensively used in casework (Jeffreys et al., 1985a, 1985b—UK Patent 2166445/Lister Institute, 1991a; Wong et al., 1987—UK Patent 2188323/ICI plc). Amplification of hypervariable loci using the polymerase chain reaction (PCR) has greatly increased the sensitivity of DNA typing systems (Jeffreys et al., 1988; Boerwinkle et al., 1989) and has permitted the development of new classes of variable "microsatellite" DNA markers based on simple tandem repeat loci with very short alleles (Litt and Luty, 1989; Tautz, 1989; Weber and May, 1989).

Despite the power of current DNA typing systems, technical problems have prevented their full potential from being realised. MLPs generate complex multi-band DNA fingerprints from Southern blots of human genomic DNA which have proved to be very effective in determining family relationships (Jeffreys et al., 1985c, 1991a). However, these probes have proved less useful in forensic investigations due to the relative lack of probe sensitivity, difficulties in comparing DNA fingerprints between blots and major problems in converting the complex patterns into a form appropriate for computer databasing (see Jeffreys et al., 1991b). These problems have been largely overcome using the 1–2 band DNA profiles generated by Southern blot analysis with SLPs, but other limitations remain. First, allele lengths at hypervariable loci can vary in a quasi-continuous fashion in human populations, making unequivocal allele identification impossible (Baird et al., 1986; Wong et al., 1987; Balazs et al., 1989; Odelberg et al., 1989; Smith et al., 1990). In addition, variation in electrophoretic mobility between DNA samples will introduce errors in allele length estimates; such "band-shifts" can occasionally lead to apparent exclusions between the DNA profiles of a forensic specimen and a criminal, which can, in general, only be evaluated using empirical statistical information on the magnitude of such sizing errors generated from extensive validation surveys (Lander, 19898; Budowle et al., 1991). More seriously, error-prone allele size estimates impede the comparison of DNA profile evidence gathered from different Southern blots, greatly weakening the statistical power of population and criminal DNA profile databases, and preventing the unambiguous comparison of DNA profile evidence between different forensic laboratories during the course of a criminal investigation. Some PCR-based DNA typing systems can in principle circumvent these problems of error-prone allele sizing. Thus microsatellites and other simple tandem repeat loci generate short PCR-amplifiable alleles which should be classifiable with precision by sizing on DNA sequencing gels against an appropriate sequencing ladder (Litt and Luty, 1989; Weber and May, 1989). However, most of the microsatellite loci, and particularly those based on dinucleotide repeats, show complex multi-band patterns per allele on DNA sequencing gels which appear to arise through Taq polymerase slippage at dinucleotide repeats during amplification (Weber and May, 1989) and through non-templated nucleotide addition catalysed by Taq polymerase (Clark, 1988). As a result, it is sometimes difficult to determine with confidence the true size of a given allele. More seriously, the level of allelic variability at microsatellites is very poor compared with the most variable minisatellites; the most informative CA repeat locus identified to date shows only 12 different length alleles (Litt and Luty, 1989), allowing the classification of individuals into only 78 distinct genotypes. This problem cannot be overcome by amplifying hypervariable minisatellites, since the most variable loci tend to have large alleles (>5kb) which are, in general, refractory to PCR amplification (Jeffreys et al., 1988).

In addition to these technical problems, there has also been considerable debate over the statistical evaluation of the population frequency of single locus DNA phenotype evidence (see for examples Lander, 1989; Devlin et al., 1990; Budowle et al., 1991). The general approach is to deduce, conservatively, appropriate allele frequencies (allowing for allele sizing uncertainties) in a reference population database, and then to deduce genotype frequencies from allele frequencies under the assumption that the population is at Hardy-Weinberg equilibrium. While most tests have failed to reveal major apparent departures from Hardy-Weinberg equilibrium (Odelberg et al., 1989; Devlin et al., 1990; Budowle et al., 1991; Chakraborty et al., 1991), the tests are relatively insensitive, particularly for rare genotypes with minimal or zero representation in the population database. An alternative and more satisfactory approach would be to compare evidentiary DNA phenotypes with very large databases of phenotypes gathered from population surveys and casework, to determine match frequencies based on the frequency of observed phenotypes. Such an approach requires a system capable of generating very large numbers of different and unambiguous DNA phenotypes.

Minisatellite alleles frequently vary not only in repeat copy number but also in the interspersion pattern of variant repeat units along alleles (FIG. 1A) (Owerbach and Aagaard, 1984; Jeffreys et al., 1985; Jarman et al., 1986; Wong et al., 1986, 1987; Nakamura et al., 1987a; Page et al., 1987; Gray and Jeffreys, 1991). We have previously investigated variation in allelic minisatellite variant repeat (MVR) maps at the hypervariable locus D1S8 (probe MS32—claimed in our UK Patent 2188323: Jeffreys et al., 1990). Alleles at this locus show two classes of repeat unit (a-type, t-type) which differ by a single base substitution which creates or destroys a HaeIII restriction site. The interspersion pattern of HaeIII+ and HaeIII-repeat units along an MS32 allele can be assayed by amplifying the entire allele, using amplimers from the DNA flanking the minisatellite, followed by end-labelling the amplified allele, partial digestion with HaeIII, and electrophoresis to display a ladder of labelled digest products extending from one of the flanking primer sites to each of the HaeIII-cleavable repeat units. This approach provides an unambiguous binary code for an allele, and has revealed very high levels of allelic variation in MS32 MVR maps, significantly greater than can be achieved by conventional Southern blot analysis of human genomic DNA. Curiously, there is a polarity of variation along MS32 alleles; at one end, there are relatively few distinct internal maps (haplotypes) in Caucasian populations, whereas the other end of alleles show far higher variability, suggesting a local mutational hot-spot responsible for altering allelic repeat unit copy number and reshuffling the pattern of variant repeat units (Jeffreys et al., 1990). However, the above MVR mapping method has proved to be cumbersome and can only be applied to MS32 alleles small enough (<5kb) to amplify by PCR (Jeffreys et al., 1990).

It is therefore desirable to provide a further method of characterising a sample of genomic DNA which overcomes, at least in part, the above mentioned disadvantages. According to a first aspect of the present invention we provide a method of characterising a test sample of genomic DNA which method comprises amplifying a tandemly repeated region, comprising more than one type of repeat unit, as far as internal repeat units of a specific type so as to generate a set of amplification products which identify the relative positions of the said internal repeat units within the tandemly repeated region, and separating the set of amplification products to provide a sample code.

The set of amplification products is conveniently produced by contacting the test sample of genomic DNA with type specific primer to prime selectively internal repeat units of a specific type, extending the said primers in the presence of appropriate nucleoside triphosphates and an agent for polymerisation thereof to produce a set of amplification products extending from the internal repeat units of a specific type to at least the end of the tandemly repeated region. The type specific primer is an oligonucleotide prepared either by synthetic methods or derived from a naturally occurring sequence, which is capable of acting as a point of initiation of synthesis when placed under conditions in which synthesis of a primer extension product which is complementary to a nucleic acid strand is induced, ie. in the presence of appropriate nucleoside triphosphates and an agent for polymerisation in an appropriate buffer and at a suitable temperature. In our European Patent, Publication No. 0332435, the contents of which are incorporated herein by reference, we disclose and claim a method for the selective amplification of template sequences which differ by as little as one base as well as type specific primers for use in the selective amplification method. Type specific primers for use in the present invention may therefore be designed with reference to our above mentioned European Patent, Publication No. 0332435. The selective amplification method is now commonly referred to as the Amplification Refractory Mutation System (ARMS). ARMS is a trade mark of ICI plc.

The type specific primer conveniently includes a tail sequence which tail sequence does not hybridise to the tandemly repeated region or to an adjacent region. By "an adjacent region" we mean a region sufficiently close to the tandemly repeated region to act as template for primer extension which could adversely interfere with the method of the invention. The set of amplification products produced as above and which extends to a common locus flanking the tandemly repeated region conveniently acts as template for a common primer which hybridises to the common locus and is extended in the presence of appropriate nucleoside triphosphates and an agent for polymerisation thereof to amplify the said set of amplification products. The above amplification procedures may be repeated as required. However amplification products may shorten progressively at each amplification cycle, due to the type specific primer priming internally on amplification products from previous cycles. It has been found that this problem may be overcome by use of a tail specific primer which hybridises to the complement of the tail sequence in the extension product of the common primer and is extended in the presence of appropriate nucleoside triphosphates and an agent for polymerisation thereof to amplify the common primer amplification products. In summary the tail sequence on the type specific primer is selected so that its complement in the extension product of the common primer provides a convenient template for the tail specific primer provided that the tail sequence and complementary sequences do not hybridise to the tandemly repeated region or to an adjacent region. Examples of convenient tail sequence lengths include up to 50, up to 40, up to 30 and up to 20 nucleotides.

The sets of amplification products prepared according to the above procedures are conveniently amplified in a polymerase chain reaction using the common and tail specific primers as defined above. The polymerase chain reaction is conveniently described in "PCR Technology" edited by Henry A. Ehrlich, published by Stockton Press—London/New York in 1989. The tail sequence on the type specific primer ensures that the tail specific primer primes internal repeat units of the desired type at each amplification cycle. The method of the present invention is conveniently effected in a single reaction using the type specific and common primers in combination with the tail specific primer. It has been found that the ratio of tail specific and/or common primer to type specific primer is conveniently more than 1:1. Thus, whilst we do not wish to be limited by theoretical considerations, at each amplification cycle the amplification products are more likely to be primed by the tail specific primer than by the type specific primer. Any internal priming off amplification products will produce authentic but relatively short amplification products in each amplification cycle. Routine experimentation allows the molecular biologist of ordinary skill to provide amplification products extending a desired distance into the tandemly repeated region of choice. Examples of convenient ratios of tail specific and/or common primer to type specific primer include at least 20:1, at least 30:1 and at least 40:1, preferably at least 50:1.

The set of amplification products is separated to provide a sample code according to any convenient procedure provided that the separation is carried out on the basis of the native (genomic) order of the individual repeat units of a specific type within the tandemly repeated region. It will be appreciated that the sample code may be provided from any convenient number of amplification products within the set and representing any convenient number of positions within the native order. In general, separation is effected on the basis of the relative sizes of the amplification products and these are conveniently separated via known gel electrophoresis techniques resulting in a ladder of amplification products representing the sample code. Direct visualisation of the amplification products, for example using staining procedures, and in particular ethidium bromide, are preferred. If required however the amplification products may be identified using a probe which for example hybridises specifically to the tandemly repeated region or to a flanking region. The probe may comprise any convenient radioactive label or marker component. Preferably a non-radioactive label such as the triggerable chemiluminescent 1,2-dioxetane compound Lumi-Phos$^{530}$ disclosed and claimed in U.S. Pat. No. 4,959,182 is employed. Lumi-Phos$^{530}$ is a registered trade mark of Lumigen Inc.

The method of the present invention is preferably used to analyse at least two specific types of internal repeat unit within the tandemly repeated region. This increases considerably the informativeness of the resulting sample code. Where amplification is effected using type specific primers this also provides integral control of any mispriming on non-type specific internal repeat units. Thus for example the amplification products are separated as above to provide two or more type specific ladders of amplification products.

In general the method of the present invention is carried out with reference to one or more controls. In particular the method is carried out with reference to a control sample of known profile. Thus for example where the amplification products are provided as type specific ladders the positions of the individual "rungs" are compared with the ladder profile for the control sample. The ladder profile for the control sample may also conveniently provide reference positions throughout the tandemly repeated region for internal repeat units of a specific type comprised in the sample code.

The internal repeat units of a specific type and included in the sample code are conveniently of invariant length. This simplifies analysis of, for example type specific ladder(s) of amplification products.

Specific types of internal repeat units may arise from base substitutions, deletions, translocations or similar events. Where the internal repeat units are of invariant length this generally arises from base substitution(s) within the repeat units. Base substitutions may be detected using any known technique such as direct sequence analysis but are conveniently identified with reference to the presence or absence of restriction sites within the internal repeat units (Jeffreys et al., 1990). Thus, for example the MS32 minisatellite claimed in our UK patent no. 2188323 comprises two types of repeat unit of invariant length which are HaeIII cleavable and HaeIII resistant respectively. Therefore in a preferred aspect of the method of the present invention the tandemly repeated region is comprised in the MS32 minsatellite and two specific types of internal repeat unit arise from the presence or absence of a HaeIII site within internal repeat units. The type specific primers conveniently comprise the following sequences 3' CGGTCCCCACTGAGT 5' (SEQ ID NO:2) and 3'TGGTCCCCACTGAGT 5'(SEQ ID NO:3). Examples of preferred type specific primers comprising the above sequences are 3' CGGTCCCCACT-GAGTCTTAC 5' (SEQ ID NO:13) and 3'TGGTCCCCACT-GAGTCTTAC 5' (SEQ ID NO: 12) respectively. Where at least two type specific primers are employed their relevant concentration ratio(s) may be selected so as to reflect their relevant hybridisation characteristics. Thus for example in respect of the sequences 3' CGGTCCCCACTGAGTCTTAC 5' and 3'TGGTCCCCACTGAGTCTTAC 5' a convenient ratio is about 2:1. Alternatively, equal concentrations of type specific primers may be used and appropriate mismatches introduced elsewhere in the primer sequence (see for example our European patent, publication no. 0332435).

As explained earlier above, a large number of tandemly repeated regions have now been reported in the literature. The skilled man is able to determine whether a given region is suitable for use in the method of the invention by any convenient analysis of the internal repeat unit structure, for example by direct sequencing techniques. In general, minisatellite regions will be selected for analysis since most of the microsatellite loci, and particularly those based on dinucleotide repeats, show complex multi-band patterns per allele on DNA sequencing gels which appear to arise through Taq polymerase slippage at dinucleotide repeats during amplification (Weber and May, 1989) and through non-templated nucleotide addition catalysed by Taq polymerase (Clark, 1988). As a result, it is sometimes difficult to determine with confidence the true size of a given allele at microsatellites.

To date we have identified convenient tandemly repeated regions comprised in the minisatellite regions MS31, MS32, and MS1. These minisatellite regions are claimed in our UK patent no 2188323 and corresponding worldwide patent applications. A particular tandemly repeated region is MS32.

The tandemly repeated region is, in general, identified either by unique internal repeat sequence or by unique flanking sequence. Alternatively, and less preferably, the region of interest is isolated from the sample mixture using known separation procedures, for example, by sample digestion and use of a single locus probe specific for a region at a distance from the region of interest.

A significant advantage of our claimed method is that the genomic DNA sample to be tested does not require any elaborate pre-treatment. Thus the DNA sample may comprise total genomic DNA, including mitochondrial DNA, and the analysis of both maternal and paternal alleles of the selected tandemly repeat region(s) can be readily carried out.

By "genomic DNA" we mean nucleic acid, such as DNA, from any convenient animal or plant species, such as humans, cattle, and horses, especially humans. Known DNA typing procedures have already been effected on a wide variety of species. The minisatellite regions MS1, MS31 and MS32 have proved to be human specific and accordingly are not believed to be suitable for the characterisation of non-human samples.

Where a common primer is used this may hybridise to any convenient locus flanking the tandemly repeated region provided that informative amplification products are obtained. In general, the common primer is selected so that the resulting set(s) of amplification products may be conveniently separated according to size by gel electrophoresis. In respect of the MS32 minisatellite we have previously disclosed (Jeffreys et al, 1988—European patent application, publication no. 0370719/ page 18 and FIG. 11) over 300 bases of 3' flanking sequence and provided examples of convenient primers.

The flanking locus is advantageously polymorphic since the test sample may be further characterised with respect to any informative sequence polymorphism at this locus. By "informative sequence polymorphism" we mean any sequence polymorphism which provides a useful degree of information within a population to be analysed. Convenient polymorphisms are in general detected in about 1%–50% of a given population, such as in up to 2%, up to 5% or up to 10% of individuals.

Amplification of a selected sequence variant of the common locus is conveniently effected using a type specific common primer in a manner directly analogous to the repeat unit type specific primers of the present invention. Thus, the type specific common primer is extended in the presence of appropriate nucleoside triphosphates and an agent for polymerisation thereof to amplify a set of amplification products comprising the selected sequence variant. The type specific common primers are conveniently designed and produced as described earlier above with reference to the type specific primers and our European patent, publication no. 0332435.

The above aspect of the invention may advantageously be used to characterise the test sample of genomic DNA in respect of either or both maternal and paternal alleles without prior separation of the alleles. By way of example, sample DNA from an individual who is heterozygous for a selected variant of the common locus will only give rise to type specific common primer amplification products from one allele. Similarly, sample DNA from an individual who does not possess the selected variant will not give rise to any common primer amplification products. Any such results may be conveniently verified by using a non-type specific common primer at the same common locus to provide amplification products for both alleles. In general, for routine characterisation purposes a non-type specific common primer will be employed to obtain information from both alleles.

The preceding aspects of the method of the invention using sequence variants of the common primer locus to effect allele "knockout" are based on the unexpected discovery that primer 32D (Jeffreys et al, 1988—FIG. 11) hybridises to a region comprising a polymorphic site. Accordingly, in a convenient aspect the tandemly repeated region is comprised in MS32 and the polymorphic site in the flanking region is comprised in the locus to which 5' CGACTCGCAGATGGAGCAATGGCC 3' (SEQ ID NO: 25) (primer 32D) hybridises. Convenient type specific common primers for this locus comprise the sequence 5' GCAGATGGAGCAATG 3' (SEQ ID NO: 1) such as 5' CGACTCGCAGATGGAGCAATG 3' (SEQ ID NO:24) (primer 32D2). Convenient non-type specific common primers for this locus comprise the sequence 5' GCAGATGGAGCAATGGCC 3' (SEQ ID NO:4) such as 5' CGACTCGCAGATGGAGCAATGGCC 3' (primer 32D).

A further significant advantage is that our claimed method may be carried out using a partially degraded DNA sample. The only requirement is that at least a part of the tandemly repeated region to be analysed can be amplified to provide a sample code. In respect of the MS32 minisatellite we now provide a non-type specific common primer (320) 5' GAGTAGTTTGGTGGGAAGGGTGGT 3' (SEQ ID NO:26) which is particularly useful with partially degraded samples since it hybridises to a region directly adjacent to the tandemly repeated region.

In a further aspect of the method of the present invention two or more sets of differentially labelled amplification products are prepared simultaneously. Convenient labels include specific binding substances such as biotin/avidin and also immunogenic specific binding substances. Further convenient labels include chromophores and/or fluorophores such as fluorescein and/or rhodamine. In general the relevant primers are labelled although other methods of providing labelled amplification products are not excluded.

In any relevant preceding aspect of the present invention different type specific primers may comprise different tail sequences to facilitate separation of the amplification products. The method of the present invention may be used to characterise more than one tandemly repeated region, for example by simultaneous amplification using appropriate type specific primers. This enables a more detailed sample code to be obtained. Thus, by way of example the minisatellite regions MS1, MS31 and MS32 may be amplified at the same time.

As mentioned earlier above a significant advantage of the method of the present invention is that it provides a sample code individual to the genomic DNA sample. Depending on the procedure used to separate the set(s) of amplification products the sample code may already be in machine readable form, for example suitable for scanning and digital encoding. Therefore according to a further aspect of the present invention we provide an individual sample code prepared according to any preceding aspect of the present invention. The sample code may be based on any convenient number of coding states such as at least 2, for example at least 3, at least 4, at least 5, at least 6, at least 7, at least 8 or at least 9 coding states. All the above are independent and convenient numbers of coding states. In general where the method of the present invention is performed using two type specific primers on total genomic DNA the profile of both alleles can be conveniently represented as a ternary code for each internal repeat position ie. both type a, both type t or heterozygous type at In respect of the MS32 minisatellite we have identified a further distinct repeat type O ("null") which is not primed by either type specific primer a or type specific primer t. This further repeat type allows the sample code to be expanded by three further coding states aO, tO, and OO. Runs of apparent "null" repeats can arise in the coding ladder beyond the end of short alleles; such non-existent "null" repeats can be reliably identified by MVR-PCR both of separated alleles and in total genomic DNA. Null or O type repeats can also arise from additional repeat unit sequence variants within alleles which differ enough to prevent priming by either a-type or t-type repeat primers. 1.6% of repeat units within Caucasian alleles are O-type repeats and can be accurately identified in separated alleles by the absence of specific internal rungs on the MVR ladder. However, their detection in total genomic DNA requires correct interpretation of MVR-PCR band intensities (dosage). While the correct discrimination of heterozygous null positions (for example, homozygous a/a versus heterozygous a/O) has very little effect on the power of digital codes in individual identification, correct identification of heterozygous null codes is important when using diploid codes for parentage analysis. For example, suppose that, at a given repeat position, the mother is t/t, the father a/O and the child t/O; mis-scoring of the father as a/a or the child as t/t would lead to a false paternal exclusion, exactly analogous to the problems created by null alleles at classical marker systems.

We also provide a database which comprises a multiplicity of individual sample codes prepared as above. The individual sample codes are preferably derived from a tandemly repeated region within the MS32 minisatellite. Whilst we do not wish to be limited by any theoretical considerations we have found that variation within the MS32 minisatellite appears to be associated with a clustering of mutation events at the 3' end of the minisatellite. Therefore the individual sample code is preferably derived from at least 5 or at least 10 internal repeat units at the 3' end of the minisatellite, more preferably from at least 15 internal repeat units at the 3' end of the minisatellite. By "at the 3' end of the minisatellite" we mean within 100 internal repeat units, such as within 50, 40, 30, or 20 repeat units of the 3' end of the minisatellite. The 3' end of the minisatellite is defined with reference to 5'-3' extension of the type specific primers 3' CGGTCCCCACTGAGTCTTAC 5' and 3'TGGTCCCCACTGAGTCTTAC 5' and the MS32 3' flanking sequence disclosed, for example on page 18 of our European patent application, publication no. 0370719. The above database may be established and used for any convenient characterisation purposes, such as in the identification of individuals and the determination of individual relationships.

The present invention also provides a type specific primer to prime selectively internal repeat units of a specific type within a tandemly repeated region comprised in any one of MS 1, MS32 or MS32. Convenient type specific primers of the present invention include those used where the tandemly repeated region is comprised in MS32 and the specific type of internal repeat unit arise from the presence or absence of a HaeIII site in the repeat units, such as a set of two type specific primers which comprise the following sequences 3' CGGTCCCCACTGAGT 5' and 3'TGGTCCCACTGAGT 5' respectively, such as 3' CGGTCCCCACTGAGTCTTAC 5' and 3'TGGTCCCCACTGAGTCTTAC 5'. In respect of the MS3 1A minisatellite convenient type specific primers comprise the following sequences AGGTGGAGGGTGTCTGTGA (SEQ ID NO:6) and GGGTGGAGGGTGTCTGTGA (SEQ ID NO:7).

In a further aspect of the present invention we provide a test kit which comprises at least two complementary type specific primer(s) as defined above together with optional common primer as defined above and/or optional tail specific primer as defined above, the test kit further including appropriate buffer, packaging and instructions for use. The test kit conveniently further comprises appropriate nucleoside triphosphates and/or an agent for polymerisation thereof. Additional optional items for inclusion in the test kit include control DNA of known profile, an optionally labelled probe for the tandemly repeated region and a probe detection system.

The invention also relates to a computer when programmed to record individual sample codes as defined above. Further independent aspects of the present invention relate to a computer when programmed to search for similarities between individual sample codes as defined above and to a computer when programmed to interrogate a database as defined above.

The term "tandem repeat" is used herein to refer to at least 2 repeats of a sequence comprising at least one sequence polymorphism in a given population. In general the tandemly repeated region used in the method of the present invention comprises at least 5, or at least 10, or at least 15 tandem repeats, such as at least 20 or at least 30, 40, 50 or at least 100 tandem repeats.

MVR diploid codes offer many major advantages over currently used DNA typing systems that involve length measurements of VNTR (minisatellite or microsatellite) alleles, including the following:

1. MVR coding does not involve error-prone fragment length measurement, and provides for the first time digital typing information ideally suited to computer databasing.

2. The MVR-PCR profiles include major informational redundancy useful for confirming code authenticity.

3. Code generation does not require standardization of electrophoretic systems.

4. Laboratories using MVR-PCR can readily check the authenticity of their codes by including a standard individual of known code, preferably an individual containing examples of the scarce codes 4(aO), 5(tO) and 6(O).

5. Criteria for declaring a match betwen a forensic sample and a criminal suspect are no longer subjective, since samples match if the MVR codes are indistinguishable.

6. Side-by-side comparisons of DNA samples on the same gel are no longer necessary. This will enable forensic laboratories to segregate forensic sample away from suspects, minimizing the risk of sample mix-up.

7. MVR-PCR is capable of generating information from degraded DNA, trace amounts of DNA and, in some circumstances, mixed DNA samples. MVR coding is also technically simple and should therefore be suitable for routine forensic investigations.

8. All participating laboratories can contribute code data to generate very large communal population and investigative databases. Given the fact that current estimates suggest in excess of 6000 diferent MS32 alleles, and therefore $>2\times10^7$ diploid codes, it is likely that very large databases can be constructed before any significant saturation of MS32 MVR code types occurs. (Note that this will be true for unrelated individuals but not for siblings, since a pair of siblings will have an approximately 1/4 chance of sharing the same parental alleles and therefore MVR code).

9. Very large communal databases provide a simple method for determining the statistical significance of a match between a forensic sample and a suspect, simply by determining the frequency (probably zero) of the particular MVR code in the communal database. The evidence presented, for example in a court is therefore reduced to a simple statement that the code in the forensic sample and suspect match, and that the code has not been seen in x other individuals typed from the appropriate ethnic group. This approach uses phenotypic frequencies rather than genotype frequencies deduced under assumptions of Hardy-Weinberg equilibrium. Cumulative typing of isolated communities can also be used to determine whether MVR code matching frequencies can be significantly perturbed by inbreeding.

10. MVR codes also provide a method for parentage testing, where again the statistical evaluation of the significance of a paternal match can be simply estimated by determining the proportion of individuals in the appropriate communal database who are not excluded as non-fathers.

11. All paternity cases where parentage is established automatically yield haplotype data on the four parental alleles which can be accumulated within a very large communal allele database, useful for defining allele diversity and frequencies more precisely. The term "set of amplification products" is used herein to refer to a plurality of amplification products which identify the relative positions of internal repeat units of a specific type within the tandemly repeated region. Any convenient number of amplification products are comprised in the set such as at least 2, at least 5, at least 10, at least 15, at least 20, or at least 30 amplification products.

The term "more than one type of repeat unit" is used herein to refer to types of internal repeat units within the tandemly repeated region which may be distinguished according to an informative sequence variation. By way of example the presence or absence of a particular restriction site in a repeat unit provides two types of repeat unit ie. a first type of repeat unit which comprises the particular restriction site and a second type which which does not comprise the particular restriction site. Accordingly the first and second types of repeat unit are "internal repeat units of a specific type". It will be understood that a further informative sequence variation between internal repeat units provides further types of repeat unit and allows further and independent characterisation of the tandemly repeated region.

The term "informative sequence variation" is used herein to indicate sequence variation which provides a useful degree of information within a population to be analysed. The term "nucleoside triphosphate" is used herein to refer to nucleosides present in either DNA or RNA and thus includes nucleosides which incorporate adenine, cytosine, guanine, thymine and uracil as base, the sugar moiety being deoxyribose or ribose. In general deoxyribonucleosides will be employed in combination with a DNA polymerase. It will be appreciated however that other modified bases capable of base pairing with one of the conventional bases adenine, cytosine, guanine, thymine and uracil may be employed. Such modified bases include for example 8-azaguanine and hypoxanthine.

The term "nucleotide" as used herein can refer to nucleotides present in either DNA or RNA and thus includes nucleotides which incorporate adenine, cytosine, guanine, thyrnine and uracil as base, the sugar moiety being deoxyribose or ribose. It will be appreciated however that other modified bases capable of base pairing with one of the conventional bases, adenine, cytosine, guanine, thymine and uracil, may be used in the diagnostic primer and amplification primer employed in the present invention. Such modified bases include for example 8-azaguanine and hypoxanthine.

In addition, it will be understood that references to nucleotide(s), oligonucleotide(s) and the like include analogous species wherein the sugar-phosphate backbone is modified and/or replaced, provided that its hybridisation properties are not destroyed. By way of example the backbone may be replaced by an equivalent synthetic peptide.

As outlined above the method of the present invention is particularly applicable to MS32 alleles of any length and also applicable to total genomic DNA to display the superimposed MVR maps of both alleles, thereby generating a ternary, rather than binary code (FIG. 1A). The approach is outlined in FIG. 1B,C and uses two MVR-type specific primers/amplimers. Each amplimer consists of 20 nucleotides of MS32 repeat unit terminating at the HaeIII$^{+/-}$ variable site and differing at the 3' end such that one amplimer may only prime off a-type repeat units and the other amplimer only off t-type repeats. Amplification using one or other MVR-type specific primer together with amplimer 32D from the minisatellite flanking DNA will generate two complementary sets of products from the ultravariable end of a given MS32 allele, from which the MVR maps can be deduced. However, PCR products may progressively shorten at each PCR cycle, due to the MVR-specific amplimer priming internally within PCR products, to generate eventually a set of PCR products extending from the 32D flanking site to, at most, the first few repeat units. To prevent any such collapse, each MVR-specific primer preferably carries an identical 20 nt 5' extension "TAG" to create oligonucleotides 32-TAG-A and 32-TAG-T. Duplicate PCR amplifications are carried out with a very low concentration of 32-TAG-A or 32-TAG-T plus high concentrations of 32D and the TAG sequence itself. At each cycle of PCR, each MVR-specific primer will prime from one of its complementary repeat units within the minisatellite and extend into the flanking DNA past the 32D priming site. At the next PCR cycle, 32D will prime on the first product and extend back across the minisatellite, terminating at the TAG sequence and creating a sequence complementary to TAG from which the TAG primer can now prime. At the next PCR cycle, this second PCR product can now amplify, and is much more likely to be amplified by 32D and TAG, rather than 32D and the MVR-specific primer, since TAG is present at high concentration. As a result, a stable set of PCR products will be generated, extending from the 32D priming site to each a-type or t-type repeat unit, depending on the MVR-specific primer used. Any internal priming off PCR products by 32-TAG-A or 32-TAG-T may create authentic but relatively short PCR products in each reaction. By adjusting the concentration of 32-TAG-A and 32-TAG-T relative to 32D and TAG, it is possible to create sets of PCR products extending at least 80 repeat units (2.3 kb) into the minisatellite.

As explained earlier above the use of a tail (or TAG) specific primer which hybridises to the complement of the tail sequence in the extension product of the common primer prevents internal priming within the tandemly repeated region and subsequent shortening of the amplification products at each amplification cycle.

We now disclose that the above principle may be applied to any convenient detection method involving amplification by primer extension. In known procedures comprising a polymerase chain reaction mispriming can occur at each amplification cycle, especially where the primer is used to detect for example single base mismatches or to detect a particular sequence against a background of related sequences. Such mispriming may only occur as a very low percentage of total priming events per amplification cycle but will increase significantly as a function of the overall number of cycles. The present invention now provides a two stage procedure wherein as a first stage the initial diagnostic interaction between a primer comprising a tail sequence and a sample template may conducted at optimum hybridisation stringency. Any primer extension products are then amplified using a further primer. As a second stage the above extension products are then amplified using a tail specific primer and the further primer. Accordingly, whilst mispriming may still occur the overall level may be significantly reduced.

Therefore, according to a further and independent aspect of the present invention we provide a novel method for detecting the presence or absence of at least one diagnostic base sequence in one or more nucleic acids contained in a sample, which method comprises contacting the sample with a diagnostic primer for each diagnostic base sequence in the sample nucleic acid, the nucleotide sequence of each diagnostic primer being such that it is substantially complementary to the corresponding diagnostic base sequence, under hybridising conditions and in the presence of appropriate nucleoside triphosphates and an agent for polymerisation thereof, such that an extension product of a diagnostic primer is synthesised when the corresponding diagnostic base sequence is present in the sample, no extension product being synthesised when the corresponding diagnostic base sequence is not present in the sample and any extension product of a diagnostic primer acts as template for extension of a further primer which hybridises to a locus at a distance from the relevant diagnostic base sequence, and wherein at least one of the diagnostic primer(s) further comprises a tail sequence which does not hybridise to a diagnostic base sequence or a region adjacent thereto, and contacting the above mixture with a tail primer which hybridises to the complement of the tail sequence in an extension product of the further primer and is extended in the presence of appropriate nucleoside triphosphates and an agent for polymerisation thereof to amplify the further primer amplification products whereby the presence or absence of the diagnostic base sequence(s) in the nucleic acid sample is detected from the presence or absence of tail specific primer extension product.

The tail sequences may be the same or different but are conveniently identical or substantially similar so that a single tail primer may be used. This facilitates the performance of large multiplexes without overloading the reaction mix with different primers. We have found that the use of identical tail sequences can be advantageously used to even out the efficiencies of different amplification reactions.

We have also surprisingly found that tailed primers can also be used to prevent the formation of "primer dimers" and other inter-primer artefacts. These are a particular problem in homogeneous assays using for example intercalating dyes to detect double stranded nucleic acid. See for example Ishiguro et al, Anal. Biochem., 1995, 229, 207–213, especially pages 211–212. Whilst we do not wish to be limited by theoretical considerations, it is believed that the formation of primer dimers is dependent on some degree of homology between primers and their use at high concentrations. It may be possible to reduce the formation of primer dimers by careful primer design. However where many primers are used at high concentrations, for example in PCR multiplexes, this becomes more difficult. We now disclose the use of diagnostic and further primers which are genome specific at their 3'-termini but which carry common extensions (tails) at their 5'-termini. These are used in combination with a common tail specific primer which can prime from the complement of the tail sequence in extension products of further primer(s). Thus whilst primer dimers and other inter-primer artefacts could occur during first phase diagnostic priming, these cannot be amplified during subsequent rounds of tail specific priming. It will be appreciated that the diagnostic primers are conveniently used at concentrations which allow satisfactory priming on their genomic template(s) but do not allow significant PCR amplification. The common tail specific primer isused at higher concentration than the genome specific primers.

To ensure that primer-dimers and other artefacts are avoided a common tail and common tail specific primer are preferably used for all primers present in the reaction mix, including control primers.

We have also found that it is advantageous to switch from diagnostic primer priming to tail primer priming by means of a temperature switch. The primers are selected so that the melting temperature of the tail primer is higher than the diagnostic primer. An increase in temperature will favour priming, for example after one or conveniently two rounds of diagnostic primer priming, by the tail primer.

The diagnostic primer may be an allele specific primer. In EP-A-0333465 (Baylor College of Medicine) there is described a detection method using two competing primers for the detection of diagnostic base sequences which differ by as little as a single base. This method depends on careful control of melting temperature (Tm) and is known as competitive oligonucleotide priming (COP). Competing primers may be used in the method of this invention, either the primers are differentially labelled or the amplification products are separated according to size, for example by the use of different size tails on the primers. Furthermore in our European Patent, Publication No. 0332435, the contents of which are incorporated herein by reference, we disclose and claim a method for the selective amplification of template sequences which differ by as little as one base. The above method is now commonly referred to as the Amplification Refractory Mutation System (ARMS). This is of particular use, for example, where diagnostic base sequence(s) are only present in low concentration in complex nucleic acid mixtures.

Therefore in a preferred aspect of the above detection method a terminal nucleotide of at least one diagnostic primer is either complementary to a suspected variant nucleotide or to the corresponding normal nucleotide, such that an extension product of a diagnostic primer is synthesised when the terminal nucleotide of the diagnostic primer is complementary to the corresponding nucleotide in the diagnostic base sequence, no extension product being synthesised when the terminal nucleotide of the diagnostic primer is not complementary to the corresponding nucleotide in the diagnostic base sequence.

The diagnostic primers for use in the preceding aspect are conveniently designed with reference to our above mentioned European Patent, Publication No. 0332435. By "substantially complementary" we mean that primer sequence need not reflect the exact sequence of the template provided that under hybridising conditions the primers are capable of fulfilling their stated purpose. This applies equally to diagnostic and tail primers. In general, mismatched bases are introduced into the primer sequence to provide altered hybridisation stringencies. Commonly, however, the primers have exact complementarity except in so far as non-complementary nucleotides may be present at a predetermined primer terminus as hereinbefore described.

In the diagnosis of, for example, cancer the situation may arise whereby it is desirable to identify a small population of variant cells in a background of normal cells. The ARMS system is well suited for this purpose since it discriminates between normal and variant sequences even where the variant sequence comprises a very small fraction of the total DNA. Whilst we do not wish to be limited by theoretical considerations we have successfully performed ARMS assays in which the ratio of mutant to normal DNA was 1:100 and we believe that even larger ratios may be readily used. To optimise the sensitivity of the ARMS reaction it may be performed in isolation ie. with a single ARMS primer since in duplex or multiplex reactions there may be competitive interaction between the individual reactions resulting in a loss of sensitivity. A control reaction is desirable to ensure that a polymerase chain reaction has taken place. In a test for an inherited mutation the copy number of the mutation and other genomic is typically 1:1 or 1:2, so a genomic control reaction can be used without compromising sensitivity or creating an imbalance in the system. In a cancer test however, the use of a genomic control reaction may swamp the test reaction leading to a loss of sensitivity. We have now found that ARMS primer(s) comprising tail sequences may advantageously be used in a two stage amplification procedure comprising a genomic control reaction. In the first stage ARMS primer(s) comprising non-complementary tail(s) are used to amplify any variant sequence which may be present. In addition to the ARMS reaction a genomic control reaction is performed in the same reaction vessel using primers at very low concentation. The control reaction primers also have non-homologous tails which may or may not have the same sequence as the ARMS primer tail(s). In the second stage tail specific primers are added and the temperature increased to prevent the original genomic control primers from functioning. In this second stage any variant sequence product is further amplified and the product of the control reaction from the first stage is also amplified to give a detectable product. Thus the ARMS reaction will only take place if variant sequence is present in the original sample and the control reaction will only function if both the first and second-stage amplification reactions have worked.

A further and important use of ARMS is for detecting the presence or absence of more than one suspected variant nucleotide in the same sample. The ability of ARMS to selectively amplify sequences depending on the predetermined nucleotide sequence of the diagnostic primers enables multiple amplification products to be distinguished simply, accurately and with minimal operator skill thus making it possible to provide a robust technique for screening a single sample for multiple nucleotide variations. The use of ARMS to detect more than one suspected variant nucleotide in the same sample is conveniently referred to as multiplex ARMS. Multiplex ARMS is thus of particular interest in screening a single sample of DNA or RNA for a battery of inherited conditions such as genetic disorders, predispositions and somatic mutations leading to various diseases. Such DNA or RNA may for example be extracted from blood or tissue material such as chorionic villi or amniotic cells by a variety of techniques such as those described by Maniatis et al, Molecular Cloning (1982), 280–281. Morever as the molecular basis for further inherited conditions becomes known these further conditions may simply be included in the screening technique of the present invention. Multiple amplification products may be distinguished by a variety of techniques. Thus for example probes may be employed for each suspected amplified product, each probe carrying a different and distinguishable signal or residue capable of producing a signal.

A much simpler and preferred method of distinguishing between ARMS amplification products comprises selecting the nucleotide sequences of the amplification primers such that the length of each amplified product formed during the process of the present invention is different. In this regard the number of base pairs present in an amplification product is dictated by the distance apart of the diagnostic and amplification primers. Thus the amplification primers may be designed such that each potential variant nucleotide is associated with a potential amplification product of different length.

In an ARMS reaction diagnostic for a particular point mutation the sequence of the primers is largely constrained by the sequence of the DNA adjacent the mutation of interest. The 3' base of the primer usually matches the base altered by the mutation and extra destabilisation is introduced to give the required level of specificity. The term "specificity" refers to the ratio of the yield of product when an ARMS primer is used to prime its target sequence compared to the yield of mis-primed product from the non-target sequence.

In a multiplex ARMS reaction it is desirable that the individual ARMS reactions work with similar efficiency to allow the simultaneous detection of all the reaction products. This may be achieved for example by altering the concentration of the primers, alteration of the number/composition of reactions, or alteration of the ammount of additional destabilisations introduced into the ARMS primers. Whilst these methods are normally sufficient to obtain a balanced multiplex ARMS reaction the use of tail or tag sequences may have advantages in certain situations. In particular these may allow a more specific test. By way of example, where a strong additional mis-match is used to obtain specificity the yield of corresponding multiplex product may be low. Reducing the additional mis-match strength may not be possible without compromising specificity. A tail sequence which in combination with a tail specific primer provides a good substrate for a DNA polymerase may be used to balance the multiplex reaction. A range of tail/primer combinations of known priming ability may be provided. Thus by way of example as a first amplification step the priming/mis-priming ratio is optimised without regard to product yield. Product yield is then balanced in the second amplification step using an appropriate range of tail/primer combinations.

In our UK patent application no. 9201686.4 we disclose and claim that multiplex ARMS may be successfuly performed where diagnostic primer extension products of more than one diagnostic base sequence of a nucleic acid sample comprise a complementary overlap. This unexpected improvement to multiplex ARMS is referred to hereinafter as overARMS. OverARMS now facilitates the detection and analysis of, for example, inherited or infectious disease where the potential variant nucleotides are closely spaced.

Therefore in a further aspect of the claimed detection method the (potential) extension products of at least two diagnostic primers comprise a complementary overlap. The overlap may occur due to any convenient arrangement of the diagnostic primers. Thus for example the diagnostic primers may conveniently be opposed as illustrated in FIG. 8 (i). Furthermore we have found that ARMS may be successfully performed where the diagnostic primer(s) for more than one diagnostic base sequence in a nucleic acid sample themselves comprise a complementary overlap.

Therefore in a further aspect of the claimed detection method at least two diagnostic primers themselves comprise a complementary overlap. Thus for example the primers are superimposed on the same strand as illustrated in FIG. 8 (iii) or less preferably overlap as illustrated in FIG. 8 (ii). More conveniently the primers are nested as illustrated in FIG. 8 (iv).

In an overARMS reaction the size of the reaction products can be used to identify individual combinations of variant nucleotides. Where the products are separated for example on an agarose gel this approach may be limited by the resolving power of the gel. By way of example in a high resolution agarose gel overARMS may presently be used to identify mutations within about 10–15 bases of each other. The size of the outer overARMS primer was increased to give a larger product and we surprisingly found that the yield of the smaller overARMS product was significantly reduced. Whilst we do not wish to be limited by theoretical considerations we believe that target masking takes place due to the increased Tm of the larger overARMS primer which binds preferentially to the target DNA and prevents the smaller overARMS primer from hybridising. Use of a tailed outer overARMS primer may provide the increased product size necessary for resolution but since it is non-complementary at its 5' end the Tm will be similar to the smaller primer.

OverARMS is conveniently used for HLA typing, in the diagnosis of β-thalasaemia, sickle cell anaemia, phenylketonuria (PKU), Factor VIII and IX blood disorders and α-1-antitrypsin deficieny. A particular use for OverARMS is in the detection and diagnosis of cystic fibrosis. Convenient cystic fibrosis alleles are disclosed in our European Patent Application No. 90309420.9; by B. Kerem et al, Science, 1989, 245, 1073–1080; by J. R. Riordan et al, Science, 1989, 245, 1066–1073; by J. M. Rommens et al, Science, 1989, 245, 1059–1065; by G. R. Cutting et al, Nature, 346, 366–368; by M. Dean et al, Cell, 61, 863–870; by K. Kobayashi et al, Am. J. Hum. Genet., 1990, 47, 611–615; by B. Kerem et al, Proc. Natl. Acad. Sci. USA, 1990, 87, 8447; by M. Vidaud et al, Human Genetics, 1990, 85, (4), 446–449; and by M. B. White et al, Nature, 344, 665–667.

Our two stage amplification process using diagnostic and tail primers in combination with a further common primer is conveniently carried out using all three primers simultaneously and preferably using a ratio of tail specific and/or further primer(s) to diagnostic primer(s) of at least 1:1, such as at least 20:1, at least 30:1, and at least 40: 1, preferably at least 50:1. All of the above detection methods involving PCR amplification may be provided as homogeneous assays.

For example fluorescent intercalators such as ethidium bromide are used to detect double stranded DNA or RNA. Alternative dyes include those available from Hoechst such as TO-TO-1 (a dimer of thiazole orange), oxazole yellow (YO, also known as YO-PRO) and its dimer YO-YO. These newer dyes have a greater fluorescent enhancement than ethidium bromide when bound to dsDNA and bind more strongly to a duplex. We have found that for ethidium bromide, little or no inhibition of PCR occurs and the hybridisation kinetics are unaffected when the ethidium bromide concentration is such that only 10% of the available ites are intercalated. Fluorescence may be detected using any convenient detection system such as for example those commercially available from Perkin-Elmer/ABI which allow real time monitoring of the accumulation of fluorescence.

We also provide a kit for detecting the presence or absence of at least one diagnostic base sequence in one or more nucleic acids contained in a sample, which kit comprises a diagnostic primer for each diagnostic base sequence, the nucleotide sequence of each diagnostic primer being such that it is substantially complementary to the corresponding diagnostic base sequence, such that under hybridising conditions and in the presence of appropriate nucleoside triphosphates and an agent for polymerisation thereof an extension product of each diagnostic primer is synthesised when the corresponding diagnostic base sequence is present in the sample, no extension product being synthesised when the corresponding diagnostic base sequence is not present in the sample and wherein at least one of the diagnostic primer(s) further comprises a tail sequence which does not hybridise to a diagnostic base sequence or a region adjacent thereto, together with appropriate buffer, packaging and instructions for use.

The kit conveniently further comprises at least one of the following items:
(i) each of four different nucleoside triphosphates
(ii) an agent for polymerisation of the nucleoside triphosphates in (i)
(iii) tail specific primer(s)
(iv) a further primer which hybridises to a region at a distance from the diagnostic region(s) to which the diagnostic primer(s) selectively hybridise.

The kit conveniently comprises a set of two diagnostic primers for each diagnostic portion of a target base sequence, a terminal nucleotide of one diagnostic primer being complementary to a suspected variant nucleotide associated with a known genetic disorder and a terminal nucleotide of the other diagnostic primer being complementary to the corresponding normal nucleotide.

The invention will now be further described by, but not limited to, the following examples, tables and figures wherein:

BRIEF DESCRIPTION OF THE DRAWINGS

FIGS. 3A–3C shows the minisatellite repeat unit compositition of MS32 alleles. A, examples of MVR allele codes generated by MVR-PCR and by partial HaeIII cleavage of end-labelled amplified alleles (Jeffreys et al., Cell, 1990, 60, 473–485). Allele codes are shown in the opposite orientation from that used in Jeffreys et al (1990). and thus extend into the allele from the more variable end of MS32 alleles. The first repeat unit cannot be reliably scored by MVR-PCR and is denoted "?" Code discrepancies are indicated by "x". Allele 1, MVR-PCR and HaeIII codes fully concordant;

allele 2, presence of null (0-type) repeat units which cannot be primed by either 32-TAG-A or 32-TAG-T; allele 3, example of a short allele (38 repeat units) showing that MVR-PCR coding extends to the terminal repeat unit; allele 4, showing the only example of an a/t discrepancy between MVR-PCR and HaeIII coding. B, repeat unit composition of MS32 alleles determined from 32 different Caucasian alleles mapped by MVR-PCR and by HaeIII cleavage. The numbers indictaed in the HaeIII$^+$ and HaeIII-columns represent the numbers of repeat units. C, probable location of additional minisatellite variant repeats. X, a substitution at the first base of the HaeIII site will destroy the site but not prevent priming by 32-TAG-A, generating a repeat unit scored as a-type by MVR-PCR but t-type by HaeIII (see A4 above). Y, substitution(s) in this region might block priming by both 32-TAG-A and 32-TAG-T to generate null (0-type) repeats.

Figure 2:
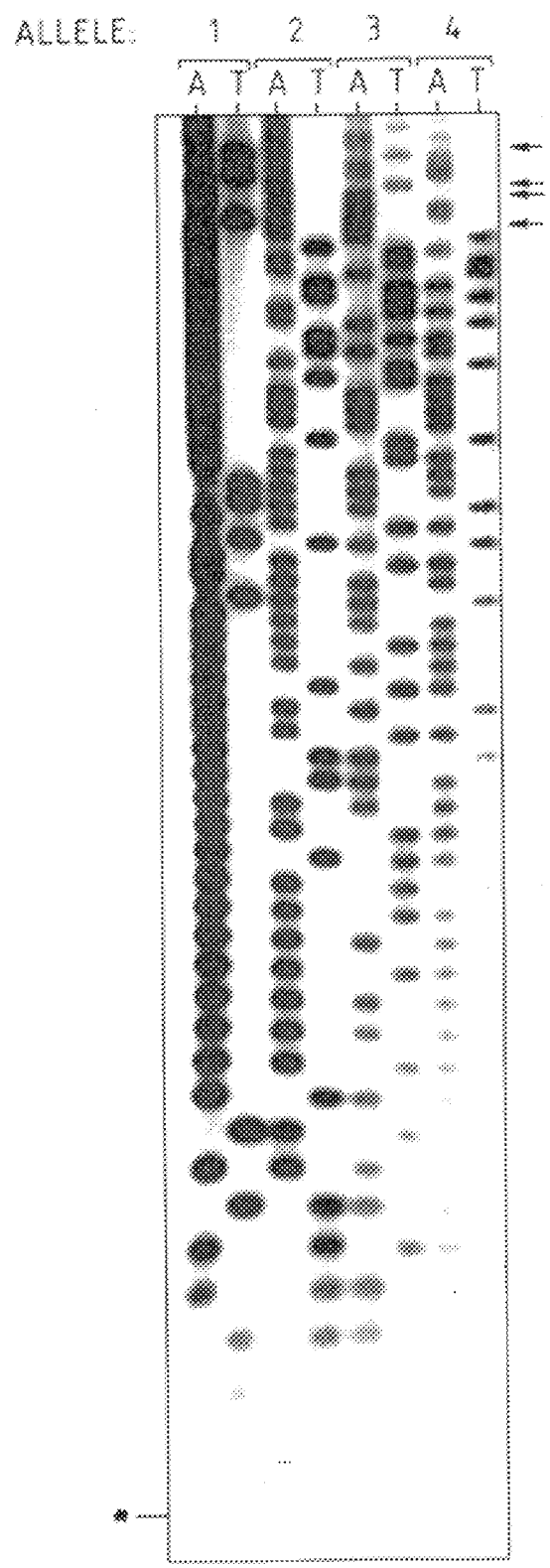
FIG. 2 illustrates examples of minisatellite allele repeat coding by MVR-PCR. MS32 alleles (4.7–18.8kb long containing 138–630 units) were separated from genomic DNA and amplified using 32-TAG-A (A) or 32-TAG-T (T) in the presence of high concentration of primers 32D and TAG. PCR products were separated by agarose gel electrophoresis and detected by Southern blot hybridization with MS32 minisatellite probe. The first repeat unit (asterisk) is weakly detected and cannot be scored reliably. Null repeat units in allele 4 which do not amplify with either 32-TAG-A or 32-TAG-T are arrowed. Methods: Human genomic DNA previously typed by Southern blot hybridization with MS32 was digested with MboI, which cleaves outside the minisatellite, and the two alleles from each individual separated by agarose gel electrophoresis and recovered by electroelution. Aliquots of fractionated DNA corresponding to 100 ng total genomic DNA were amplified in 7 µl of 45 mM Tris-HCl (ph 8.8), 11 mM $(NH_4)_2SO_4$, 4.5 mnM $MgCl_2$, 6.7 mM 2-mercaptoethanol, 4.5 µM EDTA, 1 mM dATP, 1 mM dCTP, 1 mM dGTP, 1 mM dTTP (Pharmacia), 110 µg/ml bovine serum albumin (DNase free, Pharmacia) plus 1 µM primer 32D, 1 µM primer TAG and either 10 nM 32-TAG-A or 20 nM 32-TAG-T in the presence of 0.25 unit AmpliTaq (Perkin-Elmer-Cetus). Reactions were cycled for 1.3 min at 96° C., 1 min. at 68° C., 1 min. at 70° C. for 18 cycles on a DNA Thermal Cycler (Perkin-Elmer-Cetus), followed by a chase for 1 min. at 67° C., 10 min at 70° C. for 2 cycles. The sequence of the flanking primer 32D is 5'-CGACTCGCAGATGGAGCAATG-3' (SEQ ID NO:24) (Jeffreys et al.,Cell, 1990, 60, 473–485). PCR products were electrophoresed through a 35 cm long 1% agarose (Sigma type I) gel in 89 mM Tris-borate (pH8.3), 2 mM EDTA, 0.5 µg/ml ethidium bromide alongside ΦX174 DNA x HaeIII until the 110 bp marker had reached the end of the gel. DNA was denatured, transferred by blotting onto Hybond-N (Amersham) and hybridized to $^{32}$p-labelled MS32 minisatellite probe for 3 hours at 65° C. as described previously (Wong et al., Ann. Hum. Genet., 1987, 51, 269–288). Autoradiography was for 6 hours at room temperature.

FIG. 4 illustrates MVR-PCR on total human genomic DNA. 200 ng samples of Caucasian blood DNA from 9 individuals were amplified with 32-TAG-A(A) or 32-TAG-T(T) and PCR products detected by Southern blot hybridization with minisatellite probe MS32, as described in FIG. 2 legend. The scale -1-10-20-30-40-50-60- indicates the repeat unit code position. Scoring commences at code position 1 (second repeat unit into the array). Note that the A and T tracks are completely complementary for individuals 1-5 and 7-9, and yield ternary codes where 1=aa (intense band only in A tracks), 2=tt (intense band only in T tracks) and 3=at (relative faint band in both A and T tracks). Individual 6 shows a null I-type repeat in one of his alleles, generating an aO (code 4) position (asterisk) detected as a relatively faint A track band with no band in the T track. This individual also contains a short allele of 28 repeat units, as shown by loss of code 1, 2 and 3 repeats above the arrowed position and the presence of only code 4 (aO, faint a) and code 5 (tO, faint t) repeats, equivalent to the separated allele profiles shown in FIG. 2. The presence of this short allele was confirmed by conventional Southern blot hybridization analysis of genomic DNA with MS32 (data not shown).

Figure 5A:
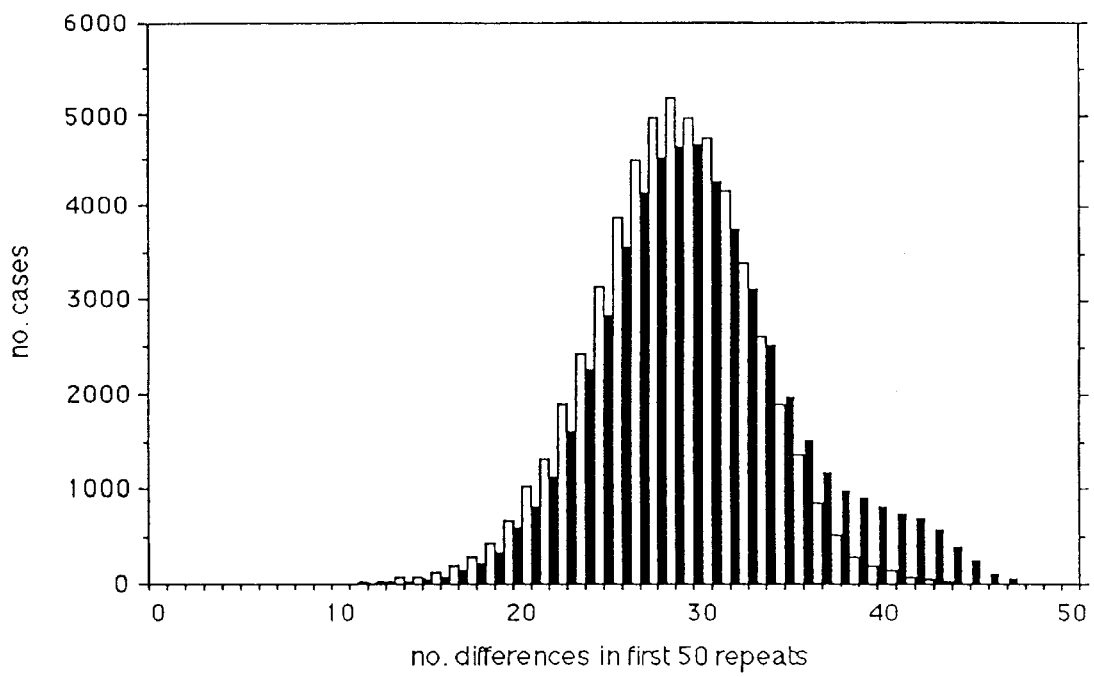
Figure 5B:
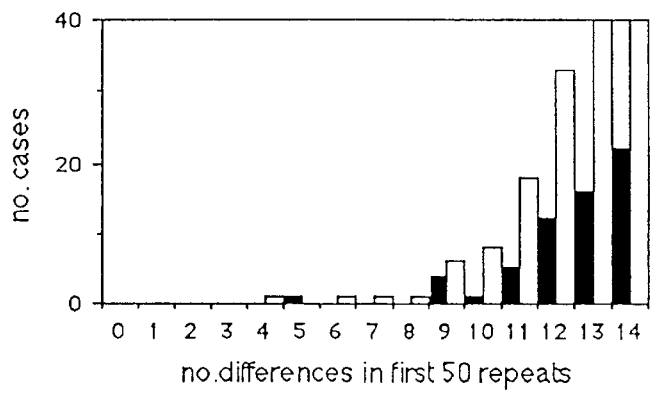

FIGS. 5A–5C illustrates individual variation in diploid MVR codes. Codes extending for at least 50 repeat units were determined for 334 unrelated individuals (177 English, 20 French, 48 Mormon, 2 Amish, 4 Venezuelan and 83 Japanese). A, filled bars, number of code differences seen over the first 50 repeat units, determined for every pairwise comparisons in total). Open bars, number of differences after removal of band intensity information, scoring code l(aa) and 4(aO) as identical and code 2(tt) and 5(tO) as indistinguishable. Mean number of differences per pair of individuals were 30.1 and 27.9 respectively. The Y axis represents the number of cases and the X axis represents the number of differences in the first 50 repeats. B, expanded plot showing the frequency distribution of the most similar pairs of MVR codes. All pairwise comparisons showed at least 4 differences over the first 50 repeats. The Y axis represents the number of cases and the X axis represents the number of differences in the first 50 repeats. C, examples of (i) the most similar and (ii) most dissimilar pairs of individuals over the first 50 repeat units, with discordances marked with "x", or ":" for discordances which rely solely on intensity differmeces. E=English, M=Mormon and J=Japanese. The complete code scored per individual is shown, together with additional differences beyond repeat unit 50. Methods: All MVR codes were determined as described in FIG. 4. 62±6 repeat units were scored per individual. Data were stroed as ASCII files and analysed using software written in VAX BASIC V3.4 and run on a VAX 8650 computer operating on VMS 5.3–1.

Figure 6A:
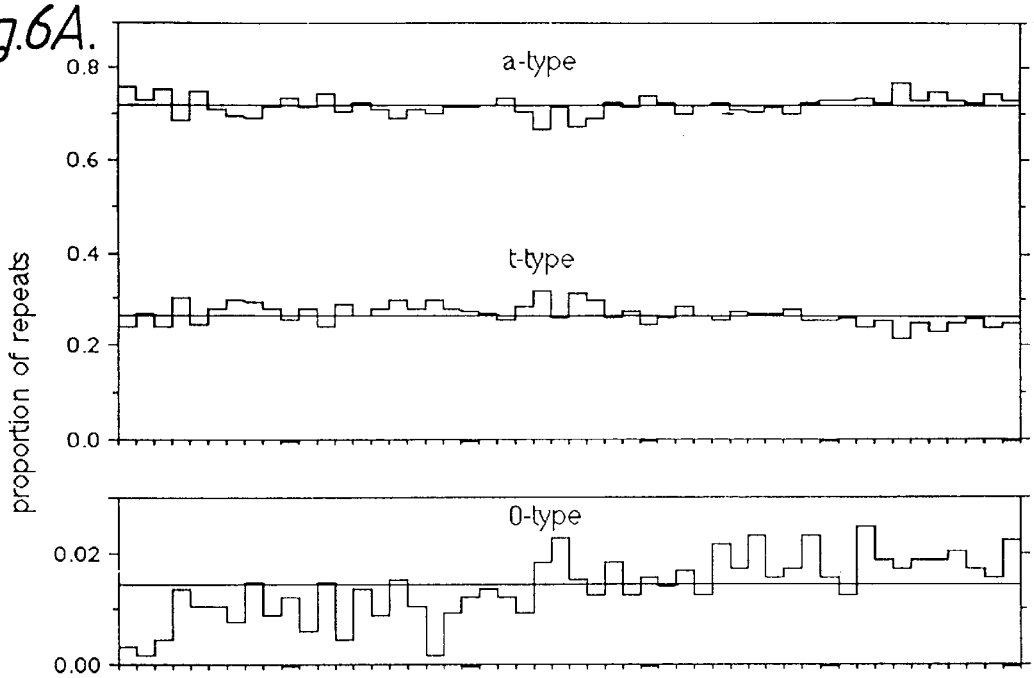
Figure 6B:
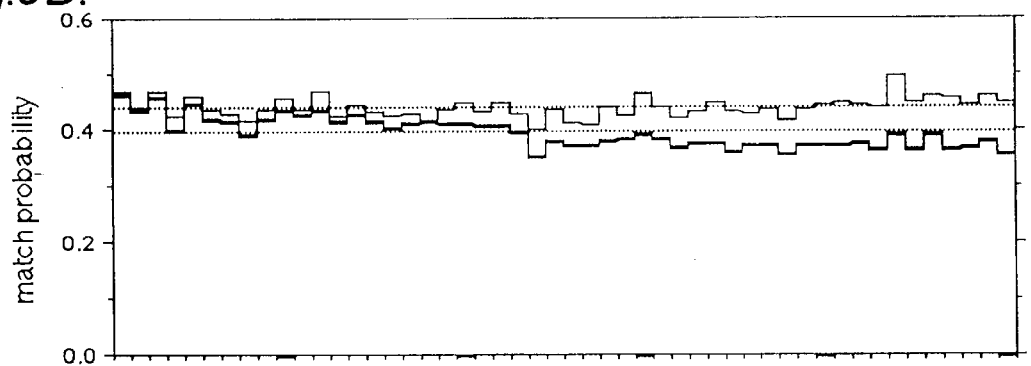
Figure 6C:
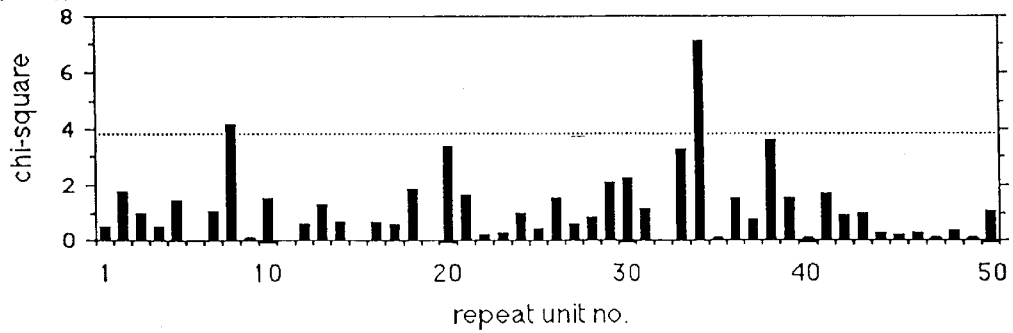

FIGS. 6A–6C shows the composition of MS32 repeat units along alleles, deterined from the diploid codes of 334 unrelated individuals (668 alleles) (ethnic composition given in FIG. 5 legend). A, frequency of a-, t- and O-type repeat units at each position along MS32 alleles. Only O-type repeat units which lay inside alleles were scored, after removing all "O-type" repeats corresponding to code positions beyond the end of short alleles. The mean proportions of a-, t- and O-type repeats (horizontal lines) and 0.721, 0.265 and 0.0144, averaged over 40,329 repeat units scored. The Y axis represents the proportion of repeats and the X axis represents the individual repeat unit positions along MS32 alleles. B, thick line, probability at each repeat position that two individuals match, determined from all pairwise comparisons of the 344 individuals. Thin line, corresponding probabilities determined after removing band intensity assumptions by scoring code 1(aa) and 4(aO) as indistinguishable, and code 2(tt) and 5(tO) as the same. The mean match probabilities per repeat position (dotted lines) are 0.395 and 0.439 respectively. The Y axis represents the match probability and the X axis represents the individual repeat unit positions along MS32 alleles. C, test for departure from Hardy-Weinberg equilibrium at each repeat position, after converting each repeat position to a dimorphism ("alleles" a and t+O) and determining the $X^2$ statistic (1 d.f.) for deviation of observed genotype frequencies (aa, a(t+O), (t+O) (t+O)) from those expected from the repeat unit composition at each repeat position. The 5% significance level is given by a dotted line. The Y axis represents chi-square and the X axis represents the repeat unit number.

FIG. 7 shows the reconstruction of the MVR codes of individual MS32 alleles by pedigree analysis. 1, incomplete reconstruction of the haplotypes of all four parental alleles using a single child in an English family (f=father, m=mother and c=child The paternal and maternal alleles transmitted to the child are labelled A and C, and the non-transmitted alleles B and D. Parental haplotypes can be deduced, assuming no recombination between parental alleles, at all positions except where the father, mother and child are heterozygous for the same repeat unit types (i.e. all individuals share either code 3(at) or 4(aO) or 5(tO)). Such ambiguities are indicated by "?". 2, complete reconstruction of allele maps using the large sibship of CEPH family 104 (f=father, m=mother, c=children). The children show four different diploid codes, corresponding to the four possible combinations of parental alleles, with no allelic mutation in any of the offspring. The mother unusually contains two short alleles, resulting in coding state 6(OO) beyond the end of the longer allele. The resulting haplotypes (alleles C and D) terminate in a string of "null" (nonexistent) repeats. Both of these alleles have been mapped by partial digestion with HaeIII (in bold) giving maps fully consistent with those extracted from the diploid codes. Methods: Haplotypes were extracted using software written in VAX BASIC V3.4. Diploid codes of the father, mother and each child were entered. For a family with a single child, the four parental haplotypes were extracted sequentially along each position of the diploid code. For each position, the code of the father, mother and child were noted and checked in a look-up table to determine whether exclusions exist, and if not, to determine the repeat unit types transmitted or not from each parent to the child. For example, if the father is 1(aa), mother 3(at) and child 3(at), then no exclusions exist and the repeat units at that position on each allele is given by allele A, a; allele B, a; allele C, t; allele D, a. Similarly, codes father 3(at)+mother 5(tO) +child 4(aO) give A, a; B, t; C, 0; D, t. In contrast, codes 1(aa)+2(tt)+5(tO) give a paternal mutation/exclusion. Since there are 7 possible coding states per individual (codes 1–6 plus "?" for repeat positions where the scoring is uncertain), the look-up table contains 7³=343 entries corresponding to every possible combination of codes in the mother, father and child. For families with more than one offspring, the incomplete haplotype of each parental allele was extracted from each child as described above for the single child family. The incomplete haplotypes from each parent were then compared to identify matching alleles deduced from different children and to deduce which parental allele had been transmitted to each child. The consensus haplotype of each allele was then determined from the incomplete haplotypes deduced from each child, thereby removing all uncertain positions. Finally, the diploid code of each individual was compared with the code predicted from the two constituent alleles, as a final check to ensure full condordance of all diploid codes and haplotypes. The deduced haplotypes were stored in an ASCII file to generate an MS32 allele database. Note that this approach also enables allele reconstruction where one parent is missing, by entering the code of the missing parent as "???. . . ".

FIG. 8 shows the frequencies of different MS32 alleles defined by MVR mapping. A, incidence of different alleles in a sample of 254 Caucasian MS32 alleles mapped from separated alleles (FIG. 2) or by pedigree analysis (FIG. 7). N=number of different alleles and T=no of times observed in sample of 254 alleles. The allele database contained 109 English, 40 French, 95 Mormon, 4 Amish and 6 Venezuelan alleles, of which 100 alleles were deduced from single child families and were therefore incomplete. 63+5 repeats were determined per allele. All pairwise combinations of alleles (32, 131 comparisons in total) were checked for identity. *, one pair of indistinguishable alleles occurs in the CEPH homozygote 3710, and another pair are shared by CEPH Amish parents 88401 and 88402. B, examples of indistingishable alleles shared by unrelated individuals. Note that the English allele is incompletely mapped at positions marked ":". F=French, M=Mormon and E=English. C, examples of similar but non-identical pairs of alleles, with differences marked X. Similar pairs of alleles were identified by searching all pairwise comparisons of alleles for pairs with small numbers of differences exist between the MVR codes of a randomly picked pair of alleles. In total, 10 examples of groups of 2–4 alleles with closely related in-phase MVR maps were identified among the 254 alleles analysed.

FIG. 9 shows the analysis of MS32 mutant alleles detectable in pedigrees. 1. Example of CEPH pedigree showing a child with a mutant allele. Maps of parental alleles A–D were deduced from 7 non-mutant offspring (not shown). Comparison of the diploid code of child 141606 with the parents shows 4 specifically paternal exclusions (p) plus 3 ambiguous exclusions (e) which do not indicate the parental origin of the mutant allele. There are no maternal exclusions, and thus the child has inherited a mutant paternal allele and non-mutant maternal allele. The diploid code of the child is compatible with the child having inherited maternal allele C but not D. Subtraction of the code for allele C from the diploid code of the child yields the code for the mutant paternal allele. Comparison of the mutant allele with paternal alleles A and B indicates that this allele commences with the code of allele A and then switches to the beginning of the code of allele B after two a-type repeats of unknown origin. This allele therefore appears to have arisen by unequal crossing over between the two paternal alleles, as indicated, with possible cross-over sites marked X. F=father, M=mother, ch=child, m=mutant, mu=deduced mutant allele 2, summary of mutant alleles detected in the CEPH panel of families, based on the analysis of 286 offspring from large sibships. This survey has detected all allele length change mutations previously detected by Southern blot analysis of AluI digests of genomic DNA (Armour et al., 1989), plus three new hitherto-undetected mutations resulting from gains of a single repeat unit. In all cases, the change in repeat unit copy number is consistent with allele length changes detected by Southern blot analysis (not shown). mu=mutation, ma=maternal, pa=paternal, CEPH=CEPH individual, (i)=change in repeat unit copy number, (ii)= detected on Southern Blot, (iii)=mechanism and in=intraallelic. The mutation rate =7/572 per gamete =0.0122 (95% confidence limits 0.006–0.023). 3, possible locations of unequal exchange points on the donor allele (the allele which contributes to the beginning of the mutant allele) and the recipient allele, as shown for mutant e in (1) above. For presumptive intra-allelic (sister chromatid) unequal exchange, the donor and recipient alleles are identical. D=donor, R=recipient, mu=mutation and rp=repeat position.

Figure 10:
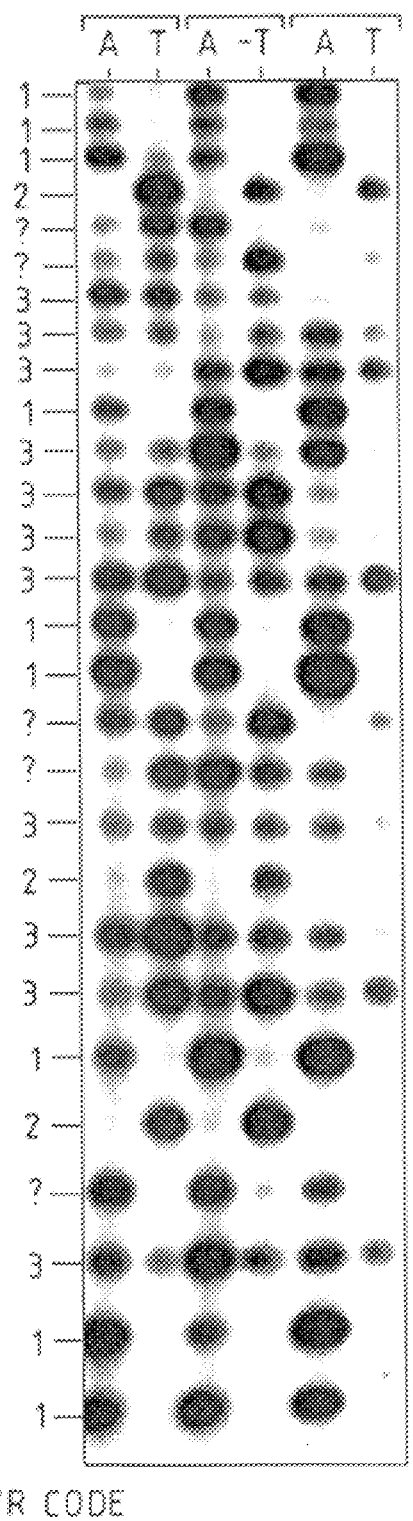

FIG. 10 illustrates MVR-PCR analysis of trace amounts of human genomic DNA. An individual was selected from a collection of 450 typed people, and his identity hidden from the analyst. Three pairs of 100 μg aliquots of genomic DNA from this individual were amplified by MVR-PCR for 28 cycles using 32-TAG-A(A) or 32-TAG-T(T) and the PCR products detected by Southern blot hybridization. Zero DNA controls gave no signal (not shown). The incomplete MVR code shown of the unknown individual was established from all repeat positions which gave concordant typing results in all three analyses. Repeat positions which have ambiguous typing results due to band "drop-out" were scored as "?", as shown. Note that band intensity fluctuations prevent the discrimination of codes l(aa) and 4(aO), and codes 2(tt) and 5(tO). An incomplete MVR code which could be determined over the first 45 repeat positions was then compared against all 450 individuals in the database (allowing for equivalence of codes 1,4 and codes 2,5). The correct individual was identified as the only database entry which showed a complete match with the incomplete MVR code.

Figure 11:
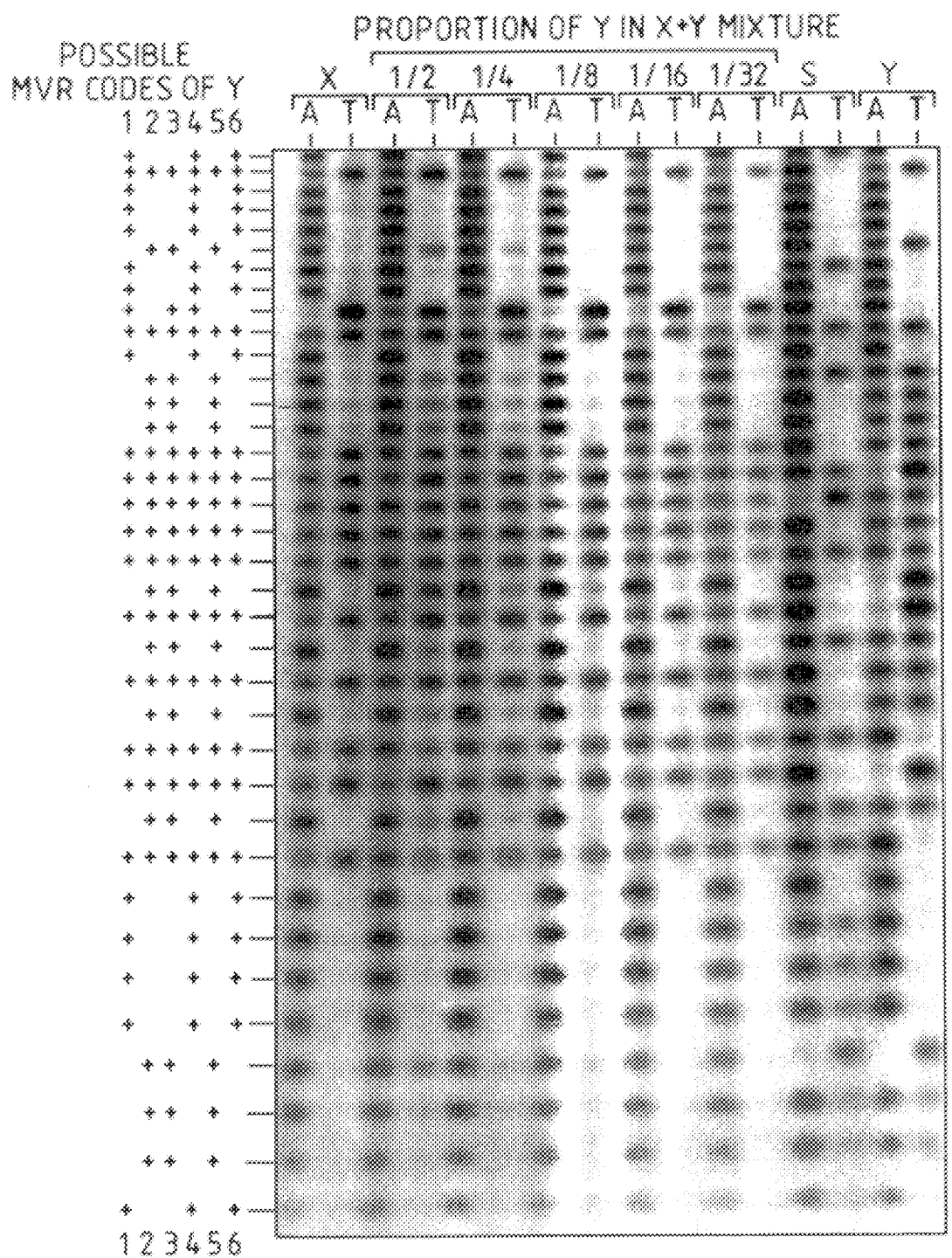

FIG. 11 illustrates incomplete MVR code information recoverable from mixed DNA samples. Two individuals (X,Y) were chosen at random from a collection of 450 typed people, and their identities were concealed from the analyst. 100 ng samples of genomic DNA from X and Y or from X plus Y mixed in the indicated proportions, were amplified by MVR-PCR for 18 cycles and PCR products detected by Southern blot hybridization. S, standard individual included on all gels. By compairing the MVR-PCR profile of X with the profile of the mixed DNA samples, possible genotypes of Y can be deduced, as indicated, at all repeat positions where X is not code 3(at), by checking for A- or T-track specific bands present in the mixture but not X. The MVR code of X and the incomplete and ambiguous MVR code of Y deduced from the mixed DNA samples were screened across the database of 450 individuals to reveal, correctly and uniquely, the identities of X and Y.

Figure 12:
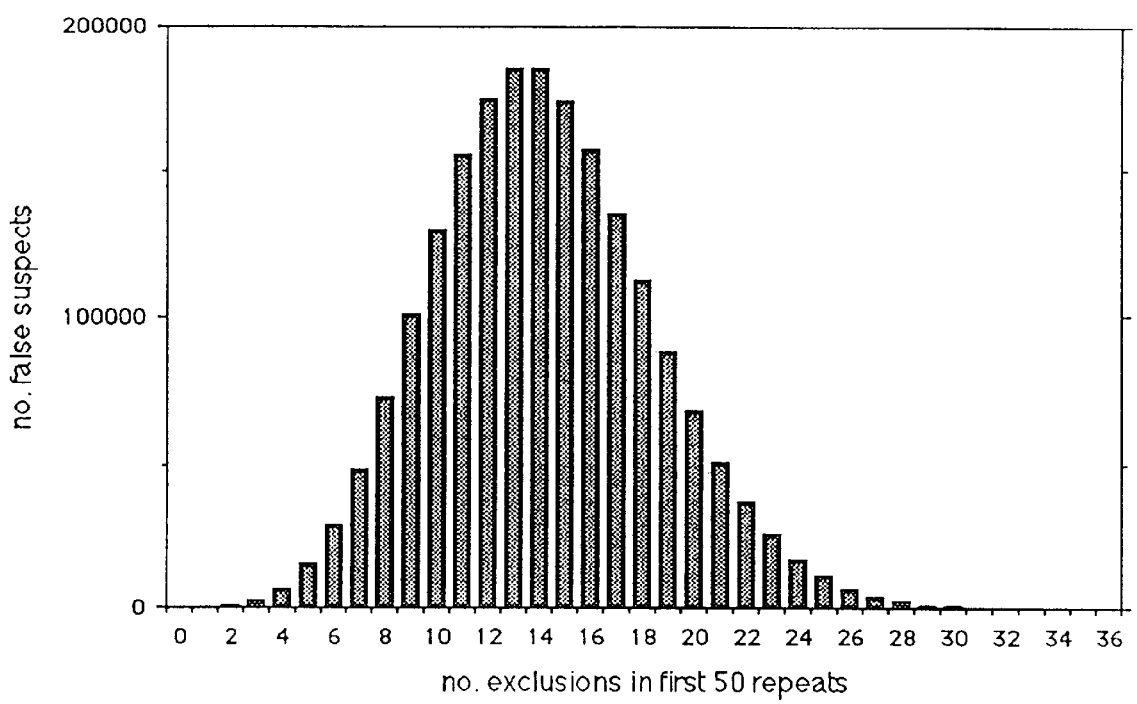

FIG. 12 shows the efficiency of individual identification by MVR-PCR analysis of mixed DNA samples. The ambiguous MVR code of an "assailant" was deduced from the diploid MVR codes of a "victim" and admixed "assailant", both selected at random from a database of 334 unrelated individuals (see FIG. 5 legend for ethnic composition). The ambiguous code was then compared with the MVR codes of each of the 332 other individuals ("false suspects") in the database, and the number of exclusions over the first 50 repeat units which eliminated each "false suspect" as assailant were determined. The exclusion frequency distribution is given for a total of 6000 "victim" plus "assailant" pairs (1,992,000 "false suspects" in total). There were on average 14.2 exclusions per "false suspect", and only 14 cases in total where a "false suspect" failed to be excluded, giving a mean non-exclusion rate of $7.0 \times 10^{-6}$ per "false suspect". The Y axis represents the number of false suspects and the X axis represents the number of exclusions in the first 50 repeats. Methods: The ambiguous MVR code of the "assailant" which could be deduced from a mixed DNA sample was determined by comparing the MVR codes of the "victim" (V) and "assailant" (S) (see FIG. 11). For example, if both V and S are code 1(aa), then neither V nor a V+S mixture will show a band in the T-track, whence the ambiguous code deducible for S from the mixture, given that the code of V is known is code 1(aa), 4(aO) or 6(OO). Similarly, if V is code 1(aa) and S is code 3(at), then the mixture, but not V, will show a band in the T-track, whence the ambiguous code deducible for S is code 2(tt), 3(at) or 5(tO). In contrast if the victim is code 3(at), then in the V+S mixture both the A- and T-tracks will contain a band, irrespective of the genotype of S, and thus the deduced code of S at that repeat position will be totally ambiguous. The incomplete code of S deducible from each V+S combination was then compared with each non-S database entry ("false suspect", FS) to determine whether definitive exlusions exist. For example, if the ambiguous code of S is code 1(aa), 4(aO) or 6(OO) and if FS is code 4(aO), then no exclusion exists; in contrast, if FS is code 3(at), then an exclusion is scored. This analysis only uses informtion on the presence or absence of bands from the A- and T- tracks, and does not include additional information on relative band intensities in V and the V+S mixture.

Figure 13C:
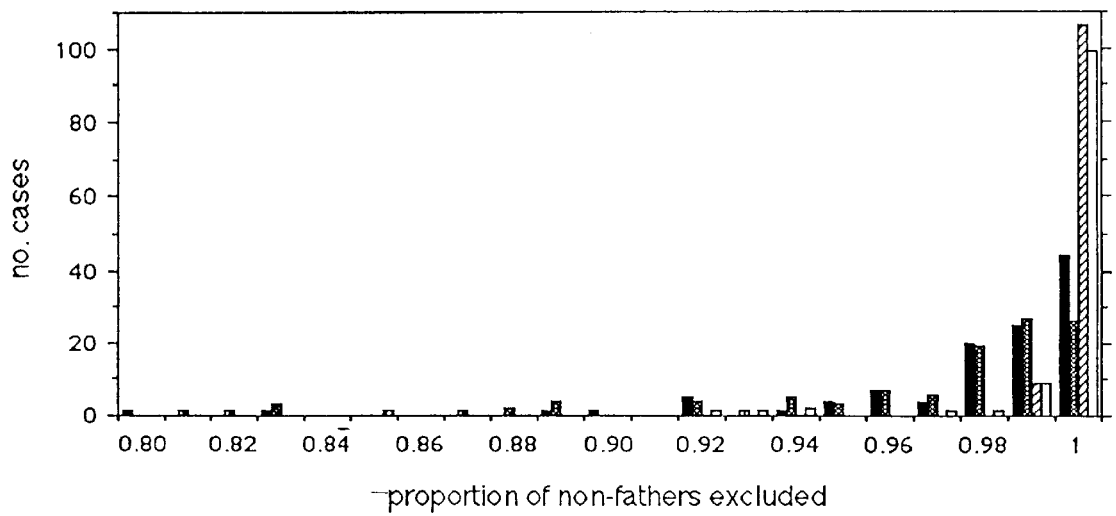
Figure 13A:
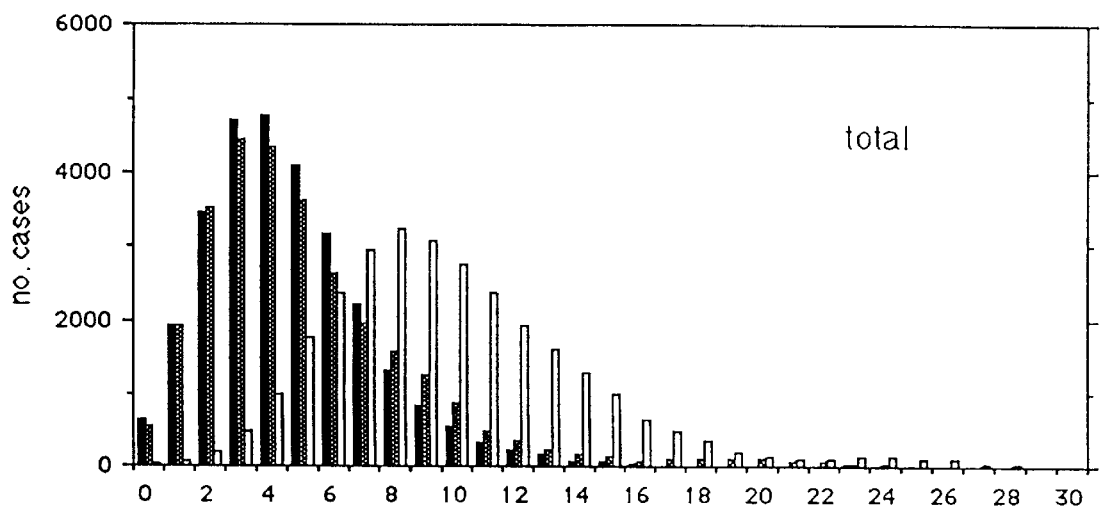
Figure 13B:
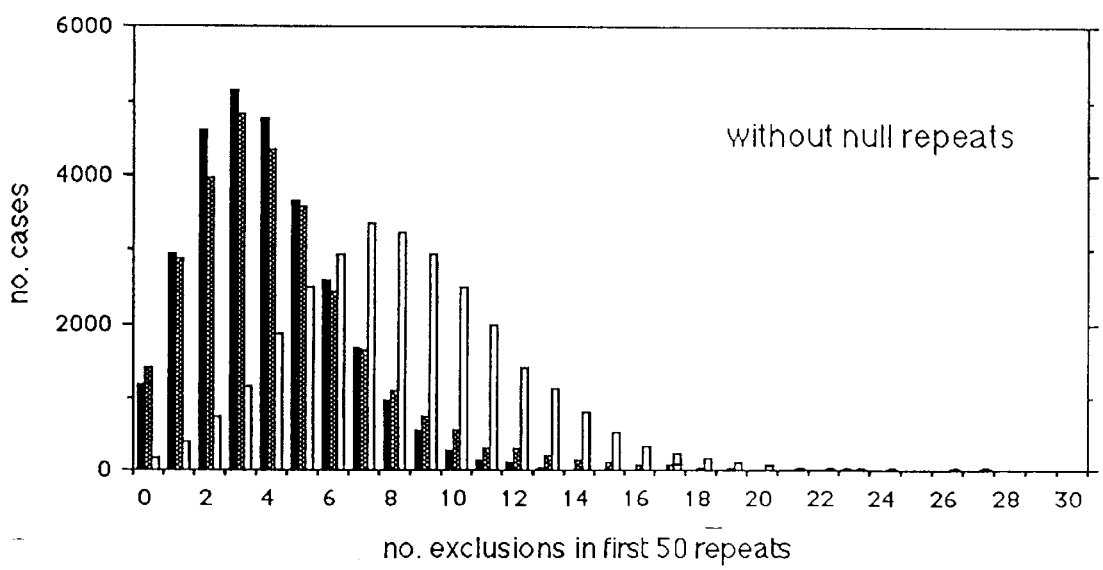

FIGS. 13A–13C shows the efficiency of MS32 diploid codes in paternity testing. Diploid codes extending for at least 50 repeat units were obtained from 115 Caucasian mother-father-child trios. For each trio, the father was removed and replaced sequentially by each of 249 different Caucasian individuals ("non-fathers"). The MVR codes of each mother-child plus non-father trio were analysed over the first 50 repeat units to determine the total number of repeat unit positions which gave an exclusion, plus the number of paternal-specific exclusions and the number of exclusions which were directionally ambiguous (e.g. moether and non-father both code 1(aa), child code 3(at)). A, frequency distribution of paternal-specific exclusions (filled bars), ambiguous exclusions (shaded bars), and total exclusions (open bars) for each of the 28,635 combinations of mother-child and non-father. The mean number of exclusions was 4.67, 5.19 and 9.86 per child, respectively. The overall proportion of non-fathers showing no exclusions, or no paternal-specific exclusions, was 0.00229 and 0.0113 respectively. The Y axis represents the number of cases and the X axis represents the number of exclusions in the first 50 repeats. B, frequency distributions as in (A) determined after eliminating all child code positions containing an O-type repeat (code 4, aO; code 5, tO; code 6, OO). On average, 3.93 paternal-specific, 4.30 ambiguous and 8.23 total exclusions were obtained per trio. 0.00534 of non-fathers showed no exclusions, and 0.0414 showed no paternal-specific exclusions. The Y axis represents the number of cases and the X axis represents the number of exclusions in the first 50 repeats. C, variation in the number of non-fathers excluded for each of the 115 mother-child combinations. Filled bar, non-fathers eliminated by paternal-specific exclusions. Shaded bar, men showing paternal-specific exclusions after elimination of all O-type repeat positions in the child's code. Hatched bar, non-fathers showing any exclusion (paternal-specific plus ambiguous). Open bar, non-fathers with any exclusion after elimination of O-type repeats from the child. The Y axis represents the number of cases and the X axis represents the proportion of non-fathers excluded.

Figure 14A:
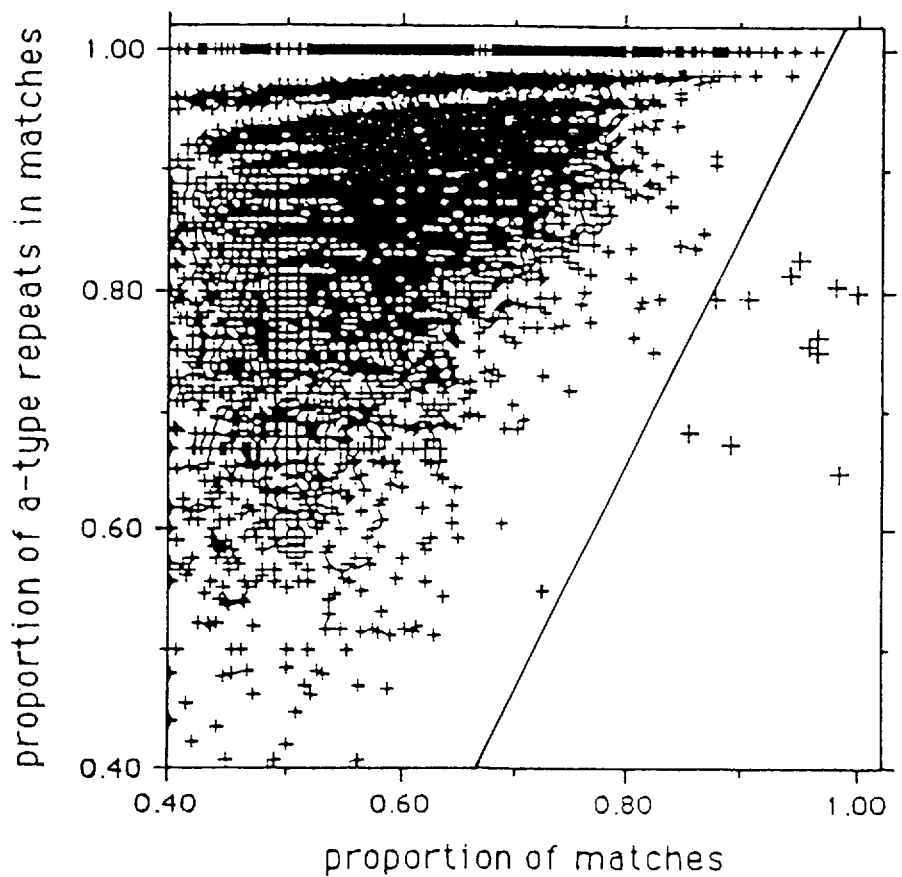

FIGS. 14A–14B shows similarities between different MS32 alleles. A, identification of related alleles. Every pairwise comparison of the MVR haplotypes of 326 different Caucasian alleles was analysed for the proportion of matching repeat positions and the proportion of matches which were a-type repeats. For each pair of alleles, comparisons were repeated for alleles misaligned up to ±10 repeat units out of register (total $2.2 \times 10^6$ comparisons). The plot shows data on 10,000 such comparisons and the presence of a separate grouping of allele pairs to the right of the diagonal line which show significant pairwise similarity. The Y axis represents the proportion of a-type repeats in matches and the X axis represents the proportion of matches. B, examples of groups of related alleles so identified, with gaps (−) introduced to improve alignment. M=Mormon, F=French and B=British individuals. Haplotypic MVR map segments shared by related alleles are shown in uppercase and divergences by lowercase. Additional haplotypes shared by some grouped alleles are underlined. Some alleles have been mapped using single offspring and therefore show uncertain positions.

Figure 15A:
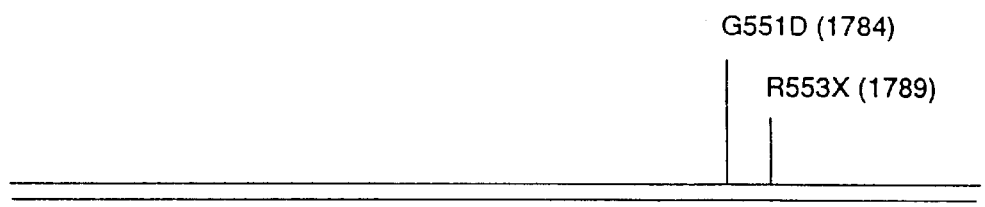
Figure 15B:
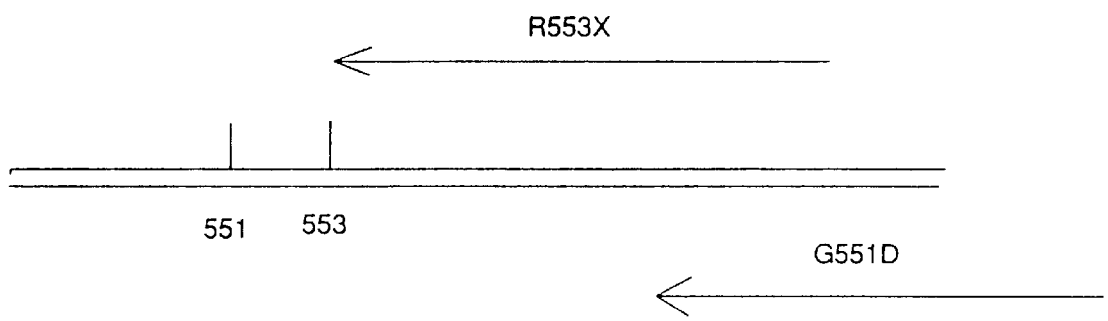
Figure 15C:
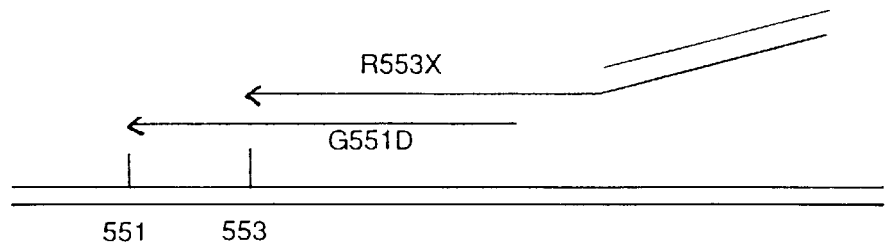

FIGS. 15A–15C shows the use of tailed primers and TAG sequences in the simultaneous detection of cystic fibrosis (CF) mutations. In (a) the mutations are indicated as G551D and R553X in exon 11 of the CFTR gene. In (b) the extended R553X primer (indicated as R553X) is bound and masks G551D target so that the shorter G551D primer (indicated as G551D) is blocked. In (c) both the G551D and R553X primers are bound and the use of a tail sequence can be used to increase the length of the R553X primer.

Figure 16:
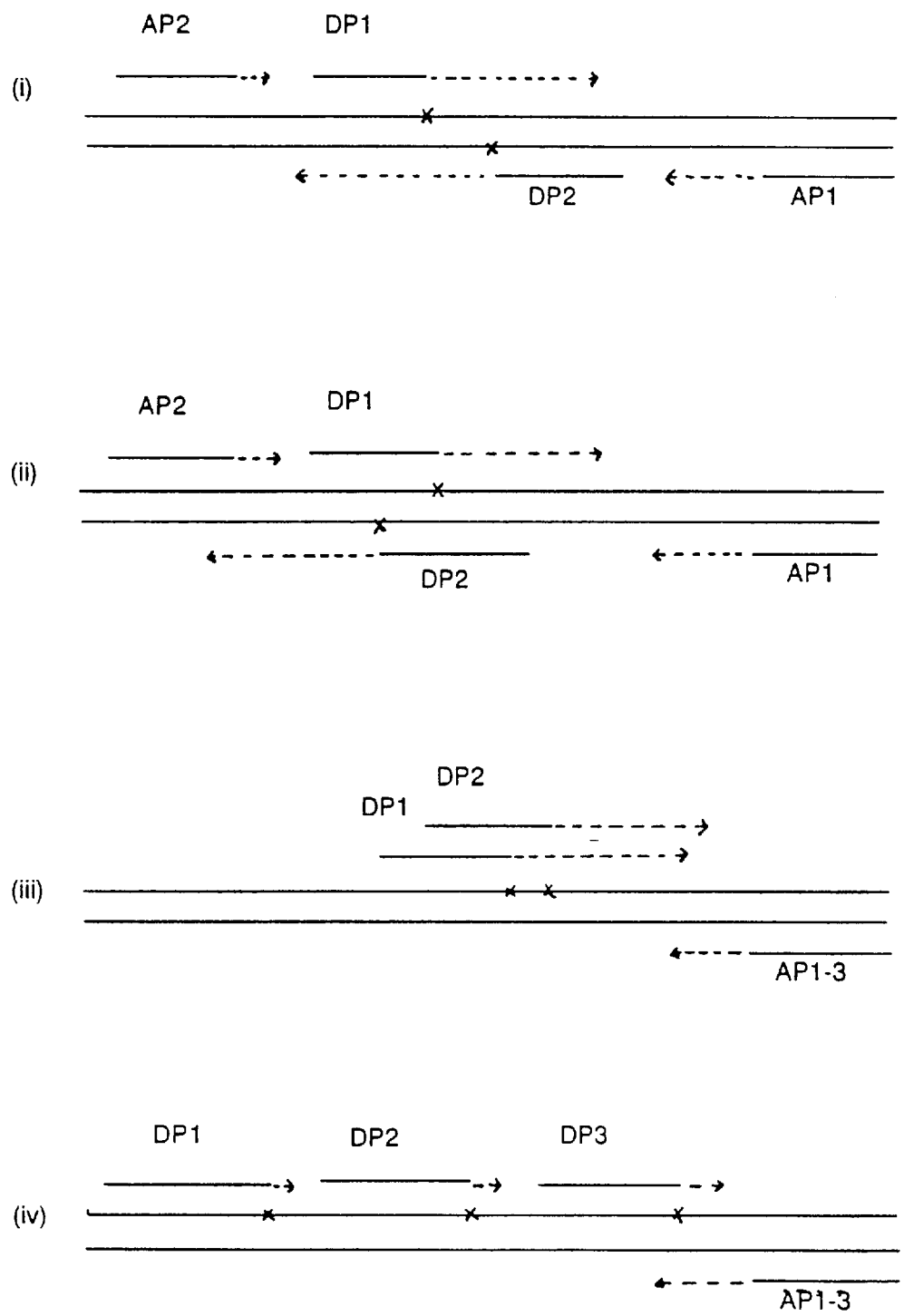

FIG. 16 illustrates convenient arrangements for diagnostic primers (DP1-3) and corresponding amplification primers (AP1-3) used in overARMS. In (i), (iii) and (iv) the primers (DP1-DP3) are provided on the same target base sequence. In (iii) and (iv) the primers comprise a complementary overlap. In (ii) the primers comprise a complementary overlap but are on different target base sequences.

FIG. 17 shows minisatellite allele repeat coding and detection of N-type repeats by MVR-PCR on total genomic DNA. Each individual DNA sample (1-5) was amplified using 32-TAG-A (A), 32-TAG-T (T) or 32-TAG-N (N) - sequences given in Table 3 hereinafter, together with driver primers 32-O and TAG. PCR products were resolved by agarose gel electrophoresis and detected by Southern blot hybridisation with $^{32}$P-labelled MS32 repeat probe. The vertical scale 1-10-20-30-40-50-60- indicates the code positions for the individual repeat units. Arrows indicate positions heterozygous for U-type null repeats not amplified by 32-TAG-N. Individual 4 has two short alleles, on terminating at position 27 and the other at position 86 (marked with circles).

Figure 18A:
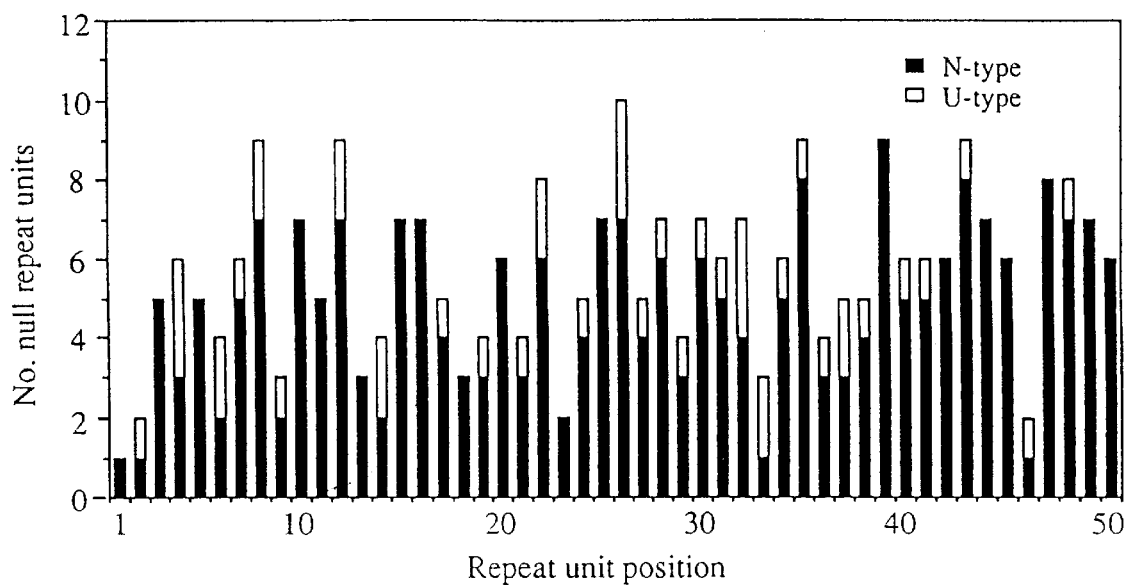
Figure 18B:
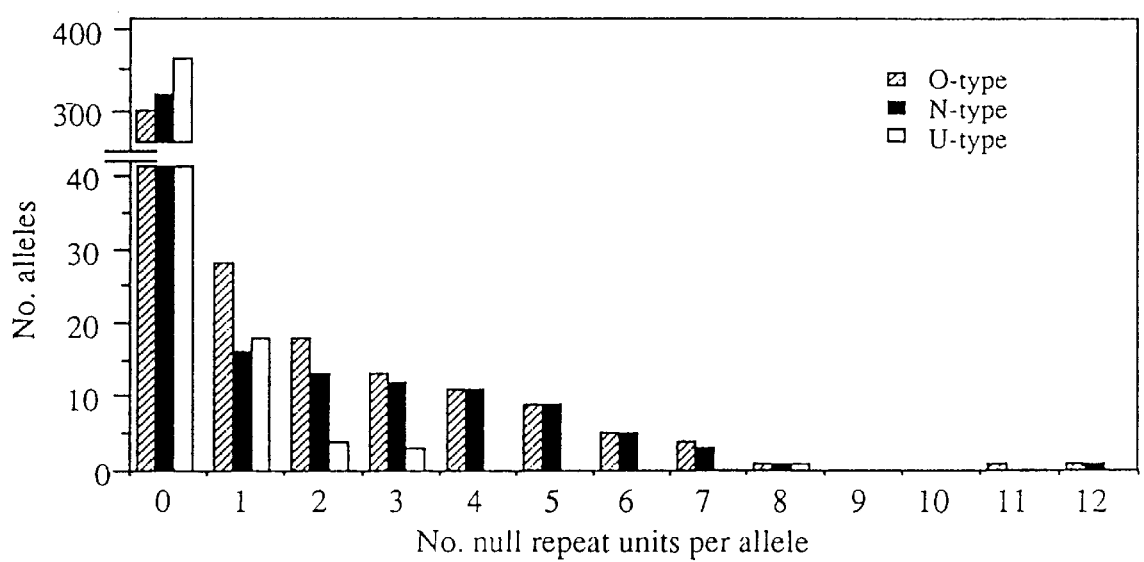
Figures 18C, 21:
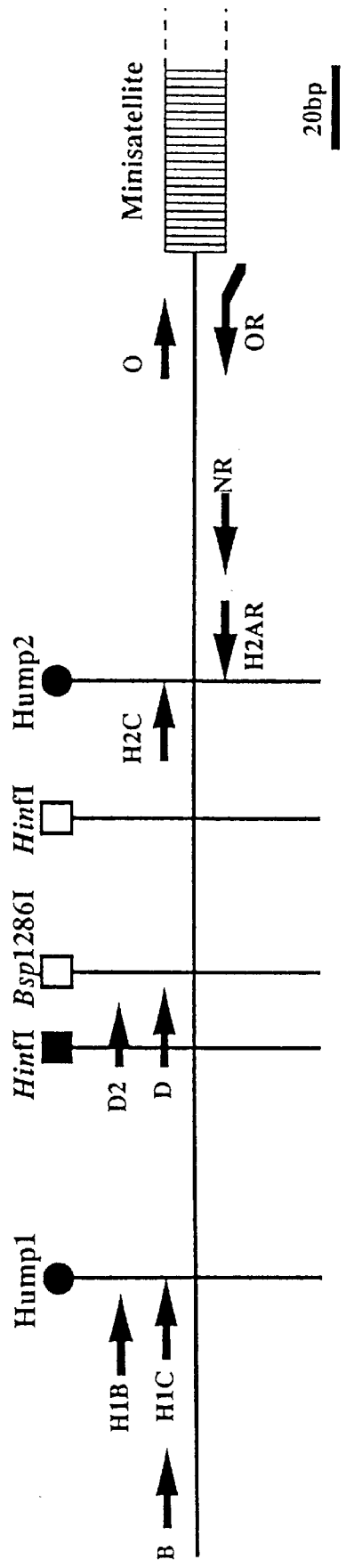

FIGS. 18A–18C shows distribution of null repeats in MS32 alleles. A: the incidence of N-type and U-type null repeat units at each position over the first 50 repeat units of 391 different MS32 alleles (331 Caucasian and 60 Japanese). The Y axis indicates the number of null repeat units and the X axis indicates the repeat unit positions. The black portion of the individual bars represent N-type units and the white portions represent U-type units. B: variation in the number of null repeat units within the first 50 repeats of 391 different MS32 alleles. Distributions are shown for N-type, U-type and total O-type repeats. The Y axis represents the number of alleles and the X axis represents the number of null repeat units per allele. The black bars represent N-type units, white bars represent U-type units and hatched bars represent O-type units. C: examples of English alleles (E) containing unusual arrangements of null repeat units.

FIG. 19 shows examples of group of aligned alleles containing null repeats. Groups of alignable alleles were identified as previously described, allowing for misalignments between the beginnings of different alleles. Common haplotypic segments shared by different alleles are shown in uppercase, and the positons of null repeat units are indicated by '+' for N-type repeats and '*' for U-type repeats. High-order repetitive structures within alleles are arrowed. Some alleles maps were derived from the diploid codes of single child-mother-father trios and thus contain ambiguous positions (marked "?"). E=English, F=French, J=Japanese, M=Mormon, B=Bangladeshi.

Figure 20A:
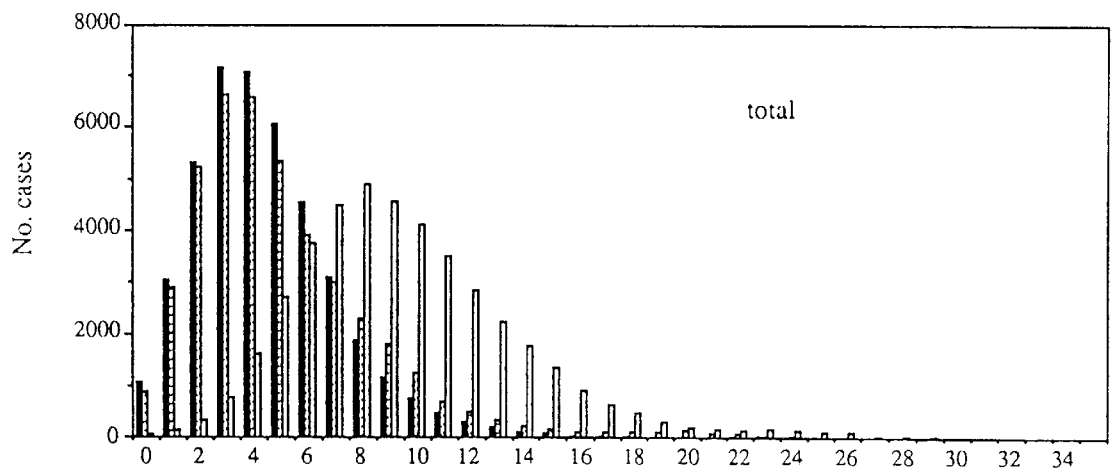
Figure 20B:
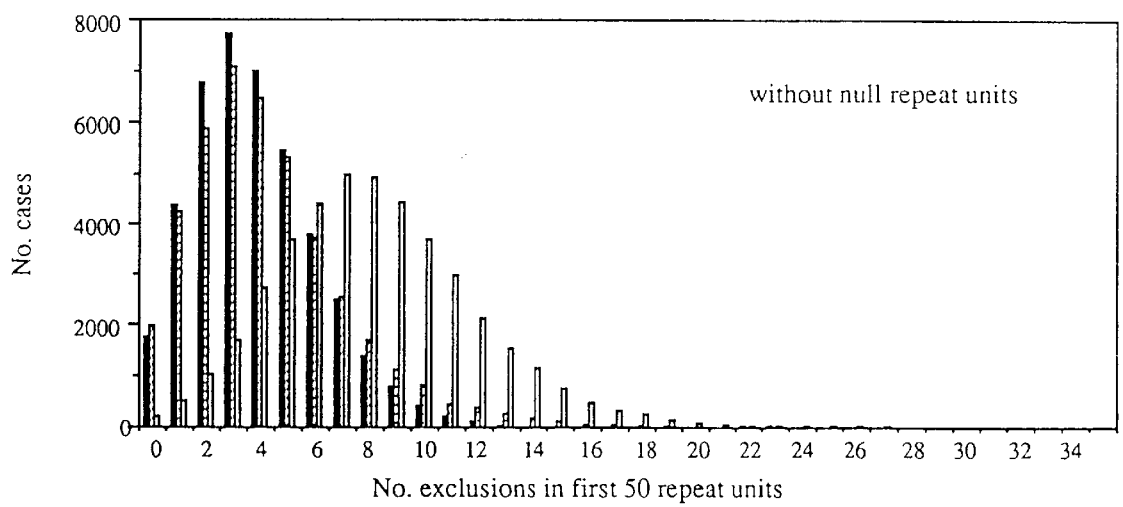
Figure 20C:
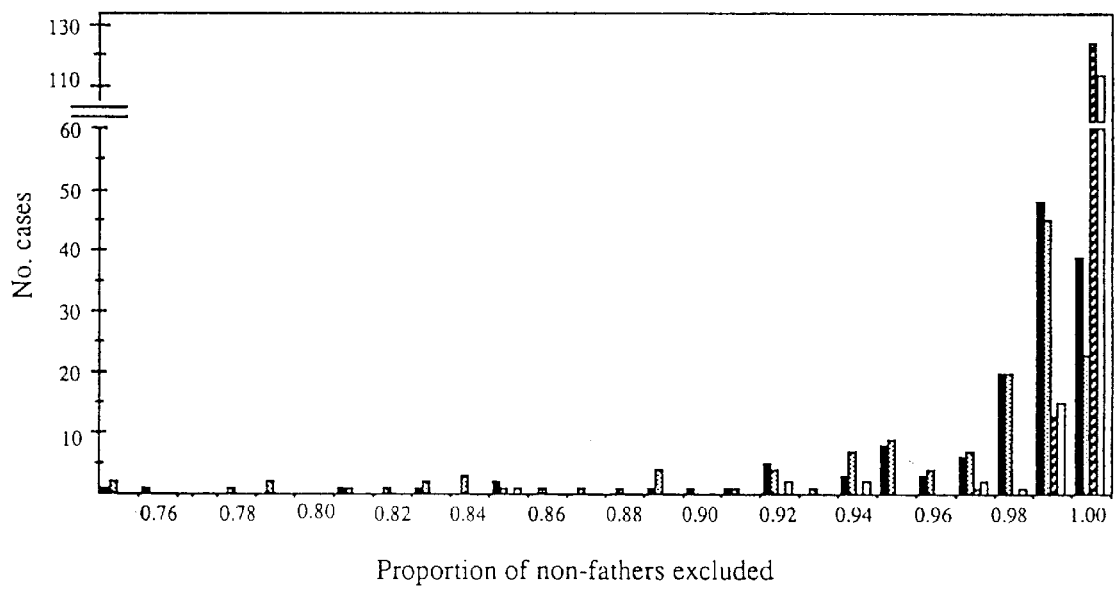

FIGS. 20A–20C shows the efficiency of MS32 diploid codes and the effects of null repeats in paternity testing. Diploid codes extending for at least 50 repeat units were obtained from 141 Caucasian mother-father-child trios. For each trio, the father was removed and replaced sequentially by each of 302 different Caucasian individuals ("non-fathers"). The MVR codes of each mother-child plus non-father trio were analysed over the first 50 repeat units to determine the total number of repeat unit postions which gave an exclusion, plus the number of paternal-specific exclusions and the number of exclusions which were directionally ambiguous (eg. mother-and non-father both a/a, child a/t). A: frequency distribution of paternal-specific exlusions (filled bars), ambiguous exclusions (shaded bars), and total exclusions (open bars) for each of the 42,582 combinations of mother-child and non-father. The mean number of exclusions was 4.67,5.19 and 9.86 per child, respectively. The overall proportion of non-fathers showing no exclusions, or no paternal-specific exclusions, was 0.14% and 2.5% respectively. The Y axis represents the number of cases and the X axis indicates the number of exclusions in the first 50 repeat units. B: frequency distributions as in (A) determined after eliminating all child code positions heterozygous for an O-type repeat (a/O, t/O). On average, 3.93 paternal-specific, 4.30 ambiguous and 8.23 total exclusions were obtained per trio. 0.50% of non-fathers showed no exclusions, and 4.1% showed no paternal-specific exclusions. The axes are identical. C: variation in the number of non-fathers exclused for each of the 141 mother-child combinations. Filled bar, non-fathers eliminated by paternal-specific exclusions. Shaded bar, men showing paternal-specific exclusions after elimination of all heterzygous O-type repeat postions in the child's code. Hatched bar, non-fathers showing any exclusion (paternal-specific plus ambiguous). Open bar, non-fathers with any exclusion after elimination of O-type repeats from the child. The Y axis represents the number of cases and the X axis represents the proportion of non-fathers excluded.

FIG. 21 shows a diagrammatic representation of the MS32 5'-flanking region, showing polymorphic sites and PCR primers. Filled circles represent polymorphic base substituions, open squares non-polymorphic restriction sites and filled squares polymorphic restiction sites. Arrows indicates PCR primers. PCR primer sequences are:

32-OR 5'-tcaccggtgaattcACCACCCTTCCCACCAAAC-TACTC -3'(SEQ ID NO: 37),

32-H2AR 5'-GTGCAGTCCCAACCCTAGCCA -3'(SEQ ID NO: 23),

32-H2C 5'- TGATGCGTCGTTCCCGTATC -3'(SEQ ID NO: 16),

32-D2 5'- CGACTCGCAGATGGAGCAATG -3'(SEQ ID NO: 24),

32-D 5'- CGACTCGCAGATGGAGCAATGGCC -3'(SEQ ID NO: 25),

32-H1C 5'- TGGTGCTGCAAAAGAAATAC -3'(SEQ ID NO: 14),

32-H 1B 5'- TTTGGTGCTGAAAAGAAAG -3'(SEQ ID NO: 5),

32-NR 5'- AGTAGCCAATCGGAATTAGC -3'(SEQ ID NO: 15) and

32-B 5'- TAAGCTCTCCATTTCCAGTTTCTGG -3'(SQ ID NO: 30).

32-OR carries a 14bp 5' extension (lower case, incorporating cloning sites) which is nonessential for the work described here. M represents the MS32 minisatellite.

Figure 22A:
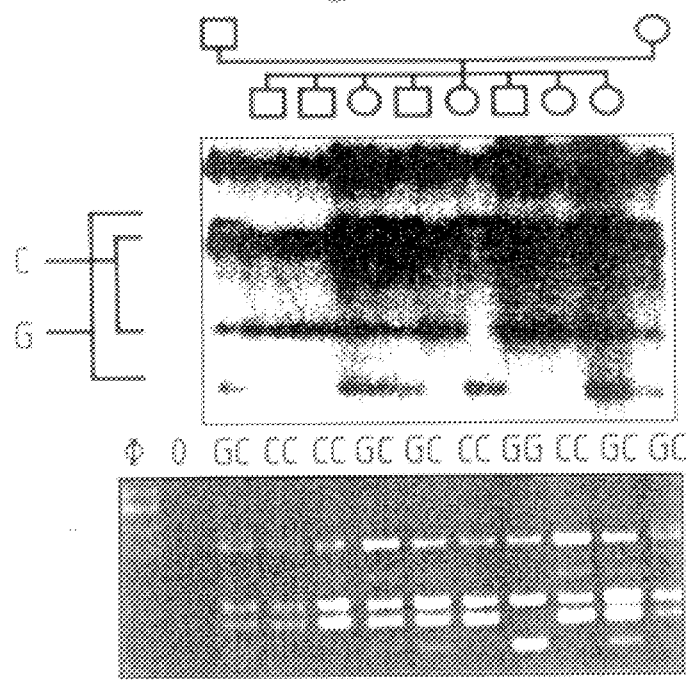
Figure 22B:
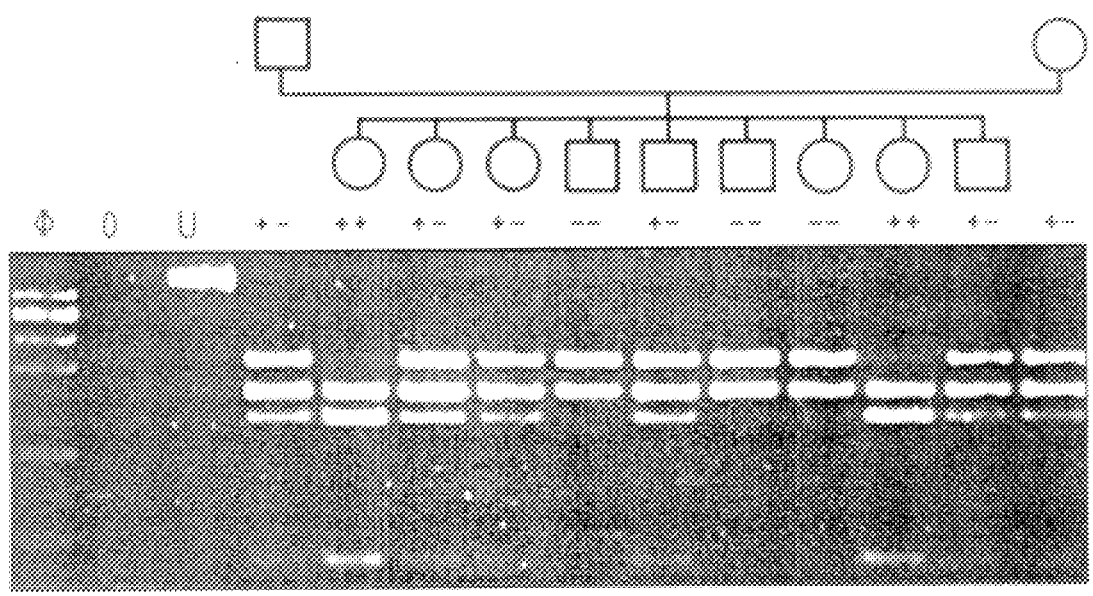
Figure 22C:
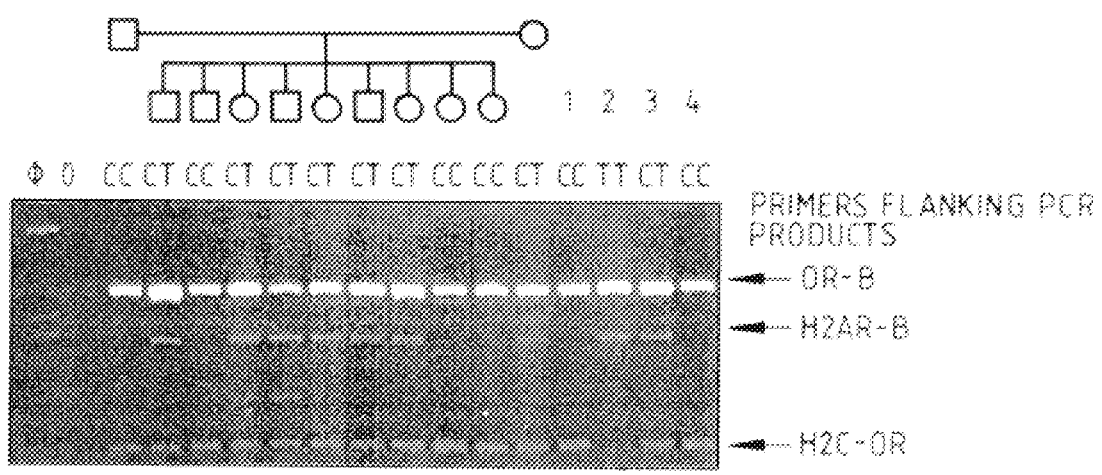

FIGS. 22A–22C shows PCR assays for the three polymorphic sites identified in the flanking region of MS32. A: Segregation analysis of the Hump1 polymorphism for CEPH family 1416, SSCP analysis top and PCR assay bottom (genotypes for each individual are shown, GGIGC/CC). PCR-SSCP analysis of the flanking DNA amplified with 32-OR and 32-B was performed using the method of Orita et al., 1989, incorporating $\alpha$-$^{32}$P-dCTP during PCR, followed by digestion with HinfI and electrophoresis through a 5% polyacrylamide, 10% glycerol gel in 1x TBE at 4° C. For the direct HumpI PCR assay 0.1 $\mu$l of 32-OR-32-B PCR product was reamplified using the nested primers 32-H1B and 32-NR for 28 cycles with an annealing temperature of 55° C. and an extension time of 2 minutes. 5 $\mu$l of this amplification was digested with Bsp1286I and resolved by gel electrophoresis through a 3% NuSieve GTG, 1 % Sigma TypeI agarose gel in 1x TBE and the products visualised by ethidium bromide staining. Zero DNA controls (O) and X174 HaeIII size markers (Φ) are also shown. B: Segregation analysis of the Hf polymorphism for CEPH family 1331. 348 bp of immediate flanking DNA was amplified using primer pair 32-OR plus 32-B for 30 cycles with an annealing temperature (A) of 69° C. and a 2 minute extension time (E). 2 $\mu$l of PCR products were digested with HinfI, resolved by electrophoresis as above. All individuals produce a constant 163 bp product. Individuals homozygous for the Hf- allele (−−) produce a produce of 199 bp. In individuals homozygous for the Hf$^+$ allele (++) the 199 bp band is further digested to give bands of 141 and 58 bp. Heterozygous individuals (Hf$^+$/Hf−) produce all four bands (+−). C: Segregation analysis of the Hump2 polymorphism for CEPH family 1421 and four unrelated individuals (1–4C; genotypes for each individual are shown, CC/CT/TT). Hump2 analysis was achieved using primers 32-OR, 32H2C, 32-H2AR and 32-B at final concentrations of 0.5, 0.5, 2 and 1 $\mu$M respectively in a single tube assay. PCR was performed with an annealing temperature (A) of 67° C., an extension time (E) of 2 minutes for 30 cycles and the products resolved by agarose gel electrophoresis as above.

FIG. 23 shows primate sequence comparisons for the MS32 flanking region. The sequence of the human clone between primer pair 32-OR and 32-B is given in full (Wong et al., 1987). The human-African Ape ancestral sequence was derived from the human, Chimp, Gorilla and Orang-utan sequences (Gray and Jeffreys, 1991), using Organg-utans as the outgroup. HC=Human Clone, AS=Ancestral Sequence and HV=Human Variant. Positions of variation only are indicated in bold. N's in the ancestral sequence represents sequence not known.

FIG. 24 shows 'knockout' MVR-PCR. For each of flanking polymorphisms (Hump1, Hf and Hump2) three unrelated individuals (1–3) were chosen who were heterozygous for the polymorphism. Each individual was analysed by MVR-PCR using either the universal flanking primer 32-O (O) to generate the diploid code from both alleles or the allele specific flanking primer (32-H1C, 32-D2 or 32-H2C) to generate coding from a single allele. MVR-PCR products extending to a-type repeats (T) were resolved by agarose gel electrophoresis and Southern blot hybridisation using $^{32}$P-labelled MS32 as probe. The 10th repeat unit on the MVR-PCR ladder is arrowed to show registration of single allele and diploid codes.

Figure 25:
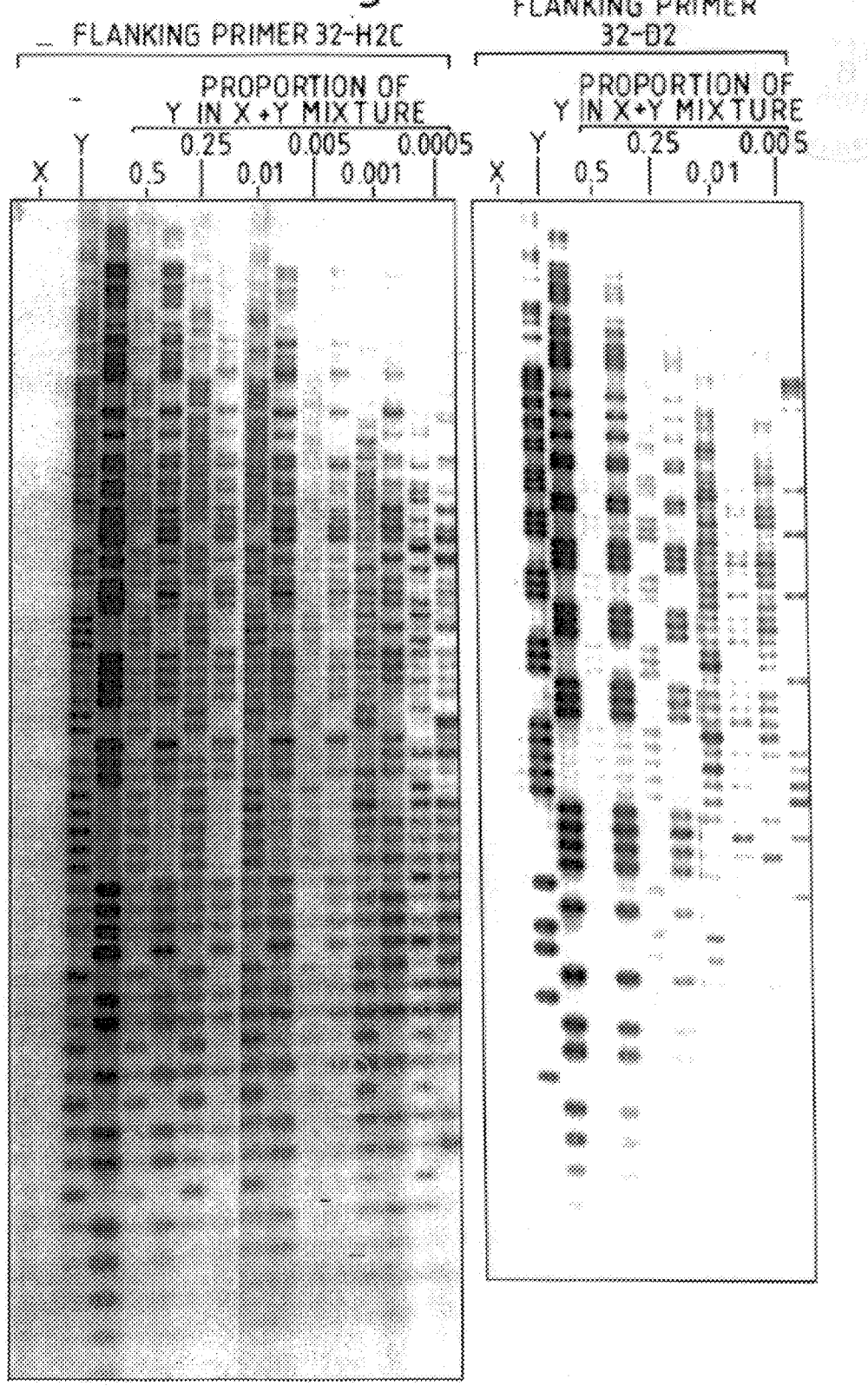

FIG. 25 shows the application of knockout MVR-PCR to mixed DNA samples. MVR-PCR of mixtures of two DNAs using allele specific flanking primers 32-D2 or 32-H2C in an otherwise standard MVR-PCR reactions. Individual X ('victim') was a Hf- homozygote (Hf-/Hf-) and a $H2^T$ homozygote ($H2^T/H2^T$) and individual Y ('assailant') was a Hf heterozygote (Hf+/Hf-) and a $H2^C$ homozygote ($H2^C/H2^C$). Mixtures of DNA from X and Y were prepared using a fixed amout of X (150 ng) and decreasing amounts of Y (150 ng down to 0.75 ng). The most dilute samples of Y (1/100+1/200) were given a further 2 cycles of PCR to increase the yield of product to detectable levels. The FIGS. 0.5, 0.25, 0.01, 0.005, 0.001, 0.0005 represent the proportion of Y in the X+Y mixture.

Figure 26:
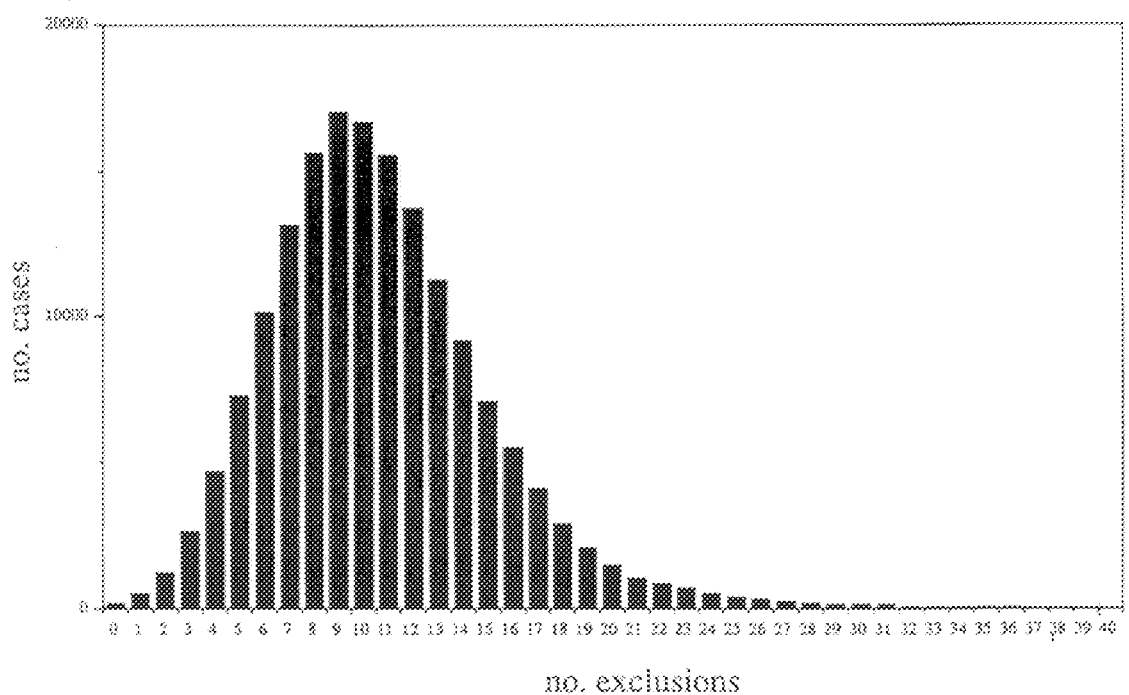

FIG. 26 shows the efficiency of single allele codes in excluding individuals based on comparison with their diploid codes. Single allele codes extending over at least 50 repeat units were established for 411 different MS32 alleles (349 Caucasian and 62 Japanese). Each allele was then compared with the diploid code of each of 408 unrelated individuals, giving 167,688 allele/individual comparisons in total. For each comparison, repeat unit positions which excluded the allele as having come from the individual were identified; for example, an allele with a t-type repeat unit at a given position could not have come from an individual homozygous for a-type repeats at that position. The frequency distribution of the total number of exclusions over the first 50 repeat units is given for all allele/individual comparisons. The Y axis represents the number of cases and the X axis represents the number of exclusions.

Figure 27:
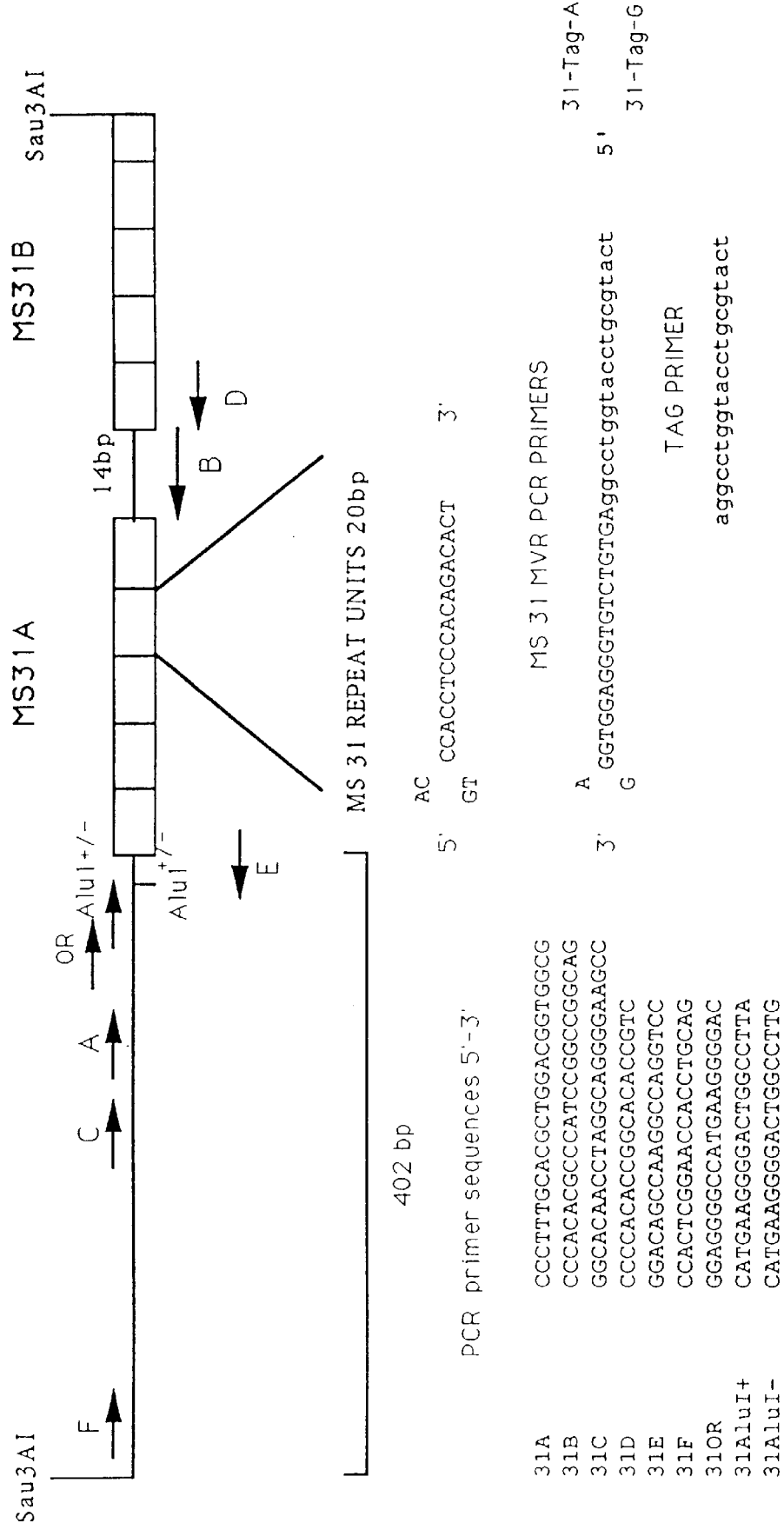

FIG. 27 shows the organisation of the MS3 1 locus and the localisation of PCR primer sites and the flanking AluI +/- site polymorphism. Primer sequences (5'-3') are as follows:

A=31A=CCCTTTGCACGCTGGACGGTGGCG SEQ ID NO: 27
B=31B=CCCACACGCCCATCCGGCCGGCAG SEQ ID NO: 28
C=31C=GGCACAACCTAGGCAGGGGAAGCC SEQ ID NO: 29
D=31D=CCCCACACCGGCACACCGTC SEQ ID NO: 17
E=31E=GGACAGCCAAGGCCAGGTCC SEQ ID NO: 18
F=31F=CCACTCGGAACCACCTGCAG SEQ ID NO: 19
310R=GGAGGGGCCATGAAGGGGAC SEQ ID NO: 20
31AluI+=CATGAAGGGGACTGGCCTTA SEQ ID NO: 21
31AluI-=CATGAAGGGGACTGGCCTTG SEQ ID NO: 22

31-Tag—A = A
               GGTGGAGGGTGTCTGTGAggcctggtacctgcgtact SEQ ID
31-Tag—G = G                            no: 35

Tag=aggcctggtacctgcgtact SEQ ID NO: 36

The relevant 20bp MS3 1 repeat units are ACCCACCTC-CCACAGACACT SEQ ID NO: 9 and GTCCACCTCCCA-CAGACACT SEQ ID NO: 10 respectively.

Figure 28:
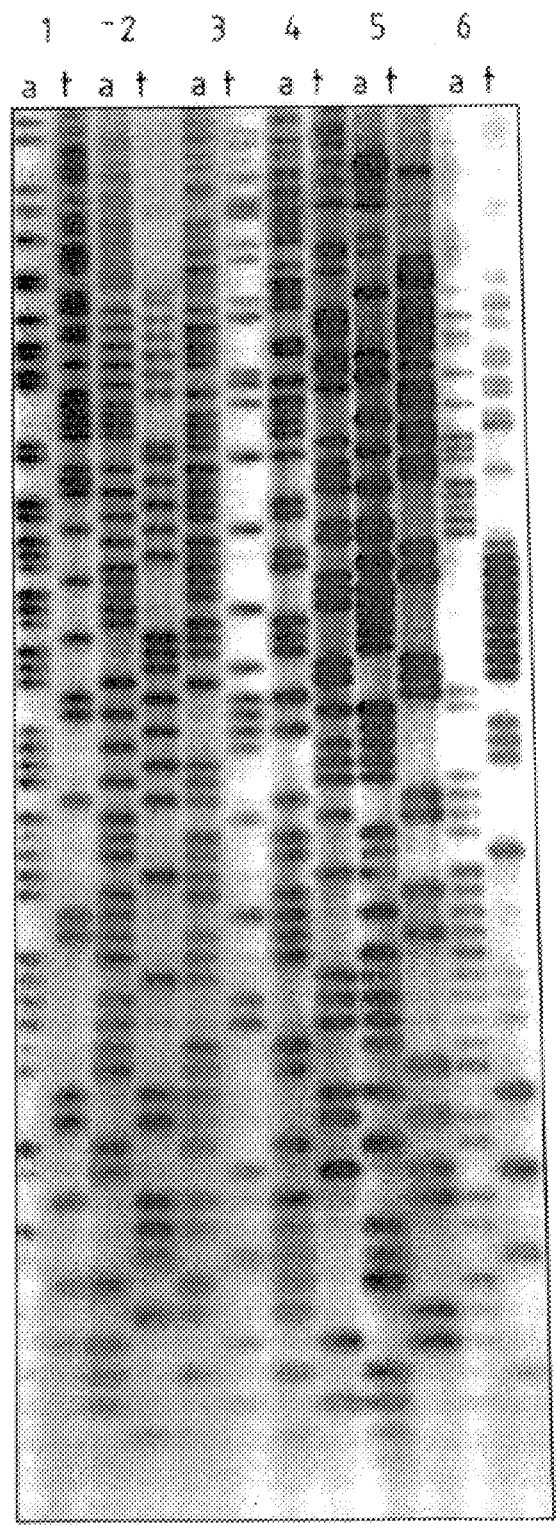

FIG. 28 shows MVR-PCR analysis of single MS31A alleles. For each allele, amplification was performed with 31-Tag-A to reveal the position of a-type repeats (a track) and 31-Tag-G to map t-type repeats (t track). The bracketed region in allele 6 shows examples of band intensity fluctuation.

Figure 29:
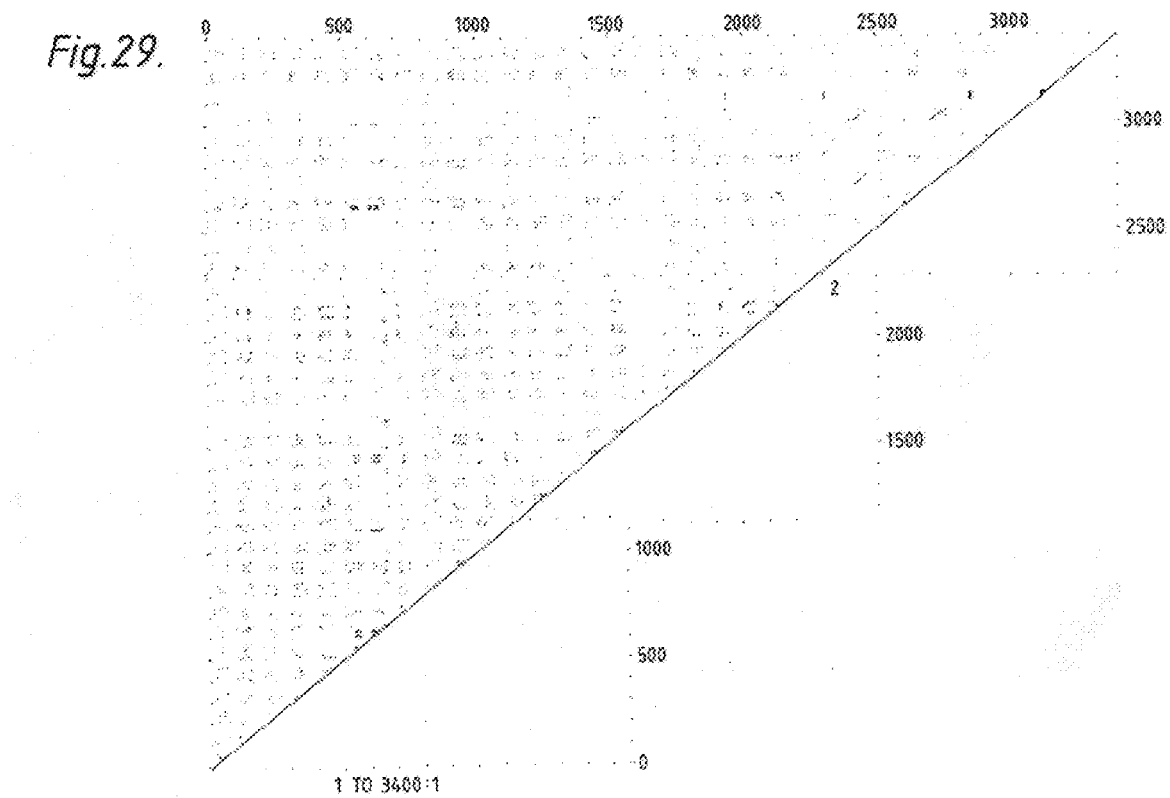

FIG. 29 shows the identification of related MS31A alleles by dot matrix analysis. The MVR codes of 34 different Caucasian alleles were assembled into a continuous "sequence" with each allele followed by padding to increase its length to 100 repeats (3400 "repeats" in total "sequence"). The dot matrix shows this complete sequence compared with itself to search for 8-repeat perfect matches. Related alleles generate short diagonals off the main diagonal.

FIG. 30 shows three MS31A alleles showing related segments (uppercase) in their MVR codes, a =a-type repeat; t =t-type; O=null or O-type repeat. Indicated are MVR code for (i) lower allele of CEPH individual 133413, (ii) lower allele of CEPH individual 1329912 and (iii) lower allele of CEPH individual 6602.

Figure 31:
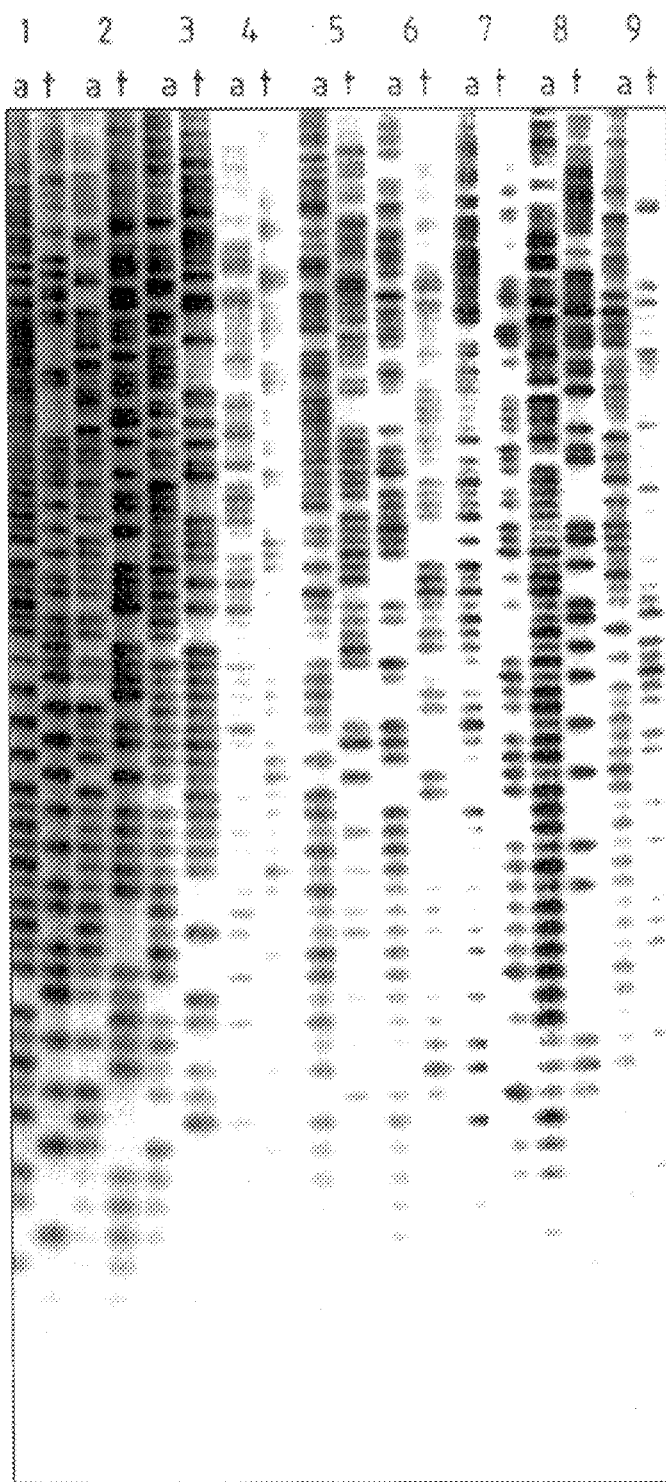

FIG. 31 shows digital coding of genomic DNA by duplex MVR-PCR. Each PCR reaction contained 100 ng genomic DNA from individuals (1–9) and 1 $\mu$M Tag, 1 $\mu$M flanking primers 31A and 320R, plus 40 nM 31-Tag-A, 10 nM 32-Tag-C (a-track) or 20 nM 31-Tag-G, 20 nM 32-Tag-T (t-track). After 21 cycles of MVR-PCR, PCR products were resolved by agarose gel electrophoresis and detected by Southern blot hybridisation with $^{32}$P labelled MS31.

Figure 32:
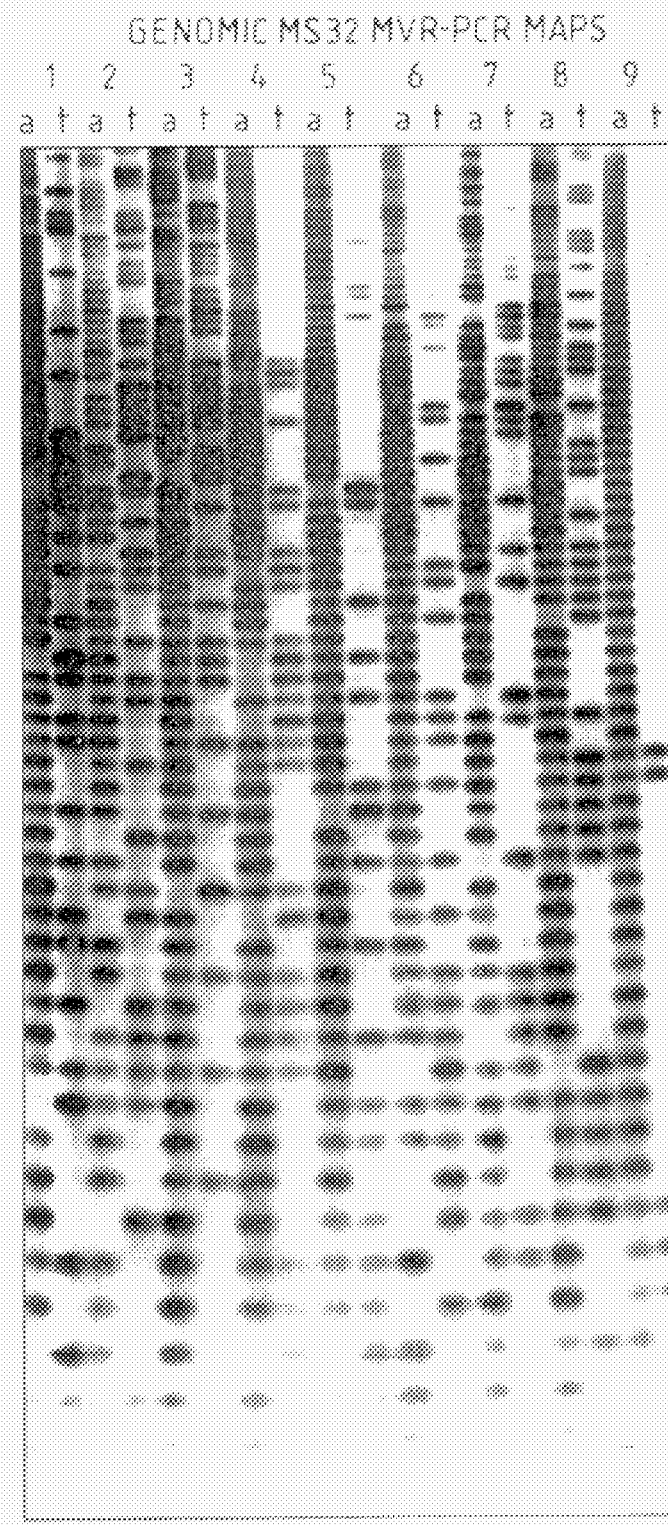

FIG. 32 shows the results of probe stripping the gel shown in FIG. 31 and re-probing with 32P labelled MS32.

Figure 33:
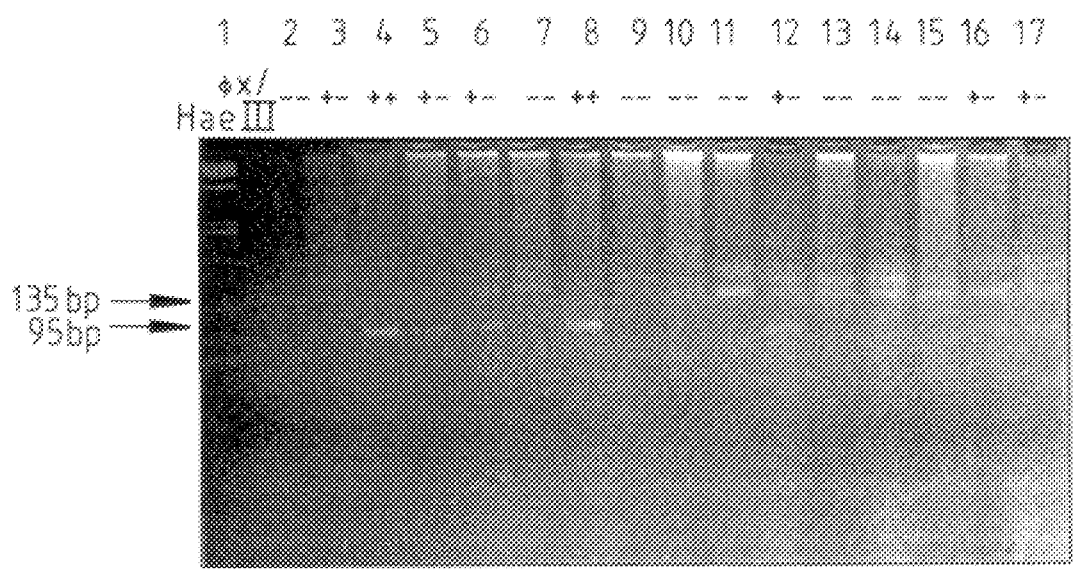

FIG. 33 shows a PCR assay of the AluI site polymorphism flanking MS31A. 100 ng samples of genomic DNA from 17 different individuals were amplified in 7 $\mu$l PCR reactions with 1 $\mu$M 31-Tag-A, 1 $\mu$M flanking primer 31A and 0.25 units of Taq polymerase (Amersham) for 35 cycles of 96° C. for 1.3 min., 70° for 1 min. per cycle, followed by a chase of 67° C. for 1 min., 70° C. for 10 min. The unpurified PCR products were then digested with 5 units AluI in the presence of 1 mM spermidine trichloride and the approprite buffer and electrophoresed through a 5% NuSieve (FMC) agarose gel in 40 mM Tris-acetate (pH 8.3), 0.2 mM EDTA. DNA was visualised by staining with ethidium bromide.

Figure 34:
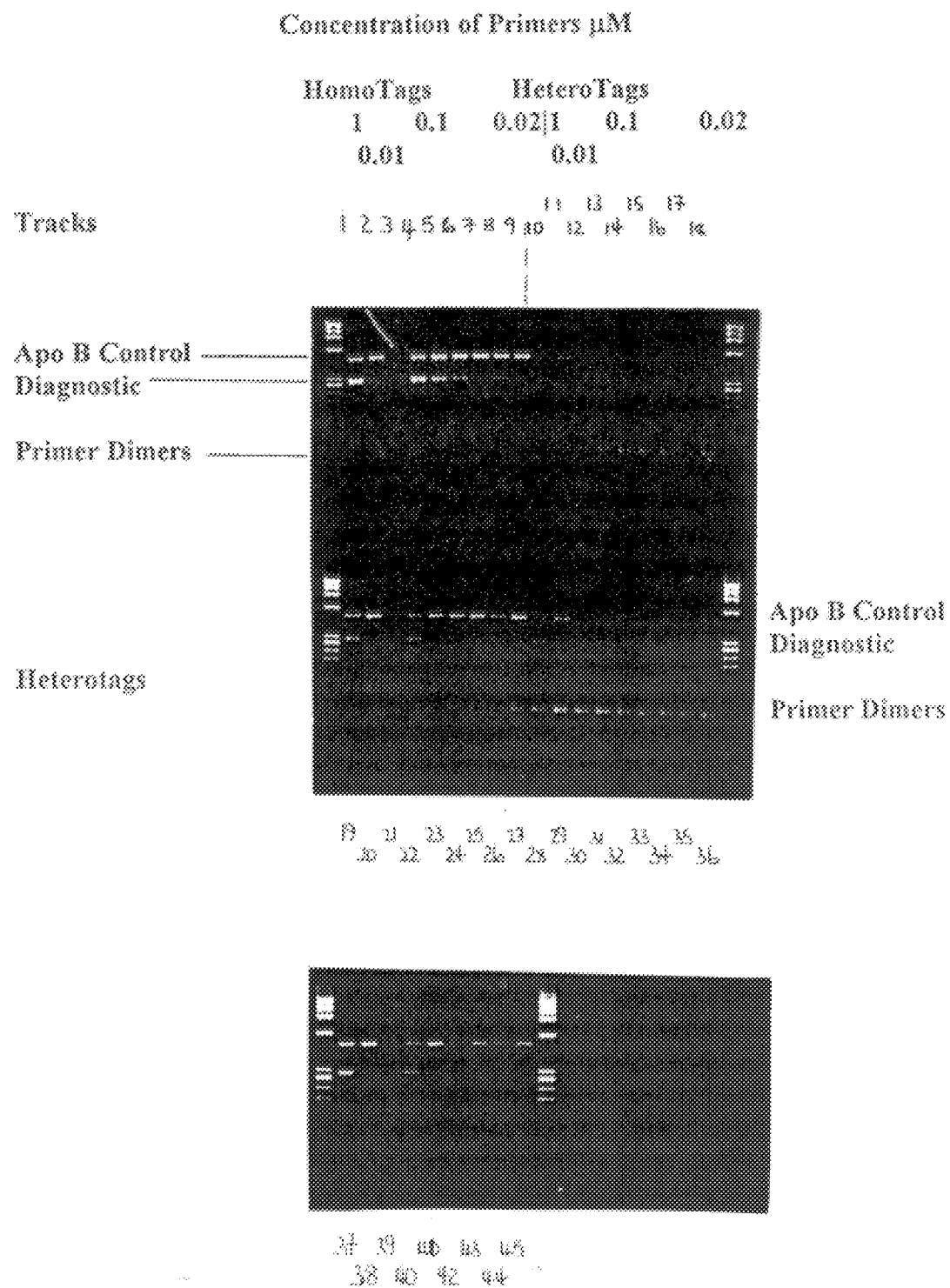

FIG. 34 demonstrates that a HomoTag format of a tags and tails reaction is favoured over a HeteroTag format.

Tracks 1–9 on the gel represent the HomoTag format—mixes 1A–1D. Although primer dimers are visible when 1 mM of tailed primers were used, these disappear with the lower primer concentrations. The sensitivity of the test is high, represented by the strong diagnostic band obtained when only 0.01 mM of specific tailed primers are present in the mix.

The remainder of the tracks represent the various HeteroTag formats—tracks 10–18 are, mixes 2A–2D, tracks 19–27 are mixes 3A–3D, tracks 28–36 are mixes 4A–4D and tracks 37–45 are mixes 5A–5D, as described in the methods.

In all cases the sensitivity of the test was poor with a high concentration of primer dimer.

Figure 35:
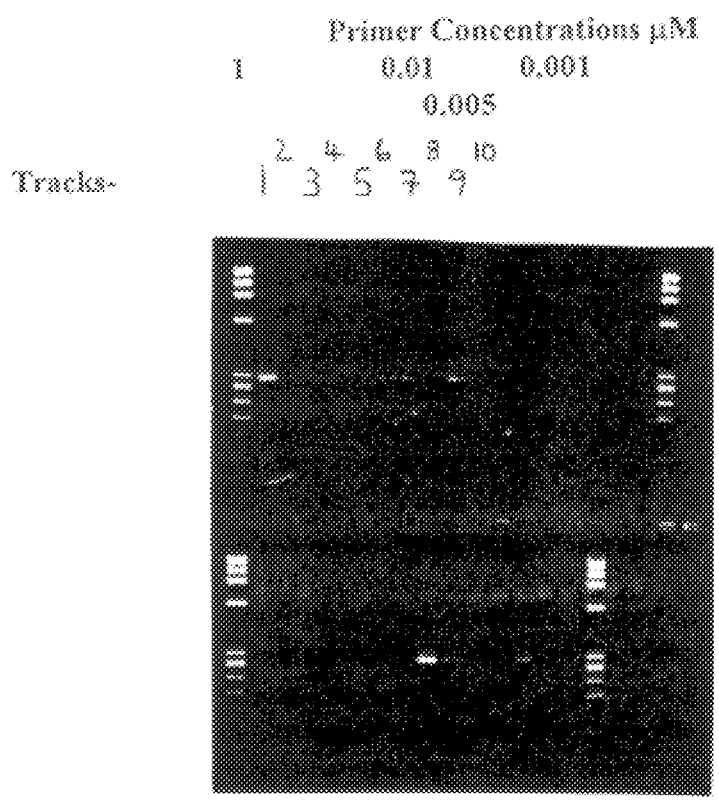

FIG. 35 demonstrates the efficiency of inhibition of primer-dimer amplification with a HomoTag format. The upper band represents the G542X mutation diagnosis, which is still apparent when the tailed primer concentration is dropped to 0.005 mM, seen in track 9. Primer dimers are non-evident in this format except with the first sample, when the tailed primers are at 1 mM as in track 1.

Figure 36:
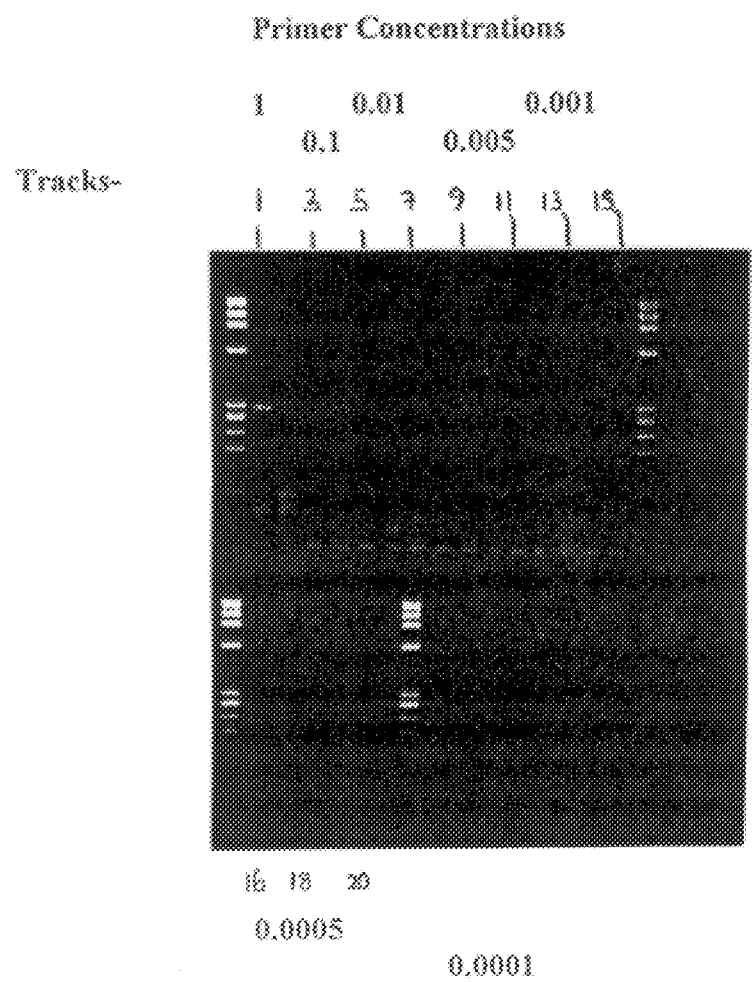

FIG. 36 demonstrates the efficiency of primer-dimer amplification in a HeteroTag format. The upper diagnostic band is no longer present after track 4, therefore at least 0.1 mM of tailed primers need be present to produce a positive result, although at this concentration yield is very poor. The reason for lack of sensitivity in this format is likely to be due to the large degree of primer-dimer amplification which occurs. This reaction is favoured over product amplification and is highly efficient. When tailed primers are added at only 0.1 nM, primer-dimers are still visible on the gel, seen in tracks 19–21.

Figure 37:
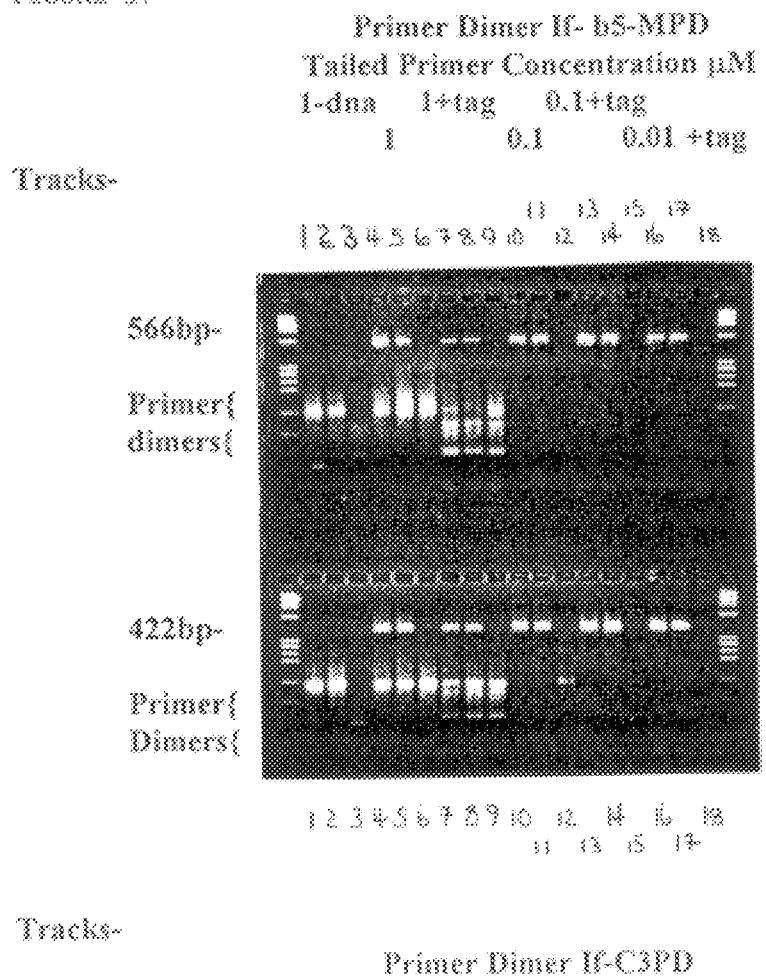

FIG. 37 demonstrates the inhibition of primer-dimer amplification in a HomoTag format, with low primer concentration, and the benefits of this in a PCR-based test Tracks 1 & 2, in both cases, show that the primers designed for the test are capable of forming a strong primer-dimer.

Tracks 4 & 5, show how the yield of 'diagnostic' product is compromised by presence of this primer dimer, and tracks 7 & 8, that when the specific tag primer is added to the mix the increase in primer-primer interactions compromises this yield even further Tracks 10 & 11 demonstrate that reducing the tailed primer concentration to 0.1 mM, reduces the primer-dimer formation and in tracks 13 & 14, when tag has been added to the reaction, inhibition of any subsequent primer-dimer amplification has been effectively blocked and sensitivity of the test is no longer compromised.

Tracks 16 & 17 show complete eradication of primer dimer and thus a good yield of 'diagnostic' product, despite primer concentration being only 0.01 mM.

FIG. 38 shows the large quantities of the 3 deliberate primer-dimers prepared for subsequent analyses using dilution series of HomoTagged and HeteroTagged primer-dimers.

Figure 39:
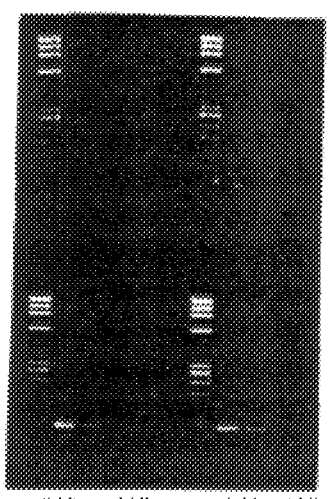

FIG. 39 shows successfully extracted and purified primer-dimers from FIG. 38. Each purified sample was diluted and compared against FX174 RF DNA/Hae III digest fragments to enable quantification for future experiments.

Figure 40:
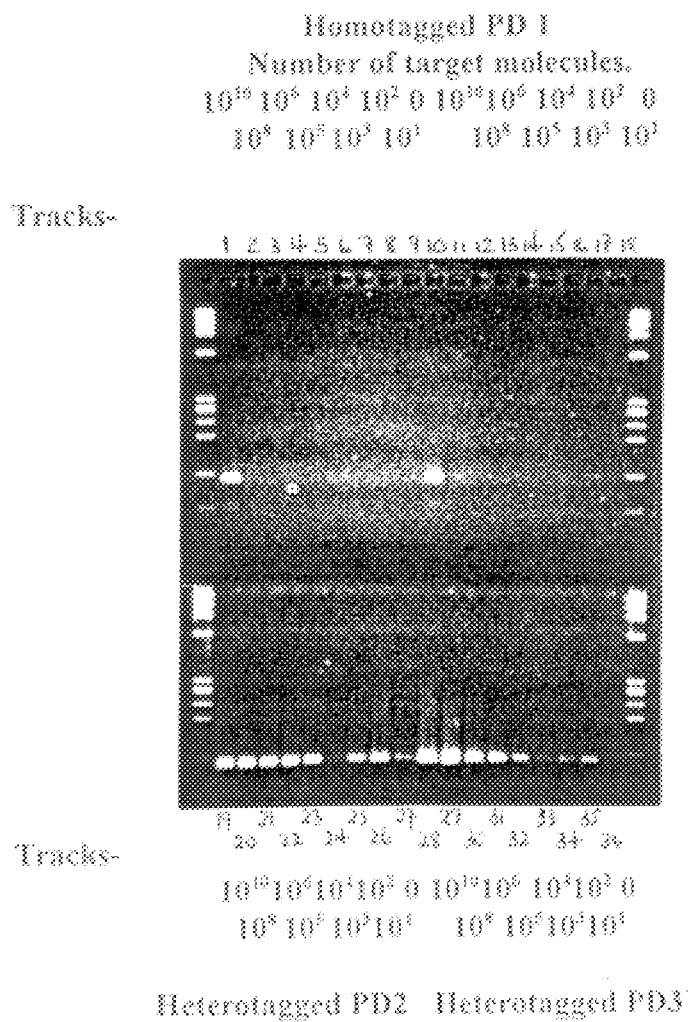

FIG. 40 demonstrates the effective inhibition of amplification of a HomoTagged primer-dimer compared to a HeteroTagged sample. HeteroTagged primer-dimers were easily amplified to produce a visible product when only $10^1$ target molecules were present in the mix, seen in tracks 26 and 35. HomoTags however, only produced a visible band in tracks 1 and 10, when $10^{10}$ target molecules were present.

Figure 41:
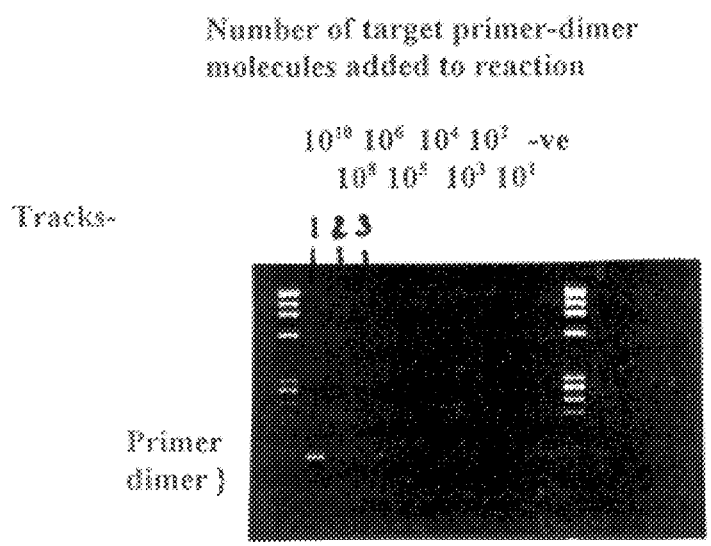

FIG. 41 demonstrates that the inhibition of primer-dimer amplification with HomoTags is due to intra-molecular secondary structure. With the higher annealing temperature of 74° C., a visible primer-dimer band is seen in track 3, when $10^6$ target molecules are present in the mix. With an annealing temperature of 60° C. this band only became apparent when $10^{10}$ of the same target molecules were added (FIG. 40).

EXAMPLE 1

MVR-PCR on separated MS32 alleles

To determine the feasibility of MVR-PCR, genomic DNA from individuals known to contain large MS32 alleles was cleaved with Sau3AI and alleles separated by preparative gel eletrophoresis. Each separated allele was amplified with 1 μM 32D plus 1 μM TAG primers in the presence of increasing concentrations of 32-TAG-A or 32-TAG-T. PCR products were resolved by agarose gel electrophoresis and detected by Southern blot hybridization with $^{32}$p-labelled MS32 minisatellite probe. The yield of PCR products increased with increasing concentration of MVR-specific primers, but at high concentrations, the products progressively shortened due to internal priming (data not shown). At optimal primer concentrations (10 nM 32-TAG-A, 20 nM 32-TAG-T), complementary ladders of PCR products extending >3 kb into each allele were generated, from which allele binary codes could be readily deduced (FIG. 2).

Minimal mispriming of MVR-specific primers occurred off the wrong repeat units at annealing temperatures above 64° (data not shown). In most cases, the two MVR-specific primers generated a continuous complementary series of products. Occasionally, however, a "rung" on the MVR coding ladder failed to be amplified by either MVR-specific primer (FIG. 2), indicating the presence of "null" repeats containing an additional sequence variant 3' to the HaeIII site which blocks priming by either primer. 1.6% of repeats units scored from 32 separated Caucasian alleles were null or O-type repeats.

EXAMPLE 2

Authenticity of allele MVR codes generated by MVR-PCR

To determine whether these allele codes agreed with codes established by partial digestion with HaeIII, PCR product 2.5–3.0 kb long from MVR-PCR were size-selected by agarose gel electrophoresis, re-amplified using primer 32D plus TAG until >10 ng product was generated, and mapped as described previously (Jeffreys et al., 1990), by end-labelling at the 32D primer site and partial digestion with HaeIII. 32 different MS32 alleles so mapped gave fully concordant results using both approaches. Representative examples of MVR codes are given in FIG. 3A, and a summary of MVR composition of alleles in FIG. 3B. The rare null or O-type repeats correspond to both HaeIII resistant repeats. Other than O-type repeats, all a- and t-type repeats were fully concordant, with only one exception, namely one allele containing a single repeat amplified by 32-TAG-A but not cleaved by HaeIII (FIG. 3A). This repeat presumably contains a rare variant at the first base of the HaeIII site which destroys the restriction site but does not affect priming by 32-TAG-A (FIG. 3C).

EXAMPLE 3

MVR-PCR on total genomic DNA

MVR-PCR on genomic DNA should produce a profile of both alleles superimposed, to generate for two-variant alleles a ternary code (FIG. 1A), where each rung in the ladder can be coded as 1 (both alleles a-type at that position, aa), 2 (both t-type, tt) or 3 (heterozygous, at). The presence of O-type repeats creates three additional coding states, namely 4(aO), 5(tO) and 6(OO). The last will appear as a gap on the ladder and the first two as relatively faint bands specifically in the A- or T-track. Coding states 4–6 will also be generated if one allele is short; beyond the end of the short allele, the code will be derived from only one allele, and if both alleles are short, then no PCR products will appear beyond t he longer allele, generating a 66666 . . . . code.

To investigate the feasibility of MVR-PCR on total genomic DNA, 0.1 μg samples of human DNA were amplified and products detected by Southern blot hybridization with MS32 minisatellite probe (FIG. 4). In each case, clear and unambiguous diploid codes could be read at least 50 repeat units into the minisatellite. The two tracks generating the code contain considerable informational redundancy; thus in almost all cases, an intense band in the A-track was matched by no band in the T-track (code 1, aa), a faint A band by a faint T band (code 3, at) and no A band by an in tense T band (code 2, tt). This dosage phenomenon not only provides a detailed check on the authenticity of the code generated, but also makes it possible to identify with good reliability any rung positions which are heterozygous for a null or O-type repeat (code 4, aO; code 5, to); examples of such positions are shown in FIG. 4.

EXAMPLE 4

Individual variation in diploid codes

The MVR-PCR profiles shown in FIG. 4 clearly shown extreme variation between individuals. To investigate further the degree of variability of these codes, a panel of 334 unrelated individuals was typed by MVR-PCR. All diploid codes were read from the second repeat unit into the minisatellite, since the first repeat is faint and cannot be reliably scored. The start position for reading the code was confirmed by running a standard individual of known code on all gels; the standard individual also provided a check that the correct codes were being generated on a given gel. If there was any doubt whatsoever about the coding state at any given repeat in an individual, the rung was coded as "?". Only 0.3% of code positions (59 rungs in 20,702 scored) were entered as "?" and were ignored in subsequent database searches.

Every pairwise comparison of the 334 diploid MVR codes over the first 50 repeat units scored revealed that no two individuals typed shared the same code (FIG. 5). The individual specificity remained when band intensity information was removed by converting all code 4(aO) and code 5(tO) positions to codes 1(aa) and 2(tt) respectively, to generate quaternary codes (1,2,3,6) corresponding to a band present only in the A-track, only in the T-track, in both tracks and in neither track, respectively. There were on average 30 mismatches per pair of individuals over the first 50 repeat units, with a smooth distribution of mismatch frequencies over all 55,611 pairwise comparisons in the population database (FIG. 5A,B). All individuals could in fact be distinguished using information from just the first 17 repeat unit positions. The two most similar individuals had MVR codes dominated by code 1(aa), indicating that all four alleles in these individuals were composed largely of a-type repeats; such homogeneous alleles have been noted previously (Jeffreys et al., 1990). The most dissimilar pairs of individuals arose where one individual contained a short allele, creating a diploid code dominated by the rare codes 4,5 and 6 (FIG. 5C). Individuals with short alleles create the shoulder of high numbers of repeat unit differences on the frequency distribution shown in FIG. 5A, and as predicted, this shoulder is eliminated on removal of band intensity assumptions. 7.8% of individuals contained short (<50 repeats) alleles with allele lengths ranging from 19 to 44 repeat units. Short alleles do not occur with equal frequency in all populations; thus 5.6% of Caucasian individuals contain short alleles, compared with 23% of Japanese (p<0.001).

EXAMPLE 5

Heterozygosity levels at MS32 determined from MVR codes

Diploid codes provide a more objective method for identifying homozygotes than allele length measurements by conventional Southern blot hybridization analysis of genomic DNA. Presumptive homozygotes will show diploid MVR codes restricted to code 1(aa), 2(tt) and 6(OO), with no heterozygous repeat positions. Three individuals (one French, two Japanese) one of 334 surveyed showed homozygosity by this criterion, suggesting a mean heterozygosity level of 99.1%. It is possible that such apparent homozygotes are in fact heterozygous for a second allele which contains a 32D primer mismatch in the flanking DNA (FIG. 1C), preventing PCR amplification. However, all individuals scored as homozygous by MVR-PCR showed as predicted a single band on Southern blot hybidization of genomic DNA (data not shown). Conversely, the majority (8/10) of apparently single band individuals detected by hybridization with MS32 were in fact heterozygous for similar or identical length alleles as shown by diploid coding, again establishing that the level of variability at MS32 is substantially greater than can be resolved by conventional allele length analysis.

EXAMPLE 6

Variation in repeat unit composition alone diploid MVR codes

The variation in allele MVR composition along the MVR code was extracted from the database of 334 individuals (668 alleles) (FIG. 6A). The relative frequency of a- and t-type repeat units is fairly uniform at all positions along the code, whereas the frequency of O-type repeats within alleles tend to increase with distance into the alleles; this may reflect reduced levels of homogenization at the relatively invariant distal ends of MS32 alleles allowing additional repeat variants to arise by mutation within repeat units and to survive elimination by processes such as crossover fixation. The probability that two individuals would match at a given MVR code position is also fairly constant along the code (FIG. 6B) and is correctly predicted from the relative frequencies of a-, t- and O-type repeats at each position. This in turn implies that each repeat position, treated as a triallelic locus (a, t, O), is a Hardy-Weinberg equilibrium in the population. $\chi^2$ tests show this to be the case (FIG. 6C). However, Hardy-Weinberg equilibrium at each position does not imply linkage equilibrium between different positions; indeed, there is clear evidence for major disequilibrium between these essentially completely linked repeat unit positions, as shown for example by the existance of alleles largely homogenized for a-type repeats (FIG. 5C), see Jeffreys et al., 1990), non-random dispersal of O-type repeats over alleles and individuals (FIG. 3A), and the existence of distinct but very closely related alleles (see below).

EXAMPLE 7

Extraction of allele MVR maps from pedigrees

The variability of diploid MVR codes is governed by the number and frequencies of different MS32 alleles in human populations. MS32 alleles can be mapped using electrophoretically-separated alleles (FIG. 2). However, this approach is cumbersome, and a far simpler approach is to deduce allele haplotypes from pedigree data, as shown in FIG. 7. Using the diploid MVR codes of a mother, father and a single child, it is possible to deduce the MVR haplotypes of all four parental alleles, except at repeat positions where all individuals are heterozygous for the same variant repeats (e.g. all individuals code 3, at). The minimum data required to determine completely all four parental haplotypes are the diploid codes of the mother, father and two children who share only one parental allele in common. In more extensive sibships, for example those of the CEPH families, up to four classes of children differing in their diploid codes can be identified corresponding to the four possible combinations of parental alleles. Computer programmes have been developed which can extract the unambiguous parental haplotypic maps from such sibships, as well as identifying the parental alleles transmitted to each child (FIG. 7 legend). Such large sibships also contain considerable informational redundancy useful for checking the authenticity of the deduced haplotypes. In addition, 11 of the haplotypes of relatively short alleles deduced from large pedigrees have also been verified by HaeIII cleavage of PCR amplified alleles (FIG. 7).

EXAMPLE 8

Allelic variability at minisatellite MS32

Family analysis, together with analysis of eletrophoretically-separated alleles, has allowed us to generate mapping data on 254 Caucasian alleles (FIG. 8). Haplotype comparisons show that this collection of alleles contains 248 different alleles, 243 of which have been detected only once in the alleles surveyed. Under a simple model in which all alleles are equally rare, Poisson distribution analysis indicates that approximately 6300 different MS32 alleles must exist in Caucasians to give the sampling frequency distribution shows in FIG. 8A. The only allele with a possibly significant frequency (FIG. 8A,B) still has a very low frequency (3/254=0.012). If this allele is removed, the Poisson estimate for the total number of alleles increases. The allele number estimate is also likely to be conservative since one of the four pairs of alleles sampled twice is present in the only Caucasian homozygote so far detected, and another is shared by the parents of an Amish family; such repeat isolates of alleles may therefore reflect consanguinity/inbreeding rather than alleles with a significant population frequency shared by unrelated individuals.

The allele database also contains several examples of pairs of alleles which show relatively few differences and where the MVR codes are clearly related (FIG. 8C). Interestingly, these pairs of alleles show differences preferentially clustered over the beginning of the alleles; this reflects the gradient of variability previously detected along MS32 alleles mapped in their entirety by HaeIII cleavage (Jeffreys et al., 1990). Note that the mutational changes(s) which have altered the map of these related alleles can not have resulted in a net change in repeat copy number, which would throw the allelic MVR codes out of register beyond the point of repeat copy number change, creating multiple differences.

EXAMPLE 9

Mutation rates and processes at MS32

The levels of allelic variability at MS32 so far estimated are extraordinary, and go far beyond the number of alleles which can be discriminated by length (repeat unit copy number). Such ultravariability must be maintained by a high de novo mutation rate altering the MVR map of MS32 alleles. Allele length changes at MS32 have already been detected both by pedigree analyis (Armour et al., 1989) and by single molecule PCR analysis of mutant alleles arising by large deletions (Jeffreys et al., 1990).

To quantify MS32 haplotype mutation rates, diploid MVR codes were analysed in 286 offspring from the CEPH collection of large families (FIG. 9). 7 offspring were found with MVR codes showing multiple parental exclusions, indicating the presence of a mutant allele. In each case, code positions specifically excluding only one parent were detected (FIG. 9.1), defining the parental origin of the mutant allele. Non-mutant children in the same family were used to deduce the haplotypes of the non-mutant parental alleles, whence the non-mutant allele inherited by the mutant child could be identified. Subtraction of this non-mutant allele from the diploid code of the mutant child yielded the MVR haplotype of the mutant allele. Comparison of the mutant map with the maps of the two possible progenitor alleles allowed the nature of the mutation event to be mapped onto the MVR haplotype of the parental progenitor allele(s).

The overall mutation rate in MS32 MVR maps is approximately 0.012 per gamete, with paternal and maternal mutations arising with similar frequency. Curiously, all 7 mutations events so far detected were associated with a gain in repeat copy number, in most cases of a very small number of repeat units (1–3 repeats). All germline length change events previously found in MS32 alleles (Armour et al., 1989) were also detected in this survey, together with three additional events each resulting in the gain of a single repeat unit (29 bp DNA); not surprisingly these events were not detectable by Southern blot analysis of genomic DNA but nevertheless have a profound effect on the diploid MVR code.

Despite the fact that MS32 alleles are on average 200 repeat units long, the locations of the mutation events are extremely clustered, in most cases within the first 10 repeat units of the MS32 alleles over the region known to show maximum allelic variability. This provides further evidence for the presence of a mutational hotspot at the extreme end of MS32 alleles, responsible for generating the gradient of variability seen along this locus (Jeffreys et al., 1990).

Some information about mutation mechanisms could be deduced from comparison of mutant and progenitor alleles. For mutant d (FIG. 9.2,3), the site of the single repeat unit addition in the mutant allele is preceded and followed by MVR code derived from the same maternal allele. Such an event is probably intra-allelic, and could have arisen for example by unequal sister chromatid exchange or by replication slippage. In contrast, mutant e (FIG. 9.1-3) provides clear evidence for inter-allelic unequal exchange between the two paternal alleles, the mutant allele commencing with one paternal haplotype, then switching after two a-type repeats of unknown origin to the beginning of the other paternal allele. The origin of the two a-type repeats is unclear, but may represent some form of slippage event at a recombination junction. One other mutant (f) also appeared to have arisen by inter-allelic unequal exchange, but the presumptive exchange point lies too close to the beginning of the allele to be certain that the mutant allele does contain a recombinant haplotype. Similarly mutants a, b and g appear to arisen by an intra-allelic event, but the-existence of a recombinant mutant allele cannot be ruled out.

A recombination hot-spot near the end of MS32 alleles?: Previous studies of DNA markers flanking minisatellite loci have shown that minisatellite allele length change is not exclusively driven by inter-allelic recombination, though the possibility of some inter-allelic unequal exchange could not be excluded (Wolff et al., 1988, 1989). Similarly, single molecule PCR analysis showed that large (39–136 repeat unit) and rare deletions in MS32 alleles were an exclusively intra-allelic phenomenon, and that inter-allelic unequal exchange could be responsible for, at most, only 6% of these large deletion events (Jeffreys et al., 1990). Similarly, the existence of MS32 alleles largely homogenised for a-type repeats suggests that inter-allelic exchange, which would distrupt homogeneous arrays by introducing t-type repeats, must be relatively scarce.

The present data provide the first evidence that inter-allelic recombination plays a significant role in minisatellite instability, at least at MS32. One, and probably two, of the mutant alleles bear the hallmarks of unequal crossing over, although it is as yet unknown whether these represent authentic recombination events since currently available DNA markers flanking MS32 are too remote to test whether these mutations have been accompanied by exchange of distal flanking markers. If these two mutation events have arisen by a conventional (if unequal) inter-allelic recombination process, this implies a recombination frequency of 2/572=0.3 cM over the first 400 bp of the minisatellite, compared with a mean frequency of 1 cM per $10^6$ bp in the human genome and therefore representing a 700-fold enhancement of recombination. If correct, this would represent a dramatic example of a human recombination hotspot, and revitalizes earlier speculation that minisatellites may be actively involved in chromosomal processes such as homologue recognition, synapsis and meiotic recombination (Jeffreys et al., 1985a; Chandley and Mitchell, 1988; Royle et al., 1988). However, the simple recombination hotspot model would predict that additional "mutant" MS32 alleles should arise by equal recombination to produce recombinant haplotypes in which the repeat copy number is identical to one of the parental alleles. Screening of the CEPH families with multiple offspring should identify such recombinant children as offspring showing no parental exclusions but showing one (recombinant) haplotype incompatible with haplotypes derived from other children. Such recombinant alleles have not yet been detected. However, the clustering of exchange events at the extreme beginning of MS32 alleles may well make many such events undetectable.

We have previously suggested that MS32 alleles do not engage in inter-allelic exchanges and therefore evolve largely, if not exclusively, along haploid chromosomal lineages (Jeffreys et al., 1990). The present data suggest a more complex picture, with most mutational events involving the gain or loss of small numbers of repeat units towards the extreme beginning of alleles, and with a significant involvement of inter-allelic exchange in the mutation process. In contrast, regions of the tandem repeat array distal to the recombination hotspot show much lower allelic variability and appear to evolve by relatively low frequency intra-allelic processes such as unequal sister chromatid exchange and replication slippage This explains how alleles largely homogenized for a-type repeats can accumulate in the population, and it is significant that such homogeneous arrays are in fact usually preceded by a normal segment containing interspersed a- and t-type repeats (Jeffreys et al., 1990; data not shown), as expected if inter-allelic exchanges are largely confined to the beginning of the tandem arrays.

EXAMPLE 10

The sensitivity of MVR-PCR

Diploid MVR codes have a great power of individual discrimiation. To determine whether MVR-PCR can be applied to trace levels of DNA, decreasing amounts of human genomic DNA were amplified and typed. Normal profiles were obtained down to 10 ng genomic DNA (not shown). At 0.1–1 -ng DNA (17–170 diploid genomes), intensity fluctuations arose within the MVR profile, presumably due to stochastic loss of PCR products from the small number of input minisatellite molecules (FIG. 10). However, these fluctuations occurred apparently at random, and reliable consensus diploid codes could be derived by comparison of three replicate MVR profiles obtained from 0.1 ng samples of genomic DNA. Thus MVR-PCR can be extended reliably to sub-nanogram amounts of human DNA.

EXAMPLE 11

MVR-PCR on degraded DNA

MVR-PCR does not require intact minisatellite alleles but instead recovers information from any DNA fragments which are long enough to include the flanking 32D priming site located 192–212 bp before the minisatellite plus at least some 29 bp repeat units (FIG. 1C). To determine whether MVR-PCR can therefore be applied to degraded DNA, human genomic DNA was progressively sheared by soni-cation before amplication by MVR-PCR. Even highly sheared DNA (mean fragment size 400 bp, >95% of DNA <1000 bp long) generated authentic diploid MVR code information, although the code faded out after approximately 25 repeat units (data not shown). Nevertheless, the truncated codes obtainable from degraded DNA are still compatible with database searches, although with increasing loss of discrimination power as the code is progressively shortened. For highly degraded DNA, additional information an be recovered by substituting the flanking primer 32D for 320 (sequence GAGTAGTTTGGTGGGAAG-QGTGGT), which primes immediately adjacent to the start of the tandem-repeat array (FIG. 1C) (data not shown).

EXAMPLE 12

MVR-PCR on mixed DNA samples

Forensic samples sometimes contain DNA from two or more individuals. In particular, semen-bearing vaginal swabs from rape victims can yield DNA both from the known victim and from the assailant. To determine whether MVR-PCR can be applied to such mixed samples, genomic DNA from one individual was mixed with decreasing amounts of DNA from a second individual and typed (FIG. 11). Clear indication of admixture could be obtained down to 10% mixtures of DNA. Comparison of the code from the pure DNA sample ("victim") with the mixed DNA sample enabled an incomplete and ambiguous diploid code of the "assailant" to be derived (FIG. 11) which nevertheless can still be used successfully to interrogate a diploid code database to find a matching individual and to determine the frequency of matching individuals in the database. Thus MVR-PCR can be applied to mixtures of DNA from two individuals (eg. victim plus rapist DNA recovered from semen-bearing vaginal swabs), particularly if pure DNA from one of the individuals (eg. victim) is available.

The incomplete assailant codes deducible from mixed DNA samples will have less power of discrimination than normal diploid MVR codes. To determine the efficiency of idenfication using information from mixed DNA samples, $2\times10^6$ combinations of "victim", "rapist" and "false suspect" were created from the population database of MVR codes and checked for suspect exclusions (FIG. 12). The mean number of exclusions over the first 50 repeat units fell from 30 for normal MVR codes (FIG. 3) to 14 for comparisons of the ambiguous code deducible from mixed DNA samples with the normal MVR code of a suspect. The mean power of exclusion nevertheless remains very high (99.9993%).

EXAMPLE 13

The efficiency of diploid MVR codes in paternity testing

MVR-PCR can be used in parentage testing since the diploid codes of non-parents will frequently show exclusionary mismatches with the child. Such mismatches can either be directional, defining which parent is excluded, or ambiguous, indicating an inconsistency within an alleged mother-father-child trio but not defining which parent is excluded (see for example FIG. 9.1). To determine the effectiveness of MVR-PCR in excluding non-fathers, the MVR codes of 115 Caucasian mother-child duos were determined, and each duo was then compared with each of 249 unrelated Caucasian individual ("non-fathers") (FIG. 13A). On average, 9.9 exclusions were obtained per comparison of the first 50 repeats of the MVR codes, of which 4.7 were paternal-specific exclusions and the remainder directionally ambiguous. 98.9% of non-fathers showed at least one paternal-specific exclusion, and 99.8% showed at least one exclusion in total (paternal-specific plus ambiguous). Null or O-type repeats are relatively rare and when present in a child but not mother provide relatively powerful markers for excluding non-fathers. However, identification of heterozygous null positions (code 4, aO; 5, tO) requires correct interpretation of band intensities in the child. To determine the contribution of null repeats to the efficiency of paternity testing, the simulated non-paternity cases were re-evaluated after elimination of all code 4and 5 positions in each child (FIG. 13B). As expected, the mean numbers of exclusions fell significantly, causing a drop in the proportion of non-fathers showing exclusions from 99.8% to 99.5% (99.8% to 95.9% for paternal-specific exclusions). The above estimates for the efficiency of non-paternal exclusion are a mean over all mother-child duos. Variation between duos in these levels of exclusion was therefore investigated (FIG. 13C). The proportion of the 249 "non-fathers" excluded, either by paternal-specific exclusions or by total exclusions, varied substantially from duo to duo, according to the precise nature of the MVR codes of the mother and offspring. In the worst case, only 80% of non-fathers could be excluded. Nevertheless, the power of non-paternal exclusion of a single locus is impressive, and is significantly greater than can be achieved by convention Southern blot analysis of genomic DNA (Odelberg et al., 1989). This power is however offset of some extent by the relatively high de novo mutation rate of 1.2% per gamete, resulting in approximately 1.2% of offspring showing mutation of the paternal allele. The false exclusion rate of fathers is therefore approximately 1.2%, and the false inclusion rate of non-fathers is on average approximately 0.2–4.1%, depending on the nature of the exclusions employed in paternity testing.

EXAMPLE 14

MS32—Allelic variability

339 Caucasian alleles have been mapped by family analysis and from separate alleles. Haplotype comparisons revealed 326 different alleles, 316 detected only once in the alleles surveyed, together with 9 alleles sampled twice and one allele detected three times. The maximum frequency of any allele at this locus is therefore very low (3/339=0.009). Under a simple model in which all alleles are equally rare, Poisson disribution analysis indicates that ~3500 different MS32 alleles must exist in Caucasians to give this sampling frequency distribution. Given the high mutation rate of MS32 (see below), the true level of allelic diversity in humans is likely to be gigantic, with >$10^8$ different and distinguishable alleles in contemporary human populations different MS32 alleles can have related MVR haplotypes. All 326 different alleles were therefore compared to identify groups of alleles which showed significant similarities in repeat maps and to eliminate groups of alleles dominated by a-type repeats which showed high levels of matching without clear indication of significant relatedness (FIG. 14A). This heuristic alignment approach showed that 47% of alleles could be classified into 32 different groups each containing 2–22 significantly related alleles; each of the remaining 174 alleles showed no detectable matches with any other alleles. Example of groups of related alleles are shown in FIG. 14B. Most significantly, the majority of inter-allelic differences in repeat copy number and interspersion pattern of a- and t-type repeat units are resticted to the extreme beginning of the tandem array, over the region previously identified as showing greatest allelic variability. Less frequent differences further into alleles also occur, resulting mainly from minor changes in repeat unit copy number, and apparently from switching of a- and t-type repeats without changes in the number of repeat units.

EXAMPLE 15

Detection of cystic fibrosis (CF) mutations using tailed ARMS primers

In order to develop a useful ARMS test for somatic cancer mutations (e.g. the C>T mutations of codon 1338 of the APC gene) it is necessary to be able to distinguish between PCR failure and the absence of the mutation. The inclusion of additional control PCR reactions for the purpose of demonstrating PCR activity in negative ARMS tests causes a reduction in test sensitivity. However, as sensitivity is an absolute requirement of such tests, a method for the inclusion of a positive control PCR reaction without comprising sensitivity is required. The following two-step method employs the 5' TAG sequences technique for this purpose:

Step 1—A multiplex PCR reaction containing ARMS primers and control PCR reaction primers. All four primers carry the TAG sequence as a 5' tail. The control PCR amplimers are included at a low concentration relative to the ARMS primers (e.g. 10 nM cf 1 $\mu$M). Thus, the ARMS reaction works with much greater efficiency that the control if the mutation is present.

Step 2—The products of the PCR reaction (step 1 above) are used to seed the second PCR reaction. The second PCR reaction contains only one primer; the TAG sequence. The TAG primer is rich in G+C residues relative to the ex-TAG portion of the control PCR primers. This second PCR reaction is performed at a high annealing temperature which prevents the action of any carried-over control PCR primers. The TAG primers, however, are able to efficiently amplify the control and ARMS PCR products at the elevated annealing temperture. Therefore, the presence of the somatic mutation will lead to the formation of an ARMS and a control PCR product after step 2 PCR whereas in its absence only the control PCR product will be detected.

| Primer | Sequence 5' > 3' | % (G + C) |
| --- | --- | --- |
| TAG | GCGACCGGTCGCCGGACGC (SEQ ID NO:11) | 85.0 |
| CFTR Exon 3A Control 5' | GCGACCGGTCGCCGGACGCCaaataggacaa ctaaaatattt (SEQ ID NO:43) | 18.2 ex-TAG |
| CFTR Exon 3A Control 3' | GCGACCGGTCGCCGGACGCCttttcataatc acaaaaat (SEQ ID NO:38) | 15.8 ex-TAG |
| Common APC | GCGACCGGTCGCCGGACGCCgaaataaaaga aaagattggaactaggtcagc (SEQ ID NO:45) | 34.3 ex-TAG |
| Mutant-specific APC | GCGACCGGTCGCCGGACGCCggctgattctg aagataaactagaacccga (SEQ ID NO:44) | 43.3 ex-TAG |

Extension of Standard ARMS Test to include the detection of R553X and W1282X CF mutations: The development of an over ARMS test for the simultaneous detection of the closely linked mutations G542X and G551D is described in our European Patent Application, publication no. 0497527.

The incidence of the R553X mutation, also located in exon 11 and separated from G551D by only 5 base pairs is significant in CF affected individuals. As such, a method which would allow the simultaneous detection of all 3 mutations would prove valuable in determining CF carrier status. The simultaneous detection of the G551D and R553X mutations presents two additional technical problems:

i) direct competition of the G551D and R553X primers for target genomic DNA (5 bp separation, therefore ARMS primers themselves overlap—not a problem observed in the case of G542X/G551D overlapping ARMS)

ii) the G551D and R553X mutant PCR products would be indistinguishable by size difference using 3% agarose gels.

In an attempt to overcome the latter problem an elongated R553X mutant ARMS primer of 60 bp was synthesised (conventional ARMS primers are normally 20–30 bp) thereby creating a 39 bp size difference between the expected G551D and R553X mutant product bands.

Initially a 60 bp mutant ARMS primer (2134) containing an additional G-G destabilising mismatch at the −2 position of the 3' end but otherwise totally homologous to target DNA sequence, was included in the Standard ARMS test 'A' reaction mix at 1 $\mu$M concentration. R553X mutant product was detected and the ARMS primer was specific for only mutant DNA sequence. 621+1 normal, DF normal and G542X mutant product bands were unaffected by inclusion of the R553X primer. However G551D mutant product bands were no longer visible suggesting that the R553X mutant primer bound more effectively to target DNA thereby preventing any hybridisation of G551D mutant primer. Any further destabilisation of the R553X mutant primer at the 3' end (to allow the G551D mutant primer to bind target DNA also) was likely to compromise the yield of R553X PCR product. Likewise, reducing the severity of the G551D mutant primer mis-match was likely to compromise specificity. Consequently, a second elongated R553X mutant ARMS primer (2150) was synthesised which was no longer completely homologous to target DNA at the distal (5') end. The primer was otherwise identical to the original 2134 primer at the proximal (3') end and thus the ARMS specificity was unchanged.

When the 2150 R553X mutant ARMS primer (5' non-homologous tail) was included in the Standard 'A' reaction mix both R553X and G551D mutant products were detected i.e. the increased 5' destabilisation of the R553X mutant primer enabled the G551D mutant primer to compete for target DNA. Again the 621+1, DF508 and G542X product bands were unaffected.

The revised Standard ARMS test allowing detection of R553X in addition to 621+1, G551D, G542X and DF508 mutations has been tested with a number of positive control DNA samples (including and individual compound heterozygous for both R553X and G551D) and correct diagnoses obtained.

Although the R553X mutation could be easily detected using the method described above, the yield of R553X mutant product was generally lower than that observed for the other A-mix PCR products. In order to increase the amount of R553X product, and thereby obtain an overall balanced A-mix band profile, several approaches were evaluated:

i) increasing R553X mutant primer concentration ii) reducing mis-match severity iii) adding a secondary 'TAG' primer specific for the 5'non homologous tail of the R553X mutant primer The first two approaches were unsuccesful. Increasing the 2150 primer concentration to 4 $\mu$M did not markedly increase product yield. Using an R553X mutant primer containing no additional 3' destabilising mis-match increased product yield but was no longer specific for R553X mutant target sequence. (The effect of a G-T mismatch was not investigated).

A TAG primer (30 mer, 2173) specific for the 2150 5' homologous tail was also included in the revised Standard 'A' reactiron mix and the yield of R553X mutant product compared with that obtained using revised Standard 'A' mix (primer 2150) only. Inclusion of the TAG primer resulted in a marked increase in the amount of R553X product. Further, increasing the TAG: ARMS-tail primer ratio appeared to increase product yield. The optimal result was achieved using 2150 at 1 $\mu$M and the corresponding TAG primer at 3 $\mu$M. A second tailed ARMS primer (2180) identical to 2150 at the 3' end but modified 5' sequence was employed in conjunction with TAG primer 2164 but this particular combination failed to produce any R553X mutant product.

TABLE 1

| MUTATION | EXON | PRIMER | | SPECIFICITY |
|---|---|---|---|---|
| MIS-MATCH | | | | |
| W1282X | 20 | 2010 | N | C-A |
| | | 2011 | M | C-A |
| | | 2013 | N | G-A |
| | | 2012 | M | G-A |
| | | 2155 | N | A-A |
| | | 2109 | M | A-A |
| | | 2914 | C | |
| 1717-1 | INTRON 10 | 2065 | N | G-T |
| | | 2070 | M | G-T |
| | | 2066 | N | G-A |
| | | 2066 | M | G-A |
| | | 2067 | N | G-G |
| | | 2069 | M | G-G |
| | | 1823 | C | |

TABLE 2

| MUTATION | EXON | PRIMER | SPECIFICITY | MIS-MATCH | LENGTH | 5'-HOMOLOGY SEQ. | 5'-TAIL |
|---|---|---|---|---|---|---|---|
| R553X | 11 | 2189 | M | G-G | 30 | | |
| | | 2134 | M | G-G | 60 | YES | |
| | | 2150 | M | G-G | 60 | NO | TAG 1 |
| | | 2172 | M | | 60 | NO | TAG 1 |
| | | 2180 | M | G-G | 60 | NO | TAG 2 |

TAG 1 = 2173
TAG 2 = 2164

EXAMPLE 16

Analysis of "null" repeat units

Preparative MVR-PCR and Sequencing of Null Repeat Units: 100 ng samples of total DNA, of individual alleles separted from MboI digest of total genomic DNA by preparative gel eletrophoresis, were amplified in 30 µl reactions in the presence of 1.5 units AmpliTaq (Perkin-Elmer-Cetus), using the primers and PCR buffer system described in the above Examples. Reactions were cycled for 1.3 min at 96° C., 1 min at 68° C., and 5 min at 70° C. for 30 cycles on a DNA Thermal Cycler (Perkin-Elmer-Cetus), followed by a 2 cycle chase of 1 min as 68° C., 10 min at 70° C. Amplified products were electrophoresed through a 1.1% agarose gel and visualized by ethidium bromide staining. An appropriate "rung" in the MVR-PCR ladder required for sequencing was excised from the gel and purifed by electroelution onto dialysis membrane. The purified PCR product was reamplified with PCR primers 32-O and TAG using the same cycling conditions as before for a further 18 cycles. The double-stranded PCR product was re-purified by electrophoresis and eletroelution and sequenced directly.

MVR-PCR of null repeats: this was performed using primer 32-TAG-N (5 nM final concentration) or 32-TAG-J (10 nM final concentration) instead of the a-type or t-type specific primers 32-TAG-A and 32-TAG-T (for primer sequences see Table 3). Other conditions and the driver primers used (32-D or 32-O plus TAG) were as previously described.

Sequence Analysis of MS32 Null Repeat Units: we have previously described how haplotypic MVR maps from individual alleles can be determined, either from eletrophoretically-separated alleles or by pedigree analysis of digital codes generated by MVR-PCR from total genomic DNA. From this survey, three individuals were chosen, each of whom had an MS32 allele containing one or more null or O-type repeat(s) within the first 20 repeat units. Separated alleles or total genomic DNA was amplified by MVR-PCR to the point where PCR products could be visualised directly on agarose gels by staining with ethidium bromide; up to 20 repeat rungs on the MVR ladder could be generated (data not shown). For separated alleles, the rung two repeat units above the null repeat was excised from the gel, re-amplified and sequenced. For total genomic DNA, a suitable band specific to the relevant allele was identified at an a/t heterozygous rung position above the position of the O-type repeat, followed by purification and sequencing.

The sequences of the three null repeats characterised are shown in Table 3. All three shared the same A base deletion 3 bp 3' to the G/A polymorphic site which distinguishes a- and t repeat units. The null repeat unit sequences were otherwise normal and contained either G or A at the major polymorphic site. This single base deletion is sufficient to block priming by the MVR-PCR primers 32-TAG-A and 32-TAG-T; null repeats containing this variant are referred to as N-type repeats.

MVR-PCR of N-type Repeats: to determine the frequency of N-type repeats in MS32 alleles, a new MVR-PCR primer, 32-TAG-N, was designed to prime specifically off these repeats. This primer incorporates the TAG sequence as previously described and can be used in MVR-PCR as a replacement for the a- or t-type specific primer (Table 3, FIG. 17). The majority of individuals previously identified as containing alleles with null repeats were remapped using 32-TAG-N (FIG. 17). Most null repeats were positively identified by primer 32-TAG-N at the position previously identified from intensity differences in the A and T lanes (32-TAG-A, 32-TAG-T) as being heterozygous or homozygous for a null repeat. A minority of null repeat units failed to amplify with 32-TAG-N (FIG. 17, individuals 4 and 5), indicating the presence of additional repeat unit variant(s) which could not be detected by primers 32-TAG-A, -T or -N.

In a survey of the first 50 repeat units in 391 different Caucasian and Japanese alleles (18,790 repeat units in total), 285 repeats were null or O-type repeats (1.5%) and 241 of these repeats were detected as N-type (Table 3). Thus 84.5% of all null repeats were identified using the 32-TAG-N primer and therefore share the A deletion; the possibility of additional variation between N-type repeats which does not block priming by 32-TAG-N cannot however be excluded. The incidence of N-type repeats is very similar in Caucasians and Japanese (1.39% and 1.26% of all repeats, respectively).

Sequencing of One of the Minor Null Repeats: In an attempt to characterise further the remaining null repeat units not detected by 32-TAG-N, a single repeat unit of this type was sequenced from a Japanese allele. This J-type repeat contained a C→T transition immediately 3' to the major G/A polymorphic site in an otherwise normal repeat unit sequence (Table 3). A new PCR primer (32-TAG-J) designed to assay this sequence variant was tested on all DNA samples that contained null repeat units not detected by 32-TAG-N. Only 3 repeat units in 2 different Japanese alleles were detected with this primer (data not shown). The remaining null repeat units not detected by 32-TAG-N or 32-TAG-J are referred to as U-type (undetectable) repeats and contain as yet uncharacterised repeat variant(s). The frequency of U-type repeats varies substatially between Caucasian and Japanese alleles (0.18% vs. 0.56% of all repeat units, respectively).

Distribution of null repeats in MS32 alleles: 23% of alleles (91 alleles out of 391 different Caucasian and Japanese alleles typed) contained one or more null repeats within the first 50 repeat units. Null repeats appear to occur with equal likelihood at any position within the mapped region of these alleles (FIG. 18A). Analysis of the number of null repeats in different alleles (FIG. 18B) showed clear evidence of clustering of nulls, particularly N-type repeats, within a limited number of alleles. In one extreme case, 12 N-type repeats were present within the first 50 repeats, and in another bizarre case, an allele contained a succession of 8 U-type repeats followed by NaNN embedded in an allele otherwise fixed for a-type repeats (FIG. 18C).

Although the vast majority of MS32 alleles so far typed have different MVR maps, different alleles can nevertheless show internal regions of significant map similarity suggesting recent common ancestry of these allele segments (FIG. 19). These shared haplotypic segments occur much more frequently at one end of MS32 alleles, distal to the unstable proximal region mapped by MVR-PCR which contains a localised mutation hot-spot. 59% of the 391 different MS32 alleles so far mapped can be aligned into 40 different groups of related alleles. 77% of the 91 alleles that contain null repeat units fall within these aligned groupings. In every case where two or more alleles shared a null repeat at equivalent positions within the share haplotype, MVR-PCR showed that the null repeats were of identical types (almost always N-type repeats) (FIG. 19, groups A, B). Additional N-type repeats restricted to just one of the alignable alleles almost always lay outside the shared haplotypic region. In contrast, U-type repeats tend to occur sparadically within otherwise preserved haplotypes shared by related alleles and are usually confined to only one of the aligned alleles (FIG. 19, group C).

Effect of Null Repeats in Paternity Testing: to use digital MVR codes from total genomic DNA for paternity analysis, it is necessary to identify correctly code positions heterozygous for null repeats (a/O, t/O). However, since null repeats are scarce, the presence of a null-containing paternal allele in a child will add substantially to the ability of MVR-PCR to exclude non-fathers of such a child. To estimate the overall effect of null repeat units in paternity testing, the MVR codes of 141 different Caucasian mother-child duos were each compared with 302 different unrelated Caucasians over the first 50 repeat units (45,582 different mother-child-nonfather trios in total). On average, 9.6 exclusions were obtained per comparison, of which 4.6 were paternal-specifc and the remainder directionally ambiguous (FIG. 19A); 97.5% of non-fathers showed at least one paternal-specific exclusion, and 99.86% showed one or more exclusions in total (paternal-specific plus ambiguous). Since maternity is seldom an issue in paternity cases, then the first 50 repeats contain enough information to exclude on average 99.86% of non-fathers. To determine the contribution of null repeats to this efficiency, the simulated paternity cases were re-evaluated after elimination of all code positions in each child heterozygous for a null repeat (a/O, t/O), including both authentic null repeats and non-existent 'null' repeats from beyond the end of short alleles (FIG. 19B). As expected, the mean number of exclusions fell significantly, causing a drop in the proportion of non-fathers showing exclusions from 99.86% to 99.50% (97.5% for paternal-specific exclusions only).

These estimates for the efficiency of non-paternal exclusion are a mean over all mother-child duos. Variation between duos in levels of exclusion was therefore investigated (FIG. 19C). The proportion of the 302 'non-fathers' excluded varied substantially from duo to duo, depending on the precise nature of the MVR codes in the mother and child. In the worst case, only 95% of non-fathers could be excluded (74% if only paternal-specific exclusions are used). As expected, these estimates are worsened if null repeat positions are eliminated from the analysis.

Internal mapping of variant repeat units within minisatellites represents an important new approach both to DNA typing and to the analysis of allelic variability and minisatellite mutation processes. Work to date on minisatellite MS32 has concentrated on a G/A base substitutional polymorphism originally defined by the presence/absence of a HaeIII cleavage site within repeat units. A second common polymorphic site 2 bp from the variable G/A site has been found from sequence analysis of cloned MS32 (see Table 3) but has yet to be used for internal mapping. MVR-PCR has now revealed additional rare variants defined operationally as "null" repeats which cannot serve as priming sites for the MVR-PCR primers 32-TAG-A or -T. These variants have presumably arisen by repeat unit sequence mutation, and their incidence governed by a balance between mutation and fixation/extinction within and between repeat arrays by processes such as unequal exchange and replication slippage. The relative scarcity of null repeats makes them particularly useful for identifying related alleles and confirming the authenticity of allele alignments.

87% of null repeats in Caucasian alleles share a common variant, the N-type repeat, which can now be detected reliably by MVR-PCR. The widespread occurrence of N-type repeats in both Caucasian and Japanese alleles and their presence in amy groups of aligned alleles suggest that this variant arose fairly early in the evolution of MS32 alleles. Several different group of aligned alleles contain N-type repeats within a "NataNata" motif (FIG. 19), suggesting a "supergroup" of alleles sharing homologous patches of tandem repeats within alleles which are otherwise not obviously alignable.

The remaining null repeats include the rare J-type repeat and the as yet unsequenced U-type repeats. 8% of alleles contain U-type repeats, and the majority of these alleles (26/33) have only a single U variant over the region mapped, suggesting recent mutation without subsequent diffusion into neighbouring repeats. This is supported by U-containing alleles which fall within groups of alignable alleles; in each of the five cases where the U-type repeat lay within a haplotypic segment shared by several alleles, other alleles contained an a- or t-type repeat at the corresponding position (see FIG. 19, group C). This suggests either very recent repeat unit mutation from a or t to U, and thus sequence heterogeneity amongst different U-type repeats, or possibly that the U repeat is ancestral within a group of aligned alleles and has recently been replaced by an a- or t-type repeat by a process such as microconversion which does not affect repeat unit copy number or the flanking MVR map. Two probable instances of U-type repeat diffusion subsequent to mutation have been found. In one Japanese allele with two U repeats, the variants are contained within a perfect high-order tandem repeat of a 24 repeat unit segment commencing 3 repeat units from the beginning of the allele, and presumably contain the same variant (not shown). In the second case, an English allele contains a block of 8 U-type repeats (FIG. 18C) which again have presumably expanded from a single mutant repeat.

The existence of variant repeats with abnormal repeat length, for example the N-type repeat 28 bp rather than 29 bp long, could create problems in digital coding from genomic DNA, by moving the MVR ladders of each allele out of register. In practice however, aberrant length repeats do not appear to present a significant problem; in the worst individual so far found with 12N-type repeats in one allele and none in the other, the digital code could be unambiguously read for more than 50 repeat unit positions, although the normally perfect spacing of rungs on the ladder was slightly perturbed by the progressive misalignment of the two allele ladders (maximum misalignment of 12 bp for the 50 repeat unit PCR products 1714 bp long) (data not shown).

MVR-PCR can also be used for paternity testing, provided that heterozygous null positions (a/O, t/O) in diploid codes (3.0% of all positions) can reliably identified. Experience to date suggests that these positions can be identified with >90% reliability solely from band intensity information using primers 32-TAG-A and -T alone. The ability to detect definitively the substantial majority of null repeats using primers 32-TAG-N and -J substantially increases the reliability, to provide a single locus which is remarkably effective at excluding non-fathers, though limited by the high de novo mutation rate creating new MVR haplotypes at MS32.

TABLE 3

Sequence of MS32 variant repeat units and their distribution in the first 50 repeat units of Caucasian and Japanese alleles.

| Repeat type | Sequence | Caucasian(%) (n = 15536)[a] | Japanese(%) (n = 2868)[a] |
|---|---|---|---|
| a | 5'-GGCCAGGGGTGACTCAGAATGGAGCAGGY-3' SEQ ID NO:31 | | 73.575.1 |
| t | 5'-GACCAGGGGTGACTCAGAATGGAGCAGGY-3' SEQ ID NO:32 | | 25.022.9 |
| N | 5'-GRCC-GGGGTGACTCAGAATGGACGAGGY-3' SEQ ID NO:33 | | 1.26 1.39 |
| J | 5'-GGTCAGGGGTGACTCAGAATGGAGCAGGY-3' SEQ ID NO:34 | | 0 0.07 |
| U | unknown | 0.18 | 0.56 |

Y=C or T, R=G or A. a-, t-, N-, and J-type repeat units were detected by the following MVR-specific primers:

32-TAG-A, 5'-tcatgcgtccatggtccggaCATTCTGAGTCA-CCCCTGGC-3' (SEQ ID NO: 39);
32-TAG-T, 5'-tcatgcgtccatggtccggaCATTCTGAGTCA-CCCCTGGT-3' (SEQ ID NO: 40);
32-TAG-N, 5'-tcatgcgtccatggtccggaTCCATTCTGAGTCA-CCCCGG-3' (SEQ ID NO: 41);
32-TAG-J, 5'-tcatgcgtccatggtccggaCCATTCTGAGTCA-CCCCTGA-3' (SEQ ID NO: 42).

The 3'sequence of each primer (uppercase) is complementary to each repeat unit variant and is preceded by a common TAG sequence (lowercase) used to drive subsequent amplification. U-type repeat units are not amplified by any of these MVR-specific primers, a, number of repeat units scored in 324 Caucasian alleles and 59 Japanese alleles.

EXAMPLE 17

Allele 'knockout' MVR-PCR

The observed variation seen for diploid codes (no two individuals among 408 unrelated Caucasians and Japanese so far typed share the same diploid code) is based directly upon the massive variation of individual alleles. The estimate for the minimum number od distinguishable alleles present in current Caucasian populations is around 3500 (estimated from the number of different alleles observed in a sample of 337 mapped alleles, which contained 326 different alleles of which 316 were only sampled once). The true number of different alleles is certainly in excess of this and may be as high as $10^8$ for the total world population (based on known mutation rate and population size, Jeffreys et al., 1991). Allele mapping is providing remarkable insights into the evolution of minisatellites and the generation of new length alleles with, for the first time, preliminary evidence for the role of unequal interallelic exchange, or interallelic gene conversion, in the genertion of new mutant alleles (Jeffreys et al., 1991). We also predict that allele mapping will prove an invaluable tool in the analysis of human population divergence through the generation of allele groupings from which it may prove possible to derive both allele and human population lineages. The structure of individual MS32 alleles using MVR-PCR can be presently approached in two ways: First, by pedigree analysis of diploid codings and second, by mapping of individual separated alleles. Using family groups it is possible to derive incomplete allele maps from father, mother, single child trios and total unambiguous allele maps from father, mother and two children who share one allele in common. The use of such family groupings is however limited by availability and by the high de novo mutation rate of 1.2% per gamete at this locus. Alternatively, individual alleles from one person may be separated on the basis of size, using restriction digestion and preparative agarose gel electrophoresis. This approach is time consuming, tedious and requires reasonbly large amounts of DNA (miniumum around 5 μg total genomic DNA) plus the need for a preliminary experiment to determine allele sizes. Moreover this approach proves difficult for individuals with closely sized alleles and pseudohomozygous individuals. Some of these problems may be obviated by single molecule dilution (SMD) and PCR recovery (Monckton and Jeffreys, 1991), but this procedure has its own limitations, the main one being that it is applicable only to relatively small alleles that may be amplified in their entirety.

We used single stranded conformational polymorphism (SSCP) analysis, DNA sequencing and inter-species sequence comparisons to identify three common polymorphisms in the flanking DNA of MS32. The sequence information thus gained was used to design PCR based diagnostic tests for allelic state and, through the use of allele specific primers, haplotype specific MVR-PCR of MS32 alleles in heterozygous individuals (i.e. 'knockout' of one allele). We also show that the use of haplotypic primers may be used to obtain unambiguous individual specific diploid codes, or unambiguous single allele codes, from mixed DNA samples, of obvious potential in forensic applications.

Materials and methods

General PCR assays: PCR was performed using the buffer conditions and primer sequences and concentrations previously described (Jeffreys et al., 1991; legend to FIG. 2), and with the primer sequences as given in the legend to FIG. 21, using 100 ng of input genomic DNA in 7.5 μl reactions, unless stated otherwise. Cycling conditions were 1 minute denaturation at 96° C., 1 minute primer annealing at A° C. and E minutes extension at 70° C.

DNA sequencing: Single stranded template DNA was generated by asymmetric PCR (Gyllensten and Erlich, 1988) and sequenced in the presence of the detergent NP-40 by the di-deoxy chain termination method as previously described (Bachman et al., 1990) using T7 polymerase (Pharmacia).

MVR-PCR: this was carried out with the fixed flanking primers 32-0, 32-H2C or 32-D2 using an annealing temperature (A) of 69° C. and an extension time (E) of 5 minutes for 18 cycles, with all other procedures as previously described (Jeffreys et al., 1991). Knockout MVR-PCR using the flanking primer 32-HIC was performed with an annealing temperature (A) of 64° C. for five cycles and 60° C. for 13 cycles, again with all other procedures as previously described.

Results: MS32 MVR-PCR analysis is directed from a unique sequence primer (32-O, 32-D or 32-B) located in the 5' flanking sequence of MS32 into the minisatellite array (FIG. 21). The original X clone containing MS32 includes only a further 425 bp of DNA 5' to the first minisatellite repeat unit. This region was previously sequenced in the human clone (Wong et al, 1987) and partially sequenced in a selection of primates (Gray and Jeffreys 1991). To search for polymorphisms in this region in humans, primer 32-OR was designed and used in conjunction with 32-B (FIGS. 21 and 22) to amplify the 348 bp of DNA immediately flanking the most variable and unstable end of the minisatellite which is analysised in MVR-PCR.

Identification of three common polymorphisms in the flanking DNA: PCR amplification followed by restriction digest analysis of this region from 12 unrelated Caucasian individuals revealed a HinfI restriction site dimorphism in this region (designated as Hf+ for presence of the HinfI restriction site and Hf- for absence of the HinfI restriction site). This region showed no polymorphisms using the restiction enzymes BglI, DdeI, Fnu4HI or AluI in the same 12 unrelated individuals. Direct DNA sequencing of this region from PCR amplification products from a heterozygous individual (HF+/Hf-) and a single molecule separated Hf- allele from a second heterozygous individual (Monckton and Jeffreys, 1991) revealed the polymorphism as a C (presence of HinfI restriction site, Hf+) to T transition (absence of HinfI restriction site, Hf-) at position 143 (FIG. 23, Table 4).

PCR-SSCP analysis (Orita et al., 1989) of the entire flanking region (32-OR to 32-B) in 8 CEPH parents homozygous for Hf+ revealed another common polymorphism (see segregation analysis of family 1416, FIG. 22A). Direct DNA sequencing of the PCR product amplified from individuals homozygous for the two forms and their heterozygous father showed the polymorphism to be due to a C to G transversion at position 80, designated Hump 1 (HUMan Primate variant 1, alleles H1$^C$ and H1$^G$), FIG. 23, Table 4). Further sequence comparisons between the sequences obtained here and those obtained previously revealed another polymorphic site within this flanking region, a C to T transition at position 241, designated Hump2 (HUMan Primate variant 2, alleles H2$^C$ and H2$^T$), (FIG. 23, Table 4).

Primate sequence comparisons: Direct comparisons of the flanking region between the cloned human sequence (Wong et al., 1987) and those previously obtained for Chimp, Gorilla and Orang-utans (Gray and Jeffreys, 1991) allowed the derivation of a great ape/human ancestral sequence for this region (using Orang-utans as the outgroup), (FIG. 23). Nine sites of sequence divergence exist between man and the primate ancestral sequence and all three of the described polymorphic sites so far identified are contained within this group (Table 4). We reasoned that the observed differences between the cloned human sequence and the derived ancestral sequence were likely to be due to mutation events that occurred subsequent to the human—great ape split, approximately 6–8 million years ago (Koop et al., 1986). We further reasoned, assuming a fixation time of around 1 million years and a random timing for the generation of new alleles within that 6–8 million years, that approximately ⅐ (i.e. 1–2) of the sites would have arisen in the past 1 million years, thus would be unlikely to have progressed to fixation and could still be polymorphic within the present human population. This type of analysis not only produces an estimate for the number of likely polymorphic sites but also direct information as to their probable location. Most significantly it allows the predication of easily assayable restriction enzyme sites that differ between the human clone and the primate consensus. Obviously the success of this approach is highly dependent on the initial human sequence obtained, since if the chromosome from which the human sequence was gained carries the ancestral allele at a genuinely polymorphic site then such a site will not be identified by this type of analysis. Of the nine sites of sequence divergence identified, six produced changes in commonly available restriction enzyme sites (BglI, BspMI, HinfI and XbaI, see Table 4) and all wer assayed in 20 unrelated individuals amplified with primer pair 32-OR and 32-B. Other than the previously identified HinfI polymorphic none of the six sites examined were found to be commonly polymorphic. The base substitutions at sites 80, 94 and 241 do not affect recognition sequences for any commonly available restriction enzymes. Sites 80 and 241 were previously shown to be polymorphic by SSCP and sequence analysis (Hump1 and Hump2), whilst sequence analysis of seven amplified human alleles and the human clone has not revealed the persistence of the ancestral allele at position 94.

Assays for the polymorphisms and heterozygosity analysis: As a simple restriction site dimorphism the Hf polymorphism was very easily typed by standard PCR amplification (using primer pair 32-OR and 32-B) and subsequent HinfI digestion (FIG. 22B). Typing of this polymorphism across the 80 parents in the CEPH panel of families and across 101 unrelated Japanese individuals showed a heterzygosity level of 31% for this polymorphism in both populations (Table 22).

Unfortunately neither Hump 1 nor Hump2 created or destroyed restriction enzyme sites within the flanking region and thus an alternative approach to determining allele status at these polymorphic sites was required. For Hump2 a single tube four primer PCR assay was developed (FIG. 22C). Two opposing primers specific for the two alternative alleles were created, 32-H2C (for amplification from the H2$^C$ allele) and 32-H2AR (for amplification from the H2$^T$ allele), and used in conjunction with the universal primers 32-OR and 32-B (see FIG. 21). An individual homozygous from the H2$^T$ allele produces a 259 bp band corresponding to the PCR product from primer pair 32-H2AR and 32-B, as well as the 364 bp internal control band derived from the universal primers 32-OR and 32-B. In contrast an individual homozygous for the H2$^C$ allele produces a 142 bp band corresponding to the PCR product from primer pair 32-H2C and 32-OR, as well as the 364 bp internal control band. Heterozygous individuals (H2$^C$/H2$^T$) produce all three bands. Typing of the Hump2 polymorphism across the 80 parents in the CEPH patent of families and across 101 unrelated Japanese individuals showed heterzygosity levels of 48% and 16% respectively (Table 5). Unfortunately the Hump 1 polymorphic site lies in a very A/T rich region of DNA (26% G/C in the 50 bp surrounding Hump1) and an alternative strategy was required to assay this site. The mismatched primer 32-H1B primer just 5' to the Hump 1 polymorphism and forces the incorporation of a 3'terminal G rather than the A present in genomic DNA. Use of this primer during low stringency PCR allows incorporation of this transition into resulting PCR products. This forced insertional mutation creates or destroys an easily assayable Bsp1286I restriction enzyme site dependent on allelic state at the Hump1 locus (H1$^G$ derived products amplified with 32-H1B are cut by Bsp1286I). Unfortunately the low annealing temperture required to ensure the A/T rich 32-H1B primer incorporating the terminal mismatch primes efficiently prevented the direct use of total genomic DNA as a PCR template. Thus a preliminary amplification of the entire flanking region with primer pair 32-OR plus 32-B (as used in the Hf assay) was required to generate seed DNA for use in a nested 32-NR (32-NR primes just 5' of 32-OR and acts as a nested primer directed into the 5' flanking DNA of MS32) to 32-H1B amplification (FIG. 21). Simple genotyping of this polymorphism was then achieved by Bsp1286I digestion and agarose gel electrophoresis (FIG. 22A). Typing of the Hump 1 polymorphism across 40 parents inthe CEPH panel of families showed a heterozygosity of 43% (Table 5).

Knockout MVR-PCR: These flanking polymorphisms can be used to map individual MS32 alleles from total genomic diploid DNA by the use of allele specific primers located in the flanking DNA. PCR primer 32-D2 spans the site of the Hf polymorphism and was used as an allele specific MVR-PCR primer. Using 32-D2 as the fixed primer in the flinking DNA it was possible to amplify only MS32 alleles linked to the Hf$^+$ site i.e. to 'knockout' the amplification of the Hf–linked allele. For heterzygous individuals (Hf$^+$/Hf$^-$) it was possible to obtain the allele map from the Hf$^+$ linked allele direct from total genomic DNA (using primer 32-D2) and for the Hf– linked allele by substraction of the Hf+allele from the diploid code derived from a standard MS32 MVR-PCR using a universal flanking primer (32-D, 32-O or 32-B) (FIG. 24).

PCR primer 32-H2C can also be used as an allele specific MVR-PCR primer; using this as the fixed primer in the flanking DNA it is possible to knockout H2$^T$ linked alleles and amplify only MS32 alleles linked to H2$^C$. As with the Hf polymorphism in heterozygous individuals (H2$^C$/H2$^T$) it is possible to obtain the allele map from the H2$^C$ linked allele direct from total genornic DNA (using primer 32-H2C) and for the H2$^T$ linked allele by substraction of the H2$^C$ allele from a standard MS32 MVR-PCR (FIG. 24). Similarly the HumpI specific primer 32-H1C may also be used for knockout MVR-PCR in heterozygous individuals, (FIG. 24).

Haplotype analysis of flanking DNA polymorphism: Haplotypic analysis of the polymorphisms to each other and to the minisatellite alleles may be achieved in a variety of ways. Pedigree analysis is the simplest, and has been applied to the three flanking polymorphisms and the minisatellite array for 40 CEPH families. Haplotypes of each flanking polymorphism with respect to the minisatellite array can be directly achieved by knockout MVR-PCR. PCR based systems for direct haplotype analysis and detailed haplotype studies are on-going. Preliminary results however, suggest that significant linkage disequilibrium exists between all the polymorphic sites, but in no case is the observed disequilibrium absolute. Results for the haplotyping of the Hump2 and Hf polymorphisms in the parents of the 40 CEPH families are presented in Table 5. Based on these figures approximately 63% of Caucasian individuals are heterozygous at the variant Hf and/or Hump2 sites and can therefore have single alleles mapped by knockout MVR-PCR.

Applications to mixed DNA samples: As described above MS32 MVR-PCR is likely to have major applications in forensic science, an application for which mixed DNA samples are often encountered e.g. mixed victim and assailant's blood in violent attacks, vaginal swabs in rape cases and mixed semen samples in multiple rape cases, or mixed partner/rapist semen samples. We have shown above that ambiguous diploid codes may be derived from mixtures of DNA down to approximately 10% admixture, and that in cases where a pure sample of one of the DNAs, e.g. victim, is available a high level of exclusionary power is achieved (on average 99.9993% of false suspects excluded). Even in cases were neither sample is available in a pure form valuable information to exclude false suspect may still be derived. However, mixtures of DNA below 10% and mixtures of two or more DNAs are less amenable to standard MVR-PCR analysis. To investigate the potential forensic applications to knockout MVR-PCR we simulated mixed DNA cases under two, of many, possible scenarios: 1, the mixture of a H2$^C$ homozygous assailand with H2$^T$ homozygous victim, allowing use of the H2$^C$ specific primer 32-H2C to selectively amplify only the assailant's alleles, thus deriving the assailant's diploid code; and 2, the mixture of a Hf$^+$/Hf– heterozygous assailant with a homozygous Hf– victim allowing use of the Hf$^+$ specific primer 32-D2 to specifically amplify only one of the assailant's alleles. Two suitable individuals were identified i.e. a H2$^T$/Hf$^T$, Hf–/Hf– 'victim' and a H2$^C$/H2$^C$. Hf$^+$/Hf– 'assailant' and DNA mixture from 1:1 to 1:200 (victim: assailant) made and MVR-PCR analysis performed with the appropriate primer combinations (see FIG. 25). Allele specific primer 32-H2C can be used to amplify unambiguously only the assilant's alleles down to mixtures of at least 1:10 (150 ug of victim DNA: 15 ng of assailant DNA). For the 1:50 mixture only the assailants diploid code was seen, but some variation in band intensity was observed as the lower limit for the quantity of input DNA was approached (only 3 ng of specific input DNA). Below 1:50 mixtures extra cycles of PCR were required to maintain detectable levels of product, with resulting increased background signal derived from mispriming from the victim's DNA; as a consequence unambiguous information was no longer derived. Nevertheless it may be possible to derive an ambiguous code at mixtures far lower than possible using standard MVR-PCR, especially if enough material is available to permit multiple amplifications allowing derivation of a consensus code if stochastic loss of PCR products is observed for very small starting amounts of DNA. The Hf$^+$ specific primer (32-D2) shows less allele specificity than the Hump2 allele specific primer, but it does allow the derivation of single allele codes for mixtures down to 1:2. Primer 32-D2 was not initially designed as an allele specific primer but fortuitously spanned the Hf polymorphism. An alternative primer designed specifically to access the Hf polymorphism should amplify more selectively and allow derivation of unambiguous codes at lower levels than achievable with 32-D2.

The power of using single allele codes to identify individual based on comparisons with their diploid MVR-PCR code was also assessed. Each of the 411 different alleles in our present allele database were used to screen the diploid database of 408 unrelated individual codes; the number of exclusions per false suspect is plotted in FIG. 26. 99.87% of false suspects were excluded using information from the first 50 repeats, with a mean of 10.7 exclusions per case. However, many of the alleles in our database were derived from mother-father-single child trios and thus contain some ambiguous positions; this situation does not accurately reflect the circumstances likely to arise in genuine forensic applications where the code of the allele under test will have been generated unambiguously by knockout MVR-PCR. We therefore repeated this analysis using 235 completely mapped alleles and, as expected, the level of exclusion rose slightly to 99.9%, with a mean of 11.3 exclusions per case. The power of exclusion for any one allele though was not uniform with the majority of alleles excluding all false suspects (96.11% and 96.60% respectively for total and unambiguous allele databases), with the major loss in overall exclusionary power being due to a limited subset of alleles with poor discriminatory power. Those alleles which failed to exclude greater than 99% of false suspects were found upon examination to be 'a' rich homogeneous alleles (i.e. almost completely comprised of a-type repeats, data not shown). Nonetheless, even the worst unambiguous allele still managed to exclude greater than 95% of false suspects, an exceptionally high level for the worst case scenario of one allele of one locus. In summary more than 98.5% of single alleles exclude more than 99% of false suspects. Using the Hf and Hump2 haplotype frequencies derived from the analysis of the 40 CEPH families (160 haplotypes) an approximate estimate for the number of mixed DNA samples to which unambiguous diploid or single allele mapping could theoretically be applied using the Hf and Hump2 discriminatory system can be calculated (see Table 7; this analysis assumes the mixes are of sufficient quality and in reasonable proportions to allow unambiguous MVR-PCR to be performed). It can be seen that in approximately 25% of cases an unambiguous diploid code would be derivable from a mixed DNA sample, and in up to 50% of cases either diploid code, or single allele, information would be recoverable. Use of the Hump1 polymorphism in this type of analysis should further improve the proportion of mixed DNA scenarios to which MVR-PCR based identification could be applied.

Thus far we have identified three common polymorphisms in the immediate 348 bp of DNA flanking the minisatellite locus D1S8. For each polymorphic site we have developed rapid and reliable PCR based tests for allelic state and have determined allele frequencies in two major populations. Each locus appear to be a Hardy-Weinberg equilibrium, whilst significant, but not absolute, linkage disequilibrium exists between sites. The use of such polymorphic sites to design allele specific primers has been demonstrated as well as their use in single allele or knockout MVR-PCR. With a combined heterozygosity in the flanking DNA of in excess of 63%, the large scale mapping of separate alleles in large numbers of unrelated individuals becomes feasible, with obvious potential for the generation of large allele databases, allele groupings and possible derivation of allele and human lineages. Mapping of more alleles and concurrent haplotyping of the flanking polymorphisms should shed more light on the mutation processes involved in maintaining ultravariability at this locus. It will also help to assess the extent to which interallelic exchange is involved in the generation of new alleles, and to determine whether or not a local recombinational hotspot is indeed present at this locus. The identification of additional polymorphisms in the flanking DNA of MS32 will further increase the proportion of individuals heterozygous for at least one of the flanking sites, increasing both the number of single allele maps directly obtainable and providing more flanking DNA markers for the detailed analysis of the molecular processes operating at this hypermutable locus.

The existence of additional unknown flanking polymorphisms which affect 'universal' flanking primers (32-O, 32-D and 32-B) could lead to inadvertent allele knockout during MVR-PCR (as originally found for the flanking primer 32-D2) and the generation of incorrect diploid code. However, such knockout of an allele will produce an apparently homozygous pattern devoid of heterozygous (a/t) positions; such patterns are easily identified and such apparently homozygous individuals can be retested with other flanking primers to check for true homozygosity (or possibly heterozygosity for a null MS32 allele carrying a deletion of flanking DNA and flanking primer sites, though no such allele has been identified).

A preliminary study of the potential forensic applications of knockout MVR-PCR in analysing mixed DNA samples has also been described, although a more rigourous and extensive study is needed to confirm the full scope of such applications. The optimization of PCR primer allele specificity and the characterisation of additional polymorphisms should increase the proportion of mixed DNA smaples to which MVR-PCR can be applied. The application of knockout MVR-PCR to multiple mixed DNAs has not be tested directly, but they too should prove tractable, although the probability of obtaining unambiguous codes will decrease as the number of DNAs involved increases. Knockout MVR-PCR under some circumstances can be used to obtain information for mixtures containing as little as 1% admixture of DNA; this represents a considerable improvement over other techniques such as Southern blot hybridisation using single locus hypervariable probes. Mixed DNA samples also occur in analytical contexts other than forensics, e.g. monitoring of transplant success in bone-marrow transplants, and such situations should prove amenable to the same techniques. We have also investigated the potential use of primate consensus sequences to pin-point sites of potential variation in present day human populations. Although unsuccessful in further increasing the number of polymorphic sites found in this investigation, an initial analysis would have identified the three sites now known to be polymorphic in this region. We note that where primate sequence information already exists it may be used to more rapidly target potentially polymorphic sites in humans.

TABLE 4

Human/primate ancestral sequence variant sites in the MS32 flanking region

| No. | Position | Human Clone Sequence Differences | Human/ Ancestral | Human Clone/Ancestral Restriction Site | Polymorphism in Caucasians | Polymorphic Locus Name |
| --- | --- | --- | --- | --- | --- | --- |
| 1 | 80 | C | G | none | + | Hump1 |
| 2 | 94 | G | A | none | —* | |
| 3 | 127 | C | A | XbaI+/− | — | |
| 4 | 143 | C | T | HinfI+/− | + | Hf |
| 5 | 197 | G | T | HinfI+/− | − | |
| 6 | 207 | A | G | BspMI−/+ | − | |
| 7 | 241 | C | T | none | + | Hump2 |
| 8 | 309 | G | A | BglI+/− | − | |
| 9 | 319 | C | T | BglI+/− | − | |

*Only 7 chromosomes have been analysed for this locus.

TABLE 5

MS32 flanking polymorphism allele frequencies

| Locus | Allele | Caucasian Frequency | Number | Japanese Frequency | Number |
|---|---|---|---|---|---|
| Hump1 | G | 0.69 | 55 | ND | ND |
|  | C | 0.31 | 25 | ND | ND |
| HF | + | 0.81 | 129 | 0.81 | 163 |
|  | − | 0.19 | 31 | 0.19 | 39 |
| Hump2 | C | 0.59 | 94 | 0.91 | 184 |
|  | T | 0.41 | 66 | 0.09 | 18 |

ND = Not done

TABLE 6

Caucasian haplotype frequencies for the Hf and Hump2 polymorphisms

| Hf-Hump2 Haplotype | Frequency | Observed Number* |
|---|---|---|
| +C | 0.54 | 86 |
| −C | 0.05 | 8 |
| +T | 0.27 | 43 |
| −T | 0.14 | 23 |

*$X^2$(ldf) = 17.85, a significant deviation from a null hypothesis of random association.

TABLE 7

Theoretical estimation of the level of information obtainable from mixed DNA samples using the Hf and Hump2 allele specific primers in NVR-PCR

| | | Assailant's Haplotypes | | | | | | | | | |
|---|---|---|---|---|---|---|---|---|---|---|---|
| | | +C | +C +C | +C | −C | −C −C | +T | +T | −T | | |
| | | +C | −C +T | −T | −C | +T −T | +T | −T | −T | | |
| | f% | 28.9 | 5.4 28.9 | 15.5 | 0.3 | 2.7 1.4 | 7.2 | 7.7 | 2.1 | | |
| V | +C 28.9 | 0 | 1 1 | 1 | 2* | 2 2 | 2* | 2 | 2* | | |
|  | +C | 8.4 | 1.6 8.4 | 4.5 | 0.1 | 0.8 0.4 | 2.1 | 2.2 | 0.6 | | |
| i | +C 5.4 | 0 | 0 1 | 1 | 0 | 1 1 | 2* | 2* | 2* | | |
|  | −C | 1.6 | 0.3 1.6 | 0.8 | 0 | 0.1 0.1 | 0.4 | 0.4 | 0.1 | | |
| c | +C 28.9 | 0 | 1 0 | 1 | 2* | 1 2* | 0 | 1 | 2* | | |
|  | −T | 8.4 | 1.6 8.4 | 4.5 | 0.1 | 0.8 0.4 | 2.1 | 2.2 | 0.6 | | |
| t | +C 15.5 | 0 | 0 0 | 0 | 0 | 0 0 | 0 | 0 | 0 | | |
|  | −T | 4.5 | 0.8 4.5 | 2.4 | 0 | 0.4 0.2 | 1.1 | 1.2 | 0.3 | | |
| i | −C 0.3 | 2* | 1 2 | 2 | 0 | 1 1 | 2* | 2 | 2 | | |
|  | −C | 0.1 | 0 0.1 | 0 | 0 | 0 0 | 0 | 0 | 0 | | |
| M | −C 2.7 | 0 | 0 0 | 0 | 0 | 0 0 | 0 | 0 | 0 | | |
|  | +T | 0.8 | 0.1 0.8 | 0.4 | 0 | 0.1 0 | 0.2 | 0.2 | 0.1 | | |
|  | −C 1.4 | 2* | 1 2* | 1 | 0 | 1 0 | 2* | 1 | 0 | | |
|  | −T | 0.4 | 0.1 0.4 | 0.2 | 0 | 0 0 | 0.1 | 0.1 | 0 | | |
|  | +T 7.2 | 2* | 2 1 | 2 | 2* | 1 2 | 0 | 1 | 2* | | |
|  | +T | 2.1 | 0.4 2.1 | 1.1 | 0 | 0.2 0.1 | 0.5 | 0.6 | 0.1 | | |
|  | 7.7 | 2* | 2* 1 | 1 | 2* | 1 1 | 0 | 0 | 0 | | |
|  | −T | 2.2 | 0.4 2.2 | 1.2 | 0 | 0.2 0.1 | 0.6 | 0.6 | 0.2 | | |
|  | −T 2.1 | 2* | 2 2 | 1 | 2* | 2 1 | 2* | 1 | 0 | | |
|  | −T | 0.6 | 0.1 0.6 | 0.3 | 0 | 0.1 0 | 0.1 | 0.2 | 0 | | |

Notes: The upper figure is the number of assailant's alleles for which code could be derived (where information on both alleles is recoverable = at least one allele separately recoverable) and the lower figure is an estimate for the percent likelihood of this scenario being encountered. Haplotype frequencies (f) are based on a sample of 160 Caucasian chromosomes (Table 3).

EXAMPLE 18

MVR-PCR analysis of MS31A

The D7S21 locus (MS31A) is a minisatellite with an allele size range of 2–13Kb. It exhibits very high (99%) allele length heterozygosity that reflects extreme variability in tandem repeat copy number. Sequence analysis of MS31A alleles reveals that, like most minisatellites, there are polymorphic positions within the repeat units generating minisatellite variants repeat units (MVRs). However, MS31A is atypical in that all repeat units so far characterised at this locus have the same length (20 bp) (Wong et al., 1987). These attributes suggested that MS31A would be an ideal candidate for internal mapping of minisatellite repeat unit variation by applying the same MVR-PCR technique as used for D1S8 (MS32) (Jeffreys et al., 1991). An MS31 allele, cloned from a λ library of size fractioned human genomic DNA, has been sequenced. The Sau3AI fragment has 402 bp of 5' flanking DNA, followed by a large number of minisatellite repeats (MS31A) which are separated by 15 bp from an adjacent minisatellite (MS31B). The latter is truncated in cloned MS31 due to the presence of a Sau3AI site in one of its repeat units (Armour et al., 1989). Almost all of the variability at MS31 is due to repeat copy number variation at MS31A. Sequence analysis of cloned MS31A has revealed two adjacent sites of base substitutional polymorphism (G/A followed by C/T) in its repeat units. The second of these is potentially more informative for MVR-PCR, since MS31A alleles contain roughly even numbers of these two types (C/T) of repeat units. The map of the MS31 locus (FIG. 27) indicates that one end of MS31A alleles is far more amenable to MVR mapping than the other, and that the C/T polymorphism should be directly accessible for analysis by mapping from this 5' end. The proximity of MS31B to MS31A would make it difficult to design flanking PCR primers complementary to the 3' end of MS31A. Furthermore, access to the more informative variant repeat unit polymorphism would require the design of degenerate MVR-PCR primers spanning the less informative variant position within the repeats. Another advantage of assaying internal repeat unit variation at the 5' end of MS31 is that the existence of polymorphic sites in the flanking DNA can be exploited in the design of allele specific flanking primers. One such site, generating an AluI RFLP (FIG. 27) originally identified by Souther blot analysis, has been used in this way.

Methods: All PCR reactions used the buffer system described previously (Jeffreys et al., Cell, 1990, 473–485). MS31 MVR-PCR was performed as follows. 50–100 ng of genomic DNA, or the equivalent quantity of a single MS31 allele separated from an MboI digest of genomic DNA by preparative gel electrophoresis, was used as the template in 7 μl MVR-PCR reactions using the primers 31A and Tag at a concentration of 1 μM plus either 40 μM 31-Tag-A or 20 nM 3 1-Tag-G and 0.25 units AmpliTaq -(Perkin-Elmer-Cetus). Amplification was carried out by denaturing at 96° C. for 1.3 min followed by annealing at 69° C. for 1 min and extension at 70° C. for 3 min, repeated for 22 cycles and followed a chase of 67° C. for 1 min and 70° C. for 10 min. PCR products and 1 μg ΦX174 DNA x HaeIII size markers were electrophoresed through a 35 cm long 1.2% agarose (Sigma Type 1) gel in 89mM Tris-borate (pH 8.3), 2 mM EDTA, 0.5 μg/ml ethidium bromide (TBE), until the 118 bp marker band reached the end of the gel. The gel was then Southern blotted for 2 hours uing Hybond-N FP (Amersham) hybridisation transfer membrane. The membrane was dried and the DNA crosslinked to it by exposure to UV radiation from a transilluminator for 40 secs. It was then prehybridised at 65° C. for 30 mins. in 20 ml 0.5M Na phosphate (pH 7.2), 7% SDS, 1 mM EDTA and hybridized at 65° C. overnight in 20 ml of the same solution containing 32P-oligolabelled probe (the 4.5 kb Sau3AI minisatellite insert isolated from clone pMS3 1; Wong et al., Ann. Hum. Genet., 1987, 51, 269–288). The membrane was washed in a total of 100 ml 0.1 x SSC, 0.01% SDS, with changes of washing solution every 10 mins. Visualisation was carried out by autoradiography overnight at −70° C. without an intensifier screen.

MS31 MVR-PCR on separated alleles: To carry out MVR-PCR on MS31A, two MVR-specific primers were designed, 31-Tag-A and 31-Tag-G (FIG. 27). These primers comprise 19 nucleotides complementary to the minisatellite repeat unit, terminating at the C/T polymorphic MVR site and are preceded by the Tag sequence identical to that used in MS32 MVR-PCR above. Use of low concentrations of one or other of these primers coupled with high concentrations of the Tag driver primer and a primer at a fixed site in the 5' flanking DNA (310R, 31A, 31C, 31F, 31AluI+, 3 1AluI−; see FIG. 27) should generate sets of MVR-PCR products extending from the flanking site to each variant repeat unit of a particular type.

34 Caucasian MS31A alleles were separated by preparative gel electrophoresis from Sau3AI digests of genomic DNA. Each allele was amplified by MVR-PCR and the products detected by Southern blot hybridisation with $^{32}$-P-labelled MS3 1 probe (FIG. 28). In each case complementary ladders of PCR products were generated from 31-Tag-A and 31-Tag-G, from which the allele codes could easily be scored. In some cases allele codes could be read for over 100 repeat units into the tandem repeat array.

Repeat unit composition of MS31A alleles: Each mapped allele was encoded as a string of a-type and t-type repeat units. a-type repeat units are detected by 31-Tag-A and carry the "T" base at the polymorphic C/T site. t-type repeats carry the "C" variant and are detected by 31-Tag-G. This coding ensures compatibility with computer software developed for MS32 MVR-PCR coding.

In contrast to MS32, MS31A alleles contain a good balance of the two repeat unit types (Table 8) and these are evenly interspersed along alleles (FIG. 28), giving fewer clusters of a particular repeat type and fewer alleles in which one repeat unit type predominates. There are also fewer short alleles at MS31A. As with MS32 a small proportion (around 2%) of repeat units fail to amplify with either MVR-specific primer, indicating the presence of additional "null" or 0-type variant repeats. These 0-type repeats tend to cluster in a limited number (10/34) of alleles, some of which are clearly related. However, additional variants which quantitavely affect amplification efficiency, and hence band intensity, also exist (see region bracketed in FIG. 28). These, as yet uncharacterised, variants do not affect the ability to score allele codes or diploid codes from total genomic DNA (see below).

Allelic variability in MS21A allele codes: The 34 alleles so far typed all have different MVR maps. To identify related alleles, which share regions of map similarity, all possible pairwise comparisons of allele codes were made by dot matrix analysis (FIG. 29). Only three significantly related alleles were found (FIG. 30). These show most inter-allelic variability in repeat copy number and interspersion pattern at the extreme 5' ends of the tandem repeat array, and are almost identical along the rest of their length which extends to the end of the mapped region. All three alleles are of similar overall length (around 100 repeat units) as determined by Southern blot hybridisation of total genomic DNA (data not shown).

MVR-PCR on total genomic DNA: MS31A MVR-PCR can be applied to genomic DNA to reveal the digital code derived from both alleles superimposed, in the same way as at MS32 FIG. 31). The extreme allelic variability and better mixed interspersion pattern of variant repeat units makes it likely that MS31 diploid codes will be even more diverse than those seen at MS32. Furthermore, combinations of primers can be used to generate diploid codes from MS31 and MS32 alleles simultaneously. This "duplex MVR-PCR" has been tested using MVR-PCR primers 32-Tag-C, 32-Tag-T and 31-Tag-A, 3 1-Tag-G, along with the appropriate flanking primers and Tag, using the same PCR conditions as employed for each locus separately. 31-Tag-A and 32-Tag-C were used in one PCR reaction with 3l-Tag-G and 32-Tag-T in the other, to maintain the conventional order of a-type and t-type repeat unit lanes on MVR-PCR gels. Southern blot analysis by sequential hybridisation with MS31, followed by MS32, showed complete sets of PCR products from each locus with no evidence of inter-locus interference of cross-hybridisation (FIG. 31), indicating that repeat units from both loci amplify independently.

The MS31A codes are generally the more informative; for example the MS31A and MS32 profiles of individual 9 whose MS32 code is largely dominated by repeat unit positions homozygous for a-type repeats.

Flanking polymorphisms and "knockout" MVR-PCR: If polymorphisms can be found in the DNA flanking the 5' end of MS31 alles, allele-specific flanking primers can be designed to allow the selective mapping of single alleles from the total genomic DNA of individuals heterozygous for these polymorphisms, without the need for allele separation prior to mapping (allele "knockout").

Figure 1:
FIGS. 1A–1C shows the principles of minisatellite repeat coding. A, minisatellite alleles consisting of interspersed arrays of two variant repeat units termed a-type (shaded boxes) and t-type (open boxes). Individual alleles can be encoded as a binary string extending from the first repeat units. In total genomic DNA, a corresponding ternary code of both alleles superimposed can be generated. At each repeat unit position, the alleles can be both a-type (code 1), both t-type (code 2), or heterozygous with one a-type and cone t-type repeat (code 3). B, the consensus repeat unit sequence of human minisatellit MS32 (D1S8) showing the polymorphic site which generates HaeIII cleavable (a-type) repeats and HaeIII-resistant (t-type) repeat. 32-TAG-A and 32-TAG-T are variant repat specific oligonucleotides terminating at this polymorphic site. Each primer consists of 20 nt minisatellite repeat sequence (bold) preceded by a 20 nt 5' synthetic non-minisatellite extension identical to the TAG amplimer. C, the principle of MVR-PCR, illustrated for a single allele amplified using primer 32-TAG-A. 1. At low concentration of primer, 32-TAG-A will anneal to approximately one a-type repeat unit per target minisatellite molecule and extend into the flanking DNA. 2. Amplimer 32D primes from the flanking DNA, creating a sequence complementary to TAG. 3. These DNA fragments terminating in 32D and the TAG complement can now be amplified using high concentration of 32D and TAG amplimers, to create a set of PCR products extending from the flanking 32D site to each a-type repeat unit. Use of primer 32-TAG-T at stage 1 will create a complementary set of products terminating at each t-type repeat unit.

Southern blot analysis of genomic DNA from several individuals revealed the presence of a polymorphic AluI site 400 bp inside the Sau3AI fragment spanning MS31 (data not shown). The sequence of cloned MS31A 5' flanking DNA reveals a candidate cryptic AluI site 398 bp from 5' Sau3AI site and 2 bp from the first repeat unit (FIG. 27). To determine whether variation at this site was responsible for the polymorphism, DNA was tested from three individuals characterised by Southern blot analysis as AluI+/+ and AluI−/− homozygotes and an AluI+/− heterozygote. Single allele codes of both alleles in all of these individuals were available. 1 µg of these DNAs were digested with 10 units of AluI and 10 ng digest DNA was amplified in an MVR-PCR reaction using the flanking primr 310R which binds just 5' to the suspected AluI site (FIG. 1). The results confirmed that this is the location of the polymorphism: the AluI−/− homozygote gave a normal diploid code, the Alu+/+ homozygote yielded no MVR-PCR products and the AluI+/− heterozygote produced a single allele code identical to that previously determined for one of his alleles (data not shown).

A PCR assay for the AluI polymorphism was developed, based on the ability to generate diagnostic DNA fragments by AluI digestion of PCR products containing the site. The flanking region extending into the minisatellite array was amplified from total genomic DNA using 31-Tag-A at high concentration plus flanking primer 31A. Because of the primer concentrations and short extension time employed, only PCR products extending to the first few repeat units were amplified to levels detectable by staining with ethidium bromide, with the fragment corresponding to amplification from the first repeat unit predominating. Cleavage of an AluI+allelic PCR product with AluI will generate a 95 bp DNA fragment extending from the 31 A primer site to the AluI site. AluI− alleles will not be cleaved, and heterzygoes will show both cleaved and intact PCR products. Examples of this assay are shown in FIG. 32. Analysis of 78 unrelated Caucasians and 82 unrelated Japanese showed that the AluI polymorphism is common in both populations (0.15, 0.26 frequency of the AluI$^+$ allele respectively).

To determine the molecular basis of the AluI polymorphism, 30 cycle MVR-PCR was conducted on AluI+/+ and AluI-/- individuals. PCR products were resolved by agarose gel electrophoresis and visualised by staining with ethidium bromide. The lower band from each ladder was electroeluted, reamplified using 31A and Tag primer and directly sequenced (Winship, NAR, 1989, 17, 1266). The polymorphic AluI site was revealed as AGCT in the AluI+ allele and GGCT in the AluI- form; the A/G transition is located 4 bp upstream of the first minisatellite repeat (FIG. 27).

A pair of flanking primers, differing in only an 'A' (31 AluI$^+$) or 'G' (31 Alu 1-) at their 3' ends which corresponds to the variable base, were designed for "knockout" MVR-PCR (see legend to FIG. 27 for sequences). When used in MVR-PCR reactions at an appropriate annealing temperature (68° C.) these primers discriminate between the two alleles in AluI+/-heterozygotes allowing selective mapping of one or other MS31A allele from total genomic DNA (data not shown).

The successful development of MS31A MVR-PCR provides a powerful adjunct to MS32 digital coding, particularly since both loci can now be typed simultaneously, which substantially increases the speed with which reference diploid databases can be constructed. As further minisatellites amenable to MVR-PCR are discovered, multiplex MVR-PCR may become possible as long as no cross-priming of repeat units occurs and PCR parameters are similar for all loci involved.

Duplex, and ultimately multiplex, MVR-PCR will also be important for distinguishing close relatives, in particular siblings who have 1/4 change of sharing the same parental alleles and therefore diploid codes at a given locus. In paternity cases, where it is possible that a paternal exlusion at one locus could be due either to a new mutation in one of the minisatellite alleles, or to non-paternity, typing at additional loci will almost certainly distinguish between these possibilities. It will also improve the typing of degraded DNA by increasing the amount of information recoverable from the limited number of repeat units which can be scored in the coding ladder of such samples.

Single allele coding provides basic information on MS31A variability. MS31A allele coding can now be carried out by analysis of physically separated alleles, or much more easily by allele knockout on AluI+/- heterozygotes. Sequence analysis of the MS31 flanking region is currently under way to search for more sites of variation and thereby increase the range of individuals to whom knockout MVR-PCR can be applied. Knockout MVR-PCR has potential forensic applications, for examples by selectively ablating the victim's alleles in victim/assailant DNA mixtures.

Unfortunately the deduction of single allele codes from the ternary codes generated by MVR-PCR of genomic DNA in familes, which was so useful in constructing a database of single MS32 alleles, is not straightforward at MS31A. At MS31A the existence of O-type repeats combined with the presence of variant repeats which affect band intensity make it impossible to use band intensity (dosage) to distinguish for example, a/O repeat positions in genomic DNA from homozygous a/a positions. Such incorrect genotyping can lead to apparent parental exclusions or incorrect allele codes; this not only interferes with the deduction of haplotypes from pedigree data, but would also create problems in paternity testing by MVR-PCR. It might be possible to solve this problem by sequence characterisation of these additional variant repeats and the use of additional MVR-PCR primers corresponding to O-type repeat units. In the meantime, an alternative is to use allele knockout MVR-PCR in those families where parents are AluI$^+$ and AluI- homozygotes respectively or where one or both parents are AluI+/- heterozygotes. In appropriate families, single allele codes of all four parental alleles can be determined in this way.

Most MS3 1A alleles are long (>100 repeat units) and thus individual heterozygosity for short alleles will be rare; such heterozygotes can be identified by reaction of the diploid coding ladder to hemizygosity beyond the end of the shorter allele, with loss of heterozygous a/t repeat positions. However, distinguishing hemizygosity from homozygosity over such coding regions requires interpretation of band intensity (dosage) which can be problematical at MS31A. Correct heterozygous null scoring is irrelevant for individual identification and the presence of reproducable band intensity fluctuations at MS31 may even enhance this application, but is important in paternity analysis. Southern blot analysis of 80 unrelated Caucasians has shown that the shortest MS31A alleles still contain around 90 repeat units. Only one allele shorter than this has ever been found. This allele was too small to be detected by Southern blot analysis of genomic DNA (a "null" allele; Armour et al., 1992) but was revealed by PCR amplification to be approximately 25 repeat unts in length.

Preliminary surveys to allelic variability at MS31A have revealed extraordinary levels of MVR code variation, to the extent that most alleles are devoid even of regions of significant MVR code similarity. Interestingly, the only three alleles that are related (FIG. 30) show most MVR haplotype differences restricted to the extreme beginning of the tandem repeat array. This is analogous to the gradient of variability along minisatellite alleles seen at MS32 and MS205 (unpublished data), which has been shown to arise from a mutation hotspot localised to the beginning of the tandem repeat array at which most spontaneous mutational change in repeat copy number and therefore the MVR map occur.

TABLE 8

|  | a-type | t-type | O-type | Total |
| --- | --- | --- | --- | --- |
| Number of repeats | 1279 | 962 | 43 | 2284 |
| Proportion of repeat unit types (%) | 56 | 42 | 2 | 100 |

EXAMPLE 19

In the PCR, template independent reactions can take place, leading to the formation of "primer dimers". Because primers are present at high concentrations, weak interactions between them can and do occur. When these interactions are at the 3'-ends of the primers, they can be extended by Taq polymerase and are good substrates for amplification in subsequent cycles. This leads to the production of large quantities of small, efficiently amplified products and this reduces the efficiency of amplification for "true" targets. The formation of primer dimers is dependent upon some degree of homology between primers and their high concentrations. Two different primers or two identical primers can participate in this reaction and it is possible to reduce the formation of dimers by careful primer design.

In the production of large multiplex reactions containing many primers at high concentration, it becomes impossible to prevent altogether the formation of primer dimers. Reducing the concentrations of the individual primers can help, but eventually has an impact on the amplification efficiency.

In many multiplex reactions, only a few of the amplicons are expected to amplify in any one tube and furthermore there is a physical limit to the total volume of primers it is possible to add to a reaction. We have sought to overcome these problems using primers which are genome specific at the 3'-ends but which carry common extensions (Tails) at their 5'-ends. In addition, the reactions include tail specific primers (Tags) which can prime from these common Tails. Low concentrations of specific primers can be used in combination with higher concentrations of Tag to produce a wide range of specificities without introducing enormous quantities of primer.

In order to allow "switching" from genomic priming (with the specific portions of the primers) to Tag priming, the Tm of the Tag is made larger than that of the genomic priming segment. After a few (minimum 2) rounds of genomic priming, the temperature can be shifted up and the subsequent amplification is driven entirely by the Tag primers. The combination of low primer concentrations and limited priming from the 3'-ends of the Tailed primers reduces the probability of primer dimer formation.

The Tag sequences must have a number of characteristics. They must have no genomic target themselves, they must have relatively high Tms, they must not be prone to primer dimer formation with other primers in the reactions (especially themselves and other Tags) and they must have no stable internal secondary structure. A range of 13-mers were rationally designed: using published human genomic sequences, the least frequent neighbouring pairs of bases were determined and incorporated into the sequences. The resulting oligonucleotides were combined to generate 26-mers and examined for internal self complementarity, tendency towards primer dimer formation and possible genomic targets on the databases. The most promising of these were synthesised and functionally tested to ensure the absence of genomic amplification and primer dimer formation.

We exemplify two possible formats: identical Tails on each primer of a pair plus a single matching Tag primer (HomoTags); or different Tails on each primer plus two matching Tags (HeteroTags). An anticipated advantage of the HomoTag format was that short products (especially primer dimers) would be prone to annealing between the two complementary ends of a single strand, because of the high local concentration of such sequences when the products are small. This might prevent efficient binding of the Tag primer and interfere with the amplification of primer dimers and other small amplicons. HANDS may therefore prevent the formation of primer dimers and allow the efficient design of large multiplexes.

MATERIALS AND METHODS

Primers

All primers used in the subsequent experiments were synthesised by Oswel DNA Services Ltd., Southampton.

TABLE 1

Primer Sequences

| MUTATION OR TARGET | PRIMER | CODE | SEQUENCE 5' – 3' |
|---|---|---|---|
| — | N4198 | TAG ⅗ | GACGATACGACGGGCGTACTAGCGTA |
| G542X | N4199 | GX-C ⅗ | GACGATACGACGGGCGTACTAGCGTAAAAA TTTCAGCAATGTTGTTTTTGACCAAC |
| G542X | N4200 | GX-M ⅗ | GACGATACGACGGGCGTACTAGCGTACACTC AGTGTGATTCCACCTTCTCA |
| — | N4201 | TAG 5/2b | GCGTACTAGCGTACCACGTGTCGACT |
| G542X | N4202 | GX-C 5/2b | GCGTACTAGCGTACCACGTGTCGACTAAAAT TTCAGCAATGTTGTTTTTGACCAAC |
| G542X | N4203 | GX-M 5/2b | GCGTACTAGCGTACCACGTGTCGACTCACTC AGTGTGATTCCACCTTCTCA |
| DF508 | P2250 | IF + C3 5/2b | GCGTACTAGCGTACCACGTGTCGACTCACTA ATGAGTGAACAAAATTCTCACCATT |
| DF508 | P1292 | IF + b5 + M 5/2b | GCGTACTAGCGTACCACGTGTCGACTGCCTG GCACCATTAAAGAAAATATCATTGG |
| Exon 10 | P4649 | IF + C3PD | GCGTACTAGCGTACCACGTGTCGACTCGTGA TTTGATAATGACCTAATAATGATGG |
| Exon 10 | P4650 | IF + b5 + M PD | GCGTACTAGCGTACCACGTGTCGACTCTCAC TAATGAGTGAACAAAATTCTCACCA |
| G542X | P4205 | GX-C 10/2b | AGGATCGGTATCGCCACGTGTCGACTAAAAT TTCAGCAATGTTGTTTTTGACCAAC |
| Exon 11 | P6120 | PDHET4 5/2b | GCGTACTAGCGTACCACGTGTCGACTTCACC TTGCTAAAGAAATTCTTGCTCGTTG |
| — | N4204 | TAG 10/2b | AGGATCGGTATCGCCACGTGTCGACT |
| Apo lipoprotein B | P5574 | Apo B Reverse | CAGCCAAAACTTTTACAGGGATGGAGAACG |
| Apo lipoprotein B | P5575 | Apo B Forward | CTCTGGGAGCACAGTACGAAAAACCACCT |

Preparation of Genomic DNA

Human genomic DNA samples were prepared by one of three methods:

a) standard extraction from blood cells using the method of Kunkel L. M., Smith K. D., and Boyer S. H., 1977, Proc. Natl. Acad. Sci. USA, 74, 1245–49 b) rapid extraction from peripheral blood cells. Each 200 ml aliquot of previously frozen blood was diluted with 800 ml of freshly made 170 mM NH$_4$Cl solution. After agitating gently for 20 minutes, the white cells were collected by centrifugation in a microfuge for 2 mins. The white cell pellet was washed four times with 300 ml of 10 mM NaCl/10 mM EDTA, the cells being collected by centrifugation for 15 sec between washes. After washing, the white cell pellet was resuspended in 500 ml of 50 mM NaOH and vortexed for 15 sec. The cell suspension was placed in a boiling water bath for 20 min and neutralised at room temperature by the addition of 100 ml of 1M Tris-HCl (pH7.5). After vortexing briefly the remaining cellular debris was pelleted in a microfuge for 10 sec. 5 ml of DNA prepared in this way was used in the reactions as described.

c) rapid extraction from buccal epithelial cells. Buccal epithelial cells were collected from donors using either the mouthwash or buccal swab methods. When the mouthwash method was used, donors provided cells in 10 ml of 4% sucrose after agitating in their mouths for a minimum of 20 seconds. After centrifugation at 200 rpm for 10 min., the supernatant was discarded and the cells resuspended in 500 ml of 10 mM NaCl/10 mM EDTA and transferred to screw-topped microfuge tubes. The cells were again pelleted in a niicrofuge for 15 sec and resuspended in 500 ml of 50 mM NaOH as above. The remainder of the procedure was then exactly as has been described for blood cells in section b). For buccal swabs, cotton buds were saturated with 4% sucrose. The donor's cheek was swabbed briefly (5 sec) and the head of the cotton bud added to 500 ml of 170 mM $NH_4Cl$ in a screw-topped microfuge tube. After vortexing for 15 sec. the bud was removed from the tube and the epithelial cells collected by microfugation for 15 sec. After removal of the supernatant, the cells were washed with 300 ml of 10 mM NaCl/10 mM EDTA and collected by microfuging for 15 sec. The cells were resuspended in 500 ml of 50 mM NaOH and the remainder of the procedure detailed for blood in section b) was followed.

PCR and ARMS Reaction Conditions

For ARMS reactions, standard conditions were 1 x ARMS buffer (50 mM KCl, 10 mM Tris-HCl pH 8.3, 1.2 mM $MgCl_2$, 0.1% gelatin,), 100 mM dATP, dCTP, dGTP, dTTP and the appropriate individual primers at concentrations defined in the following protocols. 40 ml aliquots of the appropriate reaction mixes were used in 0.65 ml polypropylene tubes. 5 ml (~20 ng) of human genomic DNA was used per reaction. 2 units of Taq polymerase prepared in 5 ml of 1 x ARMS buffer was used in each individual reaction. Each reaction was overlaid with one drop of light white mineral oil (Sigma Chemicals Ltd.) The amplification procedure was performed on a Perkin Elmer 480 Thermal Cycler. Amplification cycles vary with each protocol and are described in each case.

Detection

Analysis of polymerase chain reaction (PCR) products was by gel electrophoresis through a 12.8×16.2 cm, 3% Nusieve agarose gel (w/v) prepared with 1 x TBE buffer (Tris 134 mM, Boric acid 74.9 mM, EDTA 2.55 mM), 0.5 mg ml$^{-1}$ ethidium bromide. 20 ml of PCR product was added to 10 ml of gel loading buffer (30% glycerol, 0.1 % bromophenol blue in 1 X TBE buffer ), and 15 ml loaded onto the gel. The products were electrophoresed under 1 x TBE, 0.5 mg ml$^{-1}$ ethidium bromide at 120 volts for time as stated in the following experiments. Gels were visualised under ultra-violet light.

1. HOMOTAGS VERSUS HETEROTAGS IN A TAGS AND TAILS CYSTIC FIBROSIS SINGLE MUTATION TEST

Aims

Two formats were compared to assess which gave the higher detectability of target DNA.

Format one—HomoTags—had a homologous 540 tail sequence (52b) on the mutant primer and common primer.

Format two—HeteroTags—had heterogenous 5' tails, tail 5/2b on one primer and tail 3/5 on the other. This format was tried in all combinations i.e. 3/5 tail on mutant primer and tail 5/2b on common primer and vice versa.

METHOD

Reagents Used.

10 x ARMS buffer.

Sigma Water Tissue Culture Grade 1 mM dNTPs

Primers.

Sequences in Table 9.

Tag 5/2b

G542X common 5/2b 5' tail=GX-C 5/2b

G542X mutant 5/2b 5'tail=GX-M 5/2b

Tag 3/5

G542X common 3/5 5' tail=GX-C 3/5

G 542X mutant 3/5 5'tail=GX-M 3/5

Non-tailed Apo B controls=Apo B For. & Apo B Rev.

Preparation of Mixes

All mixes contained 100 mM dNTPs, 0.1 mM Apo B controls and were prepared in 1 x ARMS buffer to a final reaction volume of 50 ml. Primers and their respective concentrations are given in Table 10.

Preparation of Samples

Mixes were aliquoted in 40 ml volumes and dispensed into 0.65 ml Eppendorf tubes numbered as described in table 3.

5 ml of the appropriate DNA was added, tubes were spun in a microfuge to ensure DNA was in the mix and overlaid with a drop of light white mineral oil.

| DNA: | | | |
|---|---|---|---|
| Gx = G542X/DF508 | Sample DV3 | 1/100 dilution | DNA extraction method a) |
| + = +/+ method c) | Sample Alk 16 | 1/20 dilution | DNA extraction |

TABLE 2

Primer concentrations in HomoTag & HeteroTag Mixes.

| MIX CODE | TAG PRIMER/S | TAILED PRIMER 1 | TAILED PRIMER 2 |
|---|---|---|---|
| 1A | 1 mM Tag 5/2b | 1 mM GX-C 5/2b | 1 mM GX-M 5/2b |
| 1B | 1 mM Tag 5/2b | 0.1 mM GX-C 5/2b | 0.1 mM GX-M 5/2b |
| 1C | 1 mM Tag 5/2b | 0.01 mM GX-C 5/2b | 0.01 mM GX-M 5/2b |
| 1D | 1 mM Tag 5/2b | 0.02 mM GX-C 5/2b | 0.02 mM GX-M 5/2b |
| 2A | 1 mM Tag 5/2b + 1 mM Tag 3/5 | 1 mM GX-C 5/2b | 1 mM GX-M 3/5 |
| 2B | 1 mM Tag 5/2b + 1 mM Tag 3/5 | 0.1 mM GX-C 5/2b | 0.1 mM GX-M 3/5 |
| 2C | 1 mM Tag 5/2b + 1 mM Tag 3/5 | 0.01 mM GX-C 5/2b | 0.01 mM GX-M 3/5 |
| 2D | 1 mM Tag 5/2b + 1 mM Tag 3/5 | 0.02 mM GX-C 5/2b | 0.02 mM GX-M 3/5 |
| 3A | 0.5 mM Tag 5/2b + 0.5 mM Tag 3/5 | 1 mM GX-C 5/2b | 1 mM GX-M 3/5 |
| 3B | 0.5 mM Tag 5/2b + 0.5 mM Tag 3/5 | 0.1 mM GX-C 5/2b | 0.1 mM GX-M 3/5 |
| 3C | 0.5 mM Tag 5/2b + 0.5 mM Tag 3/5 | 0.01 mM GX-C 5/2b | 0.01 mM GX-M 3/5 |
| 3D | 0.5 mM Tag 5/2b + 0.5 mM Tag 3/5 | 0.02 mM GX-C 5/2b | 0.02 mM GX-M 3/5 |
| 4A | 1 mM Tag 5/2b + 1 mM Tag 3/5 | 1 mM GX-C 3/5 | 1 mM GX-M 5/2b |
| 4B | 1 mM Tag 5/2b + 1 mM Tag 3/5 | 0.1 mM GX-C 3/5 | 0.1 mM GX-M 5/2b |
| 4C | 1 mM Tag 5/2b + 1 mM Tag 3/5 | 0.01 mM GX-C 3/5 | 0.01 mM GX-M 5/2b |
| 4D | 1 mM Tag 5/2b + 1 mM Tag 3/5 | 0.02 mM GX-C 3/5 | 0.02 mM GX-M |
| 5A | 0.5 mM Tag 5/2b + 0.5 mM Tag 3/5 | 1 mM GX-C 3/5 | 1 mM GX-M 5/2b |
| 5B | 0.5 mM Tag 5/2b + 0.5 mM Tag 3/5 | 0.1 mM GX-C 3/5 | 0.1 mM GX-M 5/2b |
| 5C | 0.5 mM Tag 5/2b + 0.5 mM Tag 3/5 | 0.01 mM GX-C 3/5 | 0.01 mM GX-M 5/2b |
| 5D | 0.5 mM Tag 5/2b + 0.5 mM Tag 3/5 | 0.02 mM GX-C 3/5 | 0.02 mM GX-M 5/2b |

TABLE 11

Composition of Specific Mixes

| TUBE | MIX | DNA | TUBE | MIX | DNA | TUBE | MIX | DNA |
|---|---|---|---|---|---|---|---|---|
| 1 | 1A | Gx | 16 | 2C | Gx | 31 | 4B | Gx |
| 2 | 1A | + | 17 | 2D | + | 32 | 4B | + |
| 3 | 1A | -ve | 18 | 2D | -ve | 33 | 4C | Gx |
| 4 | 1B | Gx | 19 | 3A | Gx | 34 | 4C | + |
| 5 | 1B | + | 20 | 3A | + | 35 | 4D | Gx |
| 6 | 1C | Gx | 21 | 3A | Gx | 36 | 4D | + |
| 7 | 1C | + | 22 | 3B | -ve | 37 | 5A | Gx |
| 8 | 1D | Gx | 23 | 3B | + | 38 | 5A | + |
| 9 | 1D | + | 24 | 3C | Gx | 39 | 5A | -ve |
| 10 | 2A | Gx | 25 | 3C | + | 40 | 5B | Gx |
| 11 | 2A | + | 26 | 3D | Gx | 41 | 5B | + |
| 12 | 2A | -ve | 27 | 3D | + | 42 | 5C | Gx |
| 13 | 2B | Gx | 28 | 4A | Gx | 43 | 5C | + |
| 14 | 2B | + | 29 | 4A | + | 44 | 5D | Gx |
| 15 | 2C | Gx | 30 | 4A | -ve | 45 | 5D | + |

Amplification

Tubes were cycled on a Perkin Elmer 480 Thermal Cycler. All samples were soaked at 94° C. for 5 minutes before adding 2 units 5 ml$^{-1}$ Kodak Taq Polymerase in 1x ARMS buffer.

Amplification cycles were as follows:

4 cycles of (94° C.—1', 62° C.—10', 72° C.—1')
31 cycles of (94° C.—1', 62° C.—1', 72° C.—1')
1 cycle of (72° C.—10')

Detection 20 ml of PCR product was added to 10 ml of gel loading buffer. 15 ml of each sample was loaded onto gels (3% Nusieve agarose) and electrophoresed at 120 Volts for 90 minutes.

Results

Results are shown in FIG. 34.

Conclusions

The yield of control ARMS product was lower in the HeteroTag format (Panels 2–5) compared to the HomoTag format (Panel 1). This was likely to be due to the preferential amplification of primer-dimers, which were easily visualised on the gel. The HomoTag format proved the more favourable system. There was very little evidence of primer dimers with the lower concentrations of primers, and a strong diagnostic band was produced when only 0.01 mM of specific tailed primers were present in the mix.

2. G542X TAGS AND TAILS: DETERMINING THE CONCENTRATION OF TAILED PRIMER AT WHICH PRIMER-DIMER FORMATION CEASES

Aims

The previous experiment indicated that a HomoTag format effectively prevented primer-dimer amplification. HeteroTags however, did not. The aim of the experiment was to determine, for a HeteroTag format, a) how low the tailed primer concentration needed to be for the disappearance of primer-dimers, and b) at which primer concentration specific product was no longer detectable.

METHOD

Reagents Used.
10 x ARMS buffer
Sigma water—Tissue Culture Grade
1 mM dNTPs
Kodak Taq Polymerase
Primers
Sequences in Table 9.
Tag 5/2b —
Tag 3/5
G542X common 5/2b 5' tail =GX-C 5/2b
G542X mutant 5/2b 5' tail =GX-M 5/2b
G542X common 3/5 5' tail =GX-C 3/5
G542X mutant 3/5 5' tail =GX-M 3/5

Preparation of Mixes

All mixes contained 100 mM dNTPs and were prepared in 1x ARMS buffer to a final reaction volume of 50 ml. Primers and their respective concentrations are given in Table 4 for HomoTag format mixes, and Table 5 for the HeteroTag format mixes.

TABLE 12

Primers and concentrations in HomoTag format mixes.

| MIX CODE | GX-M 3/5 mM | GX-C 3/5 mM | TAG 3/5 mM | TAG 5/2b mM |
|---|---|---|---|---|
| M | 1 | 1 | 1 | — |
| N | 0.1 | 0.1 | 1 | — |
| O | 0.01 | 0.01 | 1 | — |
| P | 0.005 | 0.005 | 1 | — |
| Q | 0.001 | 0.001 | 1 | — |
| R | 0.0005 | 0.0005 | 1 | — |
| S | 0.0001 | 0.0001 | 1 | — |

TABLE 13

Primers and concentrations in HeteroTag format mixes.

| MIX CODE | GX-M 3/5 mM | GX-C mM | TAG 3/5 mM | TAG 5/2b mM |
|---|---|---|---|---|
| T | 1 | 1 | 0.5 | 0.5 |
| U | 0.1 | 0.1 | 0.5 | 0.5 |
| V | 0.01 | 0.01 | 0.5 | 0.5 |
| W | 0.005 | 0.005 | 0.5 | 0.5 |
| X | 0.001 | 0.001 | 0.5 | 0.5 |
| Y | 0.0005 | 0.0005 | 0.5 | 0.5 |
| Z | 0.0001 | 0.0001 | 0.5 | 0.5 |

Preparation of Samples

Each mix, as listed above, was aliquoted into 3×40 ml volumes. To each first tube, 5 ml of mutant DNA [Sample DV3—1/100 dilution—G542X/DF508 —DNA extraction method a)] was added. To each second tube, 5 ml of normal DNA [Sample Alk 16—1/20 dilution—+/+—DNA extraction method c)] was added. To each third tube, 5 ml of Sigma water was added [negative control]. All tubes were microfuged and overlaid with light white mineral oil.

Amplfication

Tubes were cycled on a Perkin Elmer 480 Thermal Cycler.

All tubes were soaked at 94° C. for 5 minutes before adding 2 units/5 ml Kodak Taq Polymerase in 1 x ARMS buffer.

Amplification cycles were as follows:
4 cycles of (94° C.—1', 62° C.—10', 72° C.—1')
35 cycles of (94° C.—1',62° C.—1', 72° C.—1')
1 cycle of (72° C.—10')

Detection 20 ml of PCR product was added to 10 ml of gel loading buffer. 15 ml of each sample was loaded onto gels (3% Nusieve agarose) and electrophoresed at 120 Volts for 90 minutes.

Results

Results are shown in FIGS. 35 and 36.

Conclusions

The HomoTag format, as expected, inhibited primer-dimer amplification and as sensitivity is not compromised, a specific diagnostic band was seen when only 0.005 mM of specific tailed primers were used. The HeteroTag format, permitted primer-dimer amplification and these are visible on the gel when only 0.0001 mM (0.1 nM) of specific tailed primers were present. The most likely cause of the strong 60 mer primer dimer was a reaction between a tailed primer and a tag sequence.

In conclusion, the results of this experiment demonstrate the extent of problems which would be encountered should primer-dimers form and subsequently amplify in a tag and tail system. An effective inhibition of primer dimers is needed in order for a large multiplex reaction to be viable. Using a HomoTag system may be the solution to this.

3. DETERMINING THE INHIBITORY EFFECT OF HOMOLOGOUS 5' TAILS (HOMOTAGS) ON PRIMER-DIMER AMPLIFICATION IN A SINGLE MUTATION TEST

Aims

HomoTags have been shown to inhibit primer-dimer amplification in previous experiments. The aim of this experiment was to determine if HomoTags are efficient enough to prevent primer dimer amplification when primer-dimers are specifically designed into the test format.

The single mutation test for the DF508 is a well established reaction and has been used in a tags and tails format. To test the HomoTag hypothesis two new primers were designed with deliberate overlapping 3' ends, using exon 10 of the cystic fibrosis regulator gene as the specific target. Both were synthesized with the 5/2b 5' tail sequence.

Primer IF-C3PD, has a 3', 3 base long complementary sequence to the 3' end of the DF508 common primer, IF-C3 5/2b. When used as a pair, in the presence of DNA in a PCR reaction a 422 base pair product would be generated.

Primer IF-b5-MPD, has a 3', 4 base long complementary sequence to the 3' end of the DF508 mutant primer, IF-b5-M 5/2b. Product generated by this primer pair in a PCR reaction should be 566 base pairs long.

Mixes containing decreasing concentrations of these primer pairs, and their respective Tag primer, were prepared and genomic DNA added. Following PCR cycling it was expected that the 5' homologous tails would prevent amplification of the inevitable primer-dimers, and that product amplification would be the favoured reaction.

METHOD

Reagents Used.
10 x ARMS buffer
Sigma water—Tissue Culture Grade.
1 mM dNTPs
Kodak Taq Polymerase
Primers
Sequences in Table 9.
DF508 common 5/2b 5' tail=IF-C3 5/2b Primer-dimer partner 1, 5/2b 5' tail=IF-C3PD 5/2b
DF508 mutant 5/2b 5' tail=IF-b5-M 5/2b
Primer-dimer partner 2, 5/2b 5' tail=IF -b5-MPD 5/2b
Tag 5/2b Preparation of Mixes All mixes contained 100 mM dNTPs and were prepared in 1 x ARMS buffer to a final reaction volume of 50 ml. Primers and their respective concentrations are given in tables 14 and 15.

TABLE 14

Primers and concentrations for Primer-Dimer 1 reactions.

| MIX CODE | IF-C3 5/2b mM | IF-C3PD 5/2b mM | TAG 5/2b mM |
|---|---|---|---|
| A | 1 | 1 | — |
| B | 1 | 1 | 1 |
| C | 0.1 | 0.1 | — |
| D | 0.1 | 0.1 | 1 |
| E | 0.01 | 0.01 | 1 |

TABLE 15

Primers and concentrations for Primer-Dimer 2 reactions.

| MIX CODE | IF-b5-M 5/2b mM | IF-b5-MPD 5/2b mM | TAG 5/2b mM |
|---|---|---|---|
| F | 1 | 1 | — |
| G | 1 | 1 | 1 |
| H | 0.1 | 0.1 | — |
| I | 0.1 | 0.1 | 1 |
| J | 0.01 | 0.01 | 1 |

Preparation of Samples

All reaction mixes were aliquoted in 40 ml volumes and dispensed into 0.65 ml Eppendorf tubes numbered as described in table 8.

Added 5 ml of the appropriate DNA:

| + | Alk 16 | +/+ | 1/20 dilution | DNA extraction method c). |
| DF | DV3 | DF508/G542X | 1/100 dilution | DNA extraction method a) |
| -ve | Sigma water | | negative control. | |

TABLE 16

| TUBE | MIX | DNA | TUBE | MIX | DNA | TUBE | MIX | DNA |
|---|---|---|---|---|---|---|---|---|
| 1 | A | -ve# | 13 | D | + | 25 | G | DF |
| 2 | A | -ve# | 14 | D | + | 26 | G | DF |
| 3 | A | -ve no Taq* | 15 | D | -ve | 27 | G | -ve |
| 4 | A | + | 16 | E | + | 28 | H | DF |
| 5 | A | + | 17 | E | + | 29 | H | DF |
| 6 | A | -ve | 18 | E | -ve | 30 | H | -ve |
| 7 | B | + | 19 | F | -ve# | 31 | I | DF |
| 8 | B | + | 20 | F | -ve# | 32 | I | DF |
| 9 | B | -ve | 21 | F | -ve no Taq* | 33 | I | -ve |
| 10 | C | + | 22 | F | DF | 34 | J | DF |
| 11 | C | + | 23 | F | DF | 35 | J | DF |
| 12 | C | -ve | 24 | F | -ve | 36 | J | -ve |

*No primer-dimer control
To demonstrate that the primer pairs produced primer-dimers Amplification Tubes were cycled on a Perkin Elmer 480 Thermal Cycler. All tubes were soaked at 94° C. for 5 minutes before adding 2 units 5 ml$^{-1}$ Taq polymerase in 1 x ARMS buffer, with the exception of tubes 3 and 21 to which 5 ml of Sigma water was added.

Amplification cycles were as follows:

4 cycles of (94° C.—1', 60° C.—10', 72° C.—1')

35 cycles of (94° C.—1', 60° C.—1', 72° C.—1')

1 cycle of (72° C.—10')

Detection 20 ml of PCR product was added to 10 ml of gel loading buffer. 15 ml of each sample was loaded onto gels (3% Nusieve agarose) and electrophoresed at 120 Volts for 90 minutes.

Results

Results are shown in FIG. 37.

Conclusions

In the absence of DNA or Tag primer, the two pairs of primers at 1 mM efficiently produced the expected primer dimers. Even in the presence of DNA the primer dimer was amplified in large quantities at this concentration.

When the Tag primer was added to the same mix, the pattern of primer-dimers changed due to interactions between the tag and tailed primers.

At lower primer concentrations (0.1 mM and 0.01 mM) primer-dimers were eradicated. To determine if HomoTags provided a true inhibition of primer-dimer amplification, and that the effect is not due solely to non-formation of primer-dimers when very low primer concentrations are used, further analyses were carried out.

It is hypothesised that self-annealing of the primer-dimer strand prevents any subsequent amplification by tag, liberating PCR reagents to amplify the desired amplicon.

4. VERIFICATION OF THE HOMOTAG INHIBITORY EFFECT

Aims

It has been demonstrated that primer-dimer amplification is not observed in a HomoTag test format when the concentration of tailed primers is low, and has been hypothesised that this is due to intra-molecular annealing of the complementary 3' and 5' ends of the primer-dimer.

The aim of this experiment was to verify that the effect seen is due to the suggested self-annealing event, and not to non-formation of primer-dimers when tailed primers were only present at very low concentrations in the mix.

The experiment was divided into two parts.

i) Preparation of 3 different primer-dimers by PCR, analysis by gel electrophoresis, extraction and purification, and finally quantification. One pair of deliberate primer-dimer forming primers had homologous 5' tails (HomoTags) and the other two pairs of deliberate primer-dimer forming primers had different 5' tail sequences (HeteroTags).

ii) Secondary amplification of a known quantity of primer-dimer by the respective tag primer or primers, and analysis by gel electrophoresis to assess any inhibitory effects.

4i) PREPARATION OF TAILED PRIMER-DIMERS

Aim

In order to produce large quantities of HomoTagged and HeteroTagged primer-dimers, primer sequences were designed with deliberate complementarity between 3' ends.

Primer dimer 1 was formed between primers IF+C3PD 5/2b and IF+C3 5/2b, which had 3 base-long complementary sequences at their 3' ends. Both of the primers had 5' tail sequence 5/2b thus the resulting primer-dimer was termed "HomoTagged".

Primer dimer 2 was formed between primers GX-C 3/5 and PDHBT4 5/2b, which had 4 base-long complementary sequences at their 3' ends. The 5' tail sequences on the primers differed, primer GX-C 3/5 had tail sequence 3/5, and PDHET4 5/2b had tail sequence 5/2b.

Primer dimer 3 was formed between primers GX-C 10/2b and PDHET4 5/2b. which also had 4 base-long complementary sequences at their 3' ends. The 5' tail sequences again differed, but in this case primer GX-C 10/2b had tail sequence 10/2b.

Since the 5' tail sequences on primers used to form primer-dimers 2 and 3 were non-homologous, resulting primer-dimers were termed "HeteroTagged". When sufficient yields of the primer-dimers had been prepared using the PCR, they were electrophoresed on a 1.5% gel, bands were excised and primer-dimers were extracted and purified using a Qiaex II Agarose Gel Extraction Kit (Qiagen Ltd.). The recovered products were then quantified by gel electrophoresis against a known concentration of FX174 RF DNA digested with the restriction endonuclease Hae III (Supplied by Gibco BRL).

METHOD

Reagents Used.
Sigma water tissue culture grade
10 X ARMS buffer
Kodak Taq Polymerase
1 mM dNTPs
Nusieve agarose
Qiaex II Agarose Gel Extraction Kit
1 x TBE buffer, 0.5mg ml$^{-1}$ Ethidium bromide
Gel loading buffer
10 mM Tris-HCl buffer pH 8.5
3 mM Sodium Acetate pH 5.0
FX174 RF DNA/Hae III digest
    Primers
    Primer Sequences in Table 9.
DF508 common 5/2b 5' tail =IF-C3 5/2b
Primer dimer partner 1, 5/2b 5' tail =IF-C3 PD 5/2b
G542X common 3/5 5' tail =GX-C 3/5
G542X common 10/2b 5' tail =GX-C 10/2b
Primer dimer partner 2 & 3, 5/2b 5' tail =PDHET 4 5/2b
    Preparation of Mixes
All mixes contained 100 mM dNTPs, 5 mM of each primer as described in Table 17 and were prepared in 1 X ARMS buffer to a final reaction volume of 100 ml. Each mix was aliquoted into 95 ml volumes and dispensed into 0.65 ml Eppendorf tubes, microfuged and layered with light white mineral oil.

TABLE 17

| | Primers in Primer-Dimer mixes | |
|---|---|---|
| MIX | PRIMER 1 | PRIMER 2 |
| 1 | IF-C3 PD 5/2b | IF-C3 5/2b |
| 2 | GX-C 3/5 | PDHET 4 5/2b |
| 3 | GX-C 10/2b | PDHET 4 5/2b |

Amplification

Tubes were cycled on a Perkin Elmer 480 Thermal Cycler. All tubes were soaked at 94° C. for 5 mins before adding 1 unit 5 ml$^{-1}$ Taq polymerase in 1 x ARMS buffer, then cycled as follows:

4 cycles of (94° C.—1', 60° C.—5', 72° C.—1')
35 cycles of (94° C.—1', 60° C.—5', 72° C.—1')

Detection

Like mixes were pooled and 200 ml of gel loading buffer added to each. The whole of each sample was loaded onto a 1.5% Nusieve agarose gel and electrophoresed at 120 Volts for 1 hour.

Results

Results are shown in FIG. 38.

Conclusions

Sufficient primer-dimer was produced to excise and purify.

GEL EXTRACTION AND PURIFICATION OF PRIMER-DIMERS USING THE QIAEX II AGAROSE GEL EXTRACTION KIT

Bands of the correct size were excised from the gel, separated into 250 mg lots and transferred to 1.5 ml Eppendorf tubes. The protocol below was then followed for each 250 mg of gel:

Method
1. Added 750 ml of Qiaex buffer I (solubilisation buffer).
2. Added 20 ml of Qiaex II and vortexed for 30 sec.
3. Incubated in a water bath at 50° C. for 10 mins, vortexing every 2 mins.
4. pH determined to be >7.5 using pH test strips (BDH Ltd.)
5. Added 10 ml of 3 mM sodium acetate pH 5.0, vortexed and checked pH to determine that it was below 7.0.
6. Incubated tube at room temperature for 10 mins.
7. Microfuged at 13 Krpm for 30 sec.
8. Removed and discarded the supernatant.
9. Resuspended the resulting pellet in 500 ml of Qiaex buffer I.
10. Vortexed and microfuged at 13 Krpm for 30 sec.
11. Removed and discarded the supernatant.
12. Washed the pellet twice in 500 ml of Qiaex buffer II i.e. added buffer, vortexed, microfuged for 30 sec, discarded supernatant and repeated whole process.
13. Allowed the pellet to air dry for 30 mins.
14. Added 20 ml of 100 mM Tris HCl buffer pH 8.5 and resuspended the pellet by vortexing.
15. Incubated at room temperature for 10 mins.
16. Microfuged at 13 Krpm for 30 seconds, collected the supernatant and transferred to a clean 0.65 ml Eppendorf tube.
17. Resuspended the pellet in a further 10 ml of 10 mM Tris-HCl pH 8.5.
18. Incubated at 50° C. for 5 mins.
19. Microfuged for 30 sec at 13 Krpm and collected supernatant.

Finally, all "like" purified primer-dimers were pooled into a fresh 0.65 ml Eppendorf.

Detection

Dilutions (1/1,1/2, 1/5 and 1/10) of each primer-dimer were prepared in Sigma water. 10 ml of each was mixed with 10 ml of gel loading buffer. The whole sample was loaded onto the gel, alongside 100 ng of FX174 RF DNA digested with Hae III. The gel was run at 120V for 1.5 hours.

Results

Results shown in FIG. 39.

Conclusions

Sufficient yields of primer dimer were available for quantification.

QUANTIFICATION

To determine the quantity of purified primer-dimer, the band intensity was compared to the bands given with the FX174 RF DNA/Hae III Fragments. Since the sizes and concentrations of these fragments were known, and the size of the primer-dimer was known, a direct comparison could be made. This was done so using the formula below:

$$\frac{\text{Size of } FX174 \, RF \, DNA/\text{Hae III Fragment equal to primer-dimer band in intensity (base-pairs)}}{\text{Size of } FX174 \, RF \, DNA \text{ pre-digest (base-pairs)}} \times$$

$$\text{weight of } FX174 \, RF \, DNA/\text{Hae III fragments loaded (ng)} =$$

Weight of product loaded onto gel (ng/ml loaded)

Conversion to Number of Molecules per ml sample.

Length of product (bases) × 330 Daltons =

Weight of 1 mole of product (Daltons)

$$\frac{\text{Concentration of product loaded onto gel (ng/ml)} \times 10^{-9}}{\text{Weight of 1 mole of product}} =$$

moles of product ml$^{-1}$ (Moles of product ml$^{-1}$) × (6.023 × 10$^{23}$) =

Number of product molecules ml$^{-1}$

Results

The concentrations of the primer dimers were as follows:

Primer Dimer 1 (HomoTagged)=3×10$^{10}$ molecules ml$^{-1}$

Primer Dimer 2 (HeteroTagged)=7.25×10$^{10}$ molecules ml$^{-1}$

Primer Dimer 3 (HeteroTagged)=4.82×10$^{10}$ molecules ml$^{-1}$

Conclusions

All three primer-dimers were of sufficient quantity to prepare dilution series with and use in the secondary amplification stage of the experiment.

4ii) REAMPLIFICATION OF TAILED PRIMER-DIMERS WITH THE APPROPRIATE TAG PRIMERS

Aim

The aim of the experiment was to demonstrate that a primer-dimer formed from primers with homologous 5' tails at a low concentration could not be reamplified, in contrast to a primer-dimer formed from primers with non-homologous 5' tails.

To demonstrate this, dilution series' of the purified homo- and HeteroTagged primer-dimers were prepared and known concentrations added to mixes containing the appropriate tag primer/s at standard concentration (1 mM). These were then subjected to the PCR and any resulting product was analysed by gel electrophoresis.

METHOD

Reagents Used

Sigma water Tissue Culture Grade 10 x ARMS buffer 1 mM dNTPs

Kodak Taq Polymerase

Primers

Primer sequences in Table 9

Tag 5/2b

Tag 3/5

Tag 10/2b

Preparation of Dilution Series

Each of the primer-dimers were diluted to a 1×10$^{10}$ molecules 5 ml$^{-1}$ using Sigma tissue culture grade water. From this stock the following dilution series was prepared 10$^8$ molecules 5 ml$^{-1}$ 10$^6$ molecules 5 ml$^{-1}$ 10$^5$ molecules 5 ml$^{-1}$ 10$^4$ molecules 5 ml$^{-1}$ 10$^3$ molecules 5 ml$^{-1}$ 10$^2$ molecules 5 ml$^{-1}$ 10$^1$ molecules 5 ml$^{-1}$ Preparation of Mixes All mixes contained 100 mM dNTPs, were prepared in 1 x ARMS buffer to a final reaction volume of 50 ml and contained primers as detailed in Table 18:

TABLE 18

| | Concentration of Tag primers. | |
|---|---|---|
| MIX | PRIMER 1 | PRIMER 2 |
| A | 1 mM Tag 5/2b | — |
| B | 0.5 mM Tag 3/5 | 0.5 mM Tag 5/2b |
| C | 0.5 mM Tag 10/2b | 0.5 mM Tag 5/2b |

Mix A was aliquoted into 18×40 ml volumes, and mixes B and C into 9×40 ml volumes. Mixes were dispensed into 0.65 ml Eppendorf tubes, microfuged and loverlaid with light white mineral oil.

Preparation of Samples

Tubes containing the aliquoted mixes were numbered 1–36 and 5 ml of the appropriate, purified primer-dimer was added as described in table 11. 5 ml of Sigma water was added to the negative controls.

TABLE 19

| TUBE | MIX | PD1 molecules 5 ml$^{-1}$ | TUBE | MIX | PD2 molecules 5 ml$^{-1}$ | TUBE | MIX | PD3 molecules 5 ml$^{-1}$ |
|---|---|---|---|---|---|---|---|---|
| 1 + 10 | A | 10$^{10}$ | 19 | B | 10$^{10}$ | 28 | C | 10$^{10}$ |
| 2 + 11 | A | 10$^8$ | 20 | B | 10$^8$ | 29 | C | 10$^8$ |
| 3 + 12 | A | 10$^6$ | 21 | B | 10$^6$ | 30 | C | 10$^6$ |

TABLE 19-continued

| TUBE | MIX | PD1 molecules 5 ml⁻¹ | TUBE | MIX | PD2 molecules 5 ml⁻¹ | TUBE | MIX | PD3 molecules 5 ml⁻¹ |
|---|---|---|---|---|---|---|---|---|
| 4 + 13 | A | $10^5$ | 22 | B | $10^5$ | 31 | C | $10^5$ |
| 5 + 14 | A | $10^4$ | 23 | B | $10^4$ | 32 | C | $10^4$ |
| 6 + 15 | A | $10^3$ | 24 | B | $10^3$ | 33 | C | $10^3$ |
| 7 + 16 | A | $10^2$ | 25 | B | $10^2$ | 34 | C | $10^2$ |
| 8 + 17 | A | $10^1$ | 26 | B | $10^1$ | 35 | C | $10^1$ |
| 9 + 18 | A | −ve control | 27 | B | −ve control | 36 | C | −ve control |

Amplification

Tubes were cycled on a Perkin Elmer 480 Thermal Cycler. All samples were soaked at 94° C. for 5 mins before adding 1u 5 ml⁻¹ Taq Polymerase in 1x ARMS buffer.

Amplification cycles were as follows:

35 cycles of (94° C.—1',60° C.—1', 72° C.—1')

1 cycle of (72° C.—10')

Detection 20 ml of PCR product was added to 10 ml of gel loading buffer. 15 ml of each sample was loaded onto gels (3% Nusieve agarose) and electrophoresed at 120 Volts for 90 minutes.

Results

Results are shown in FIG. 40.

Conclusions

HomoTagged primer-dimer was sufficiently amplified to be visualised on the gel only when $10^{10}$ target molecules were present in the mix. HeteroTagged primer dimers however, were both efficiently amplified to produce a visible band when as few as 10 molecules of target were present in the mix.

It appears that the HomoTag format therefore, effectively inhibited amplification of primer dimers by the tag primer.

5. DETERMINING THAT THE INHIBITION OF HOMOTAGGED PRIMER-DIMER AMPLIFICATION IS DUE TO A SECONDARY STRUCTURE

Aims

The aim of this experiment was to show that the inhibition of primer-dimer amplification observed when primers were 5' tailed with the same sequence, was due to formation of a "pan-handle" structure. It was hypothesised that this structure is formed by a self-annealing event between the 3' and 5' ends of the molecule strand. If the inhibitory effect was due to the suggested secondary structure formation, it would be possible to reduce inhibition of primer-dimer amplification by increasing the annealing temperature during PCR, to the melting temperature of the tail sequence. This would cause dissociation of a proportion of self-annealed strands liberating the primer-dimer 3' and 5'60 ends for amplification via tag primer.

The 5/2b tag/tail sequence used in the previous experiments was analysed using computer software, and the $T_m$ predicted as 72.5° C. in the PCR mixture used. When the annealing temperature of PCR cycling was raised to above the $T_m$, it was expected that the inhibitory effect would be seen to be reduced due to destabilisation of the "pan-handle" structure.

METHOD

Reagents Used.

Sigma water—tissue culture grade 10 x ARMS buffer

Kodak Taq Polymerase 1 mM dNTPs

Primers

Primer sequence in Table 9.

Tag 5/2b

Preparation of Mix

Prepared mix A containing 100 mM dNTPs, 1 mM tag 5/2b in 1 x ARMS buffer to a final reaction volume of 50 ml. Aliquoted into 9×40 ml volumes and dispensed into 0.65 ml tubes, microfuged and layered with light white mineral oil (Sigma Chemicals Ltd.).

Preparation of Samples

Numbered the reaction tubes from 1–9, and added 5 ml of the appropriate HomoTagged primer-dimer as described in table 12. Added 5 ml of Sigma tissue culture grade water to the negative control.

TABLE 20

Composition of Mixes

| TUBE | MIX | PD 1 molecules 5 ml⁻¹ | TUBE | MIX | PD 1 molecules 5 ml⁻¹ |
|---|---|---|---|---|---|
| 1 | A | $10^{10}$ | 6 | A | $10^3$ |
| 2 | A | $10^8$ | 7 | A | $10^2$ |
| 3 | A | $10^6$ | 8 | A | $10^1$ |
| 4 | A | $10^5$ | 9 | A | −ve |
| 5 | A | $10^4$ | — | — | — |

Amplification

Samples were cycled on a Perkin Elmer 480 Thermal Cycler. All tubes were soaked at 94° C. for 5 minutes before adding 1 u 5 ml⁻¹ Taq Polymerase in 1 x ARMS buffer. Amplification cycles were as follows:

35 cycles of (94° C.—1', 74° C.—2')

1 cycle of (72° C.—10')

Detection 20 ml of PCR product was added to 10 ml of gel loading buffer. 15 ml of each sample was loaded onto gels (3% Nusieve agarose) and electrophoresed at 120 Volts for 90 minutes.

Results

Results are shown in FIG. 41.

Conclusions

By increasing the annealing temperature of the PCR cycle from 60° C. to 74° C. i.e. above the $T_m$ of the tail sequence, primer dimer was successfully amplified when fewer template molecules ($10^6$ c.f. $10^{10}$ at 60° C. annealing) were added to the reaction.

It was concluded that the inhibition of primer-dimer amplification in a HomoTag format is due to the self-annealing ability of the 3' and 5' ends of the primer-dimer strand.

We claim:

1. A method for detecting the presence or absence of at least one diagnostic base sequence in one or more nucleic acids contained in a sample, which method comprises contacting the sample with a diagnostic primer for each diagnostic base sequence, the nucleotide sequence of each diagnostic primer being such that it is substantially complementary to the corresponding diagnostic base sequence, under hybridising conditions and in the presence of appropriate nucleoside triphosphates and an agent for polymerisation thereof, such that an extension product of a diagnostic primer is synthesised when the corresponding diagnostic base sequence is present in the sample, no extension product being synthesised when the corresponding diagnostic base sequence is not present in the sample and any extension product of a diagnostic primer acts as template for extension of a further primer which hybridises to a locus at a distance from the relevant diagnostic base sequence, and wherein at least one of the diagnostic primer(s) further comprises a tail sequence which does not hybridise to a diagnostic base sequence or a region adjacent thereto, and contacting the above mixture with a tail specific primer which hybridises to the complement of the tail sequence in an extension product of the further primer and is extended in the presence of appropriate nucleoside triphosphates and an agent for polymerisation thereof to amplify the further primer amplification products whereby the presence or absence of the diagnostic base sequence(s) is detected from the presence or absence of tail specific primer extension product.

2. A method as claimed in claim 1 wherein a single, common tail specific primer is used for all the diagnostic primers comprising tail sequences for use with the common tail specific primer.

3. A method as claimed in claim 1 wherein a single common tail specific primer is used for all primers and these all comprise tail sequences for use with the common tail specific primer.

4. A method as claimed in claim 1 wherein one or more of the diagnostic primers is an allele specific primer.

5. A method as claimed in claim 1 wherein two or more competitive oligonucleotide primers are used to detect variant nucleotide(s) in at least one diagnostic base sequence.

6. A method as claimed in claim 1 wherein a terminal nucleotide of at least one diagnostic primer is either complementary to a suspected variant nucleotide or to the corresponding normal nucleotide, such that an extension product of a diagnostic primer is synthesised when the terminal nucleotide of the diagnostic primer is complementary to the corresponding nucleotide in the diagnostic base sequence, no extension product being synthesised when the terminal nucleotide of the diagnostic primer is not complementary to the corresponding nucleotide in the diagnostic base sequence.

7. A method as claimed in claim wherein extension products of at least two diagnostic primers comprise a complementary overlap.

8. A method as claimed in claim 7 and wherein at least two diagnostic primers comprise a complementary overlap.

9. A method as claimed in claim 1 wherein the ratio of tail specific and/or further primer(s) to diagnostic primer(s) is at least 1:1.

10. A method as claimed in claim 9 wherein the ratio is at least 50:1.

11. A kit for detecting the presence or absence of at least one variant nucleotide in one or more nucleic acids contained in a sample, which kit comprises:

a diagnostic primer for each diagnostic portion of a target base sequence, the nucleotide sequence of each diagnostic primer being such that it is substantially complementary to the said diagnostic portion, a terminal nucleotide of the diagnostic primer being either complementary to the suspected variant nucleotide or to the corresponding normal nucleotide, such that in use an extension product of the diagnostic primer is synthesised when the said terminal nucleotide of the diagnostic primer is complementary to the corresponding nucleotide in the target base sequence, no extension product being synthesised when the said terminal nucleotide of the diagnostic primer is not complementary to the corresponding nucleotide in the target base sequence; at least one diagnostic primer further comprising a tail sequence for hybridisation to a tail specific primer which hybridises to the complement of the tail sequence in the extension product of the common primer and which tail sequence does not hybridise to the target base sequence or a region adjacent thereto, together with appropriate buffer, packaging and instructions for use.

12. A kit as claimed in claim 11 which further comprises at least one of the following items:
 (i) each of four different nucleoside triphosphates
 (ii) an agent for polymerisation of the nucleoside triphosphates in (i)
 (iii) tail specific primer(s)
 (iv) a second primer which hybridises to a region at a distance from the diagnostic region(s) to which the diagnostic primer(s) selectively hybridise.

13. A kit as claimed in claim 11 which comprises a set of at least two diagnostic primers for each diagnostic portion of a target base sequence.

14. A kit as claimed in claim 13 wherein a terminal nucleotide of one diagnostic primer is complementary to a suspected variant nucleotide associated with a known genetic disorder and a terminal nucleotide of another diagnostic primer is complementary to the corresponding normal nucleotide.

15. A method as claimed in claim 1 and performed as a homogenous polymerase chain reaction assay.

16. A method as claimed in claim 1 wherein intercalating dye(s) are used to detect tail specific primer extension products.

17. A method as claimed in claim 1 wherein the diagnostic primer and tail specific primer sequences are selected such that an increase in temperature is used to favour tail specific primer priming over diagnostic primer priming.

* * * * *